(12) United States Patent
Caldas et al.

(10) Patent No.: US 8,017,747 B2
(45) Date of Patent: Sep. 13, 2011

(54) APOPTOSIS-INDUCING GENES FOR TREATING CANCER

(75) Inventors: Hannah Caldas, Phoenix, AZ (US); Rachel A. Altura, Sharon, MA (US)

(73) Assignee: Nationwide Children's Hospital, Inc., Columbus, OH (US)

( * ) Notice: Subject to any disclaimer, the term of this patent is extended or adjusted under 35 U.S.C. 154(b) by 681 days.

(21) Appl. No.: 11/661,224

(22) PCT Filed: Aug. 26, 2005

(86) PCT No.: PCT/US2005/030451
§ 371 (c)(1),
(2), (4) Date: Dec. 13, 2007

(87) PCT Pub. No.: WO2006/026451
PCT Pub. Date: Mar. 9, 2006

(65) Prior Publication Data
US 2009/0239937 A1    Sep. 24, 2009

Related U.S. Application Data

(60) Provisional application No. 60/604,935, filed on Aug. 26, 2004.

(51) Int. Cl.
*C12N 15/11* (2006.01)

(52) U.S. Cl. ........................... 536/23.1; 435/975
(58) Field of Classification Search .............. 536/23.1; 435/975
See application file for complete search history.

(56) References Cited

U.S. PATENT DOCUMENTS 7,026,121 B1 *   4/2006  Wohlgemuth et al. ............ 435/6
7,101,977 B2 *   9/2006  Rosenblum et al. ........ 530/387.1

OTHER PUBLICATIONS

Ling et al (JBC, 279(15): 15196-15203, Apr. 9, 2004).*
Reed et al (Clin Cancer Res, 9: 6310-6315, 2003).*
Schimmer et al (Cancer Research, 63: 1242-1248, 2003).*
STIC Search-Alignment SEQ ID No. 3—(Mar. 24, 2002).*
STIC Search-Alignment SEQ ID No. 4 (Jun. 17, 2002).*

* cited by examiner

*Primary Examiner* — Thaian N Ton
*Assistant Examiner* — Magdalene Sgagias
(74) *Attorney, Agent, or Firm* — Marshall, Gerstein & Borun LLP

(57) ABSTRACT

The invention provides materials and methods related to the use of recombinant nucleic acid molecules containing an expression control element of an inhibitor of apoptosis protein (IAP) gene operatively linked to a coding region for an active cytotoxic/cytolytic agent. The recombinant molecules are used in methods to treat a variety of diseases and disorders, including a wide range of cancers.

3 Claims, 13 Drawing Sheets

A

B

SEQUENCE LISTING

<160> NUMBER OF SEQ ID NOS: 56

<210> SEQ ID NO 1
<211> LENGTH: 268

<212> TYPE: DNA
<213> ORGANISM: Homo sapiens
<220> FEATURE:
<221> NAME/KEY: misc_feature
<222> LOCATION: (68)..(68)
<223> OTHER INFORMATION: Alternative 5' endpoint

<400> SEQUENCE: 1

| | | | | | |
|---|---|---|---|---|---|
| gttctttgaa | agcagtcgag | ggggtgctag | gtgtgggcag | ggacgagctg | gcgcggcgtc | 60 |
| gctgggtgca | ccgcgaccac | gggcagagcc | acgcggcggg | aggactacaa | ctcccggcac | 120 |
| accccgcgcc | gccccgcctc | tactcccaga | aggccgcggg | gggtggaccg | cctaagaggg | 180 |
| cgtgcgctcc | cgacatgccc | cgcggcgcgc | cattaaccgc | cagatttgaa | tcgccggacc | 240 |
| cgttggcaga | ggtggcggcg | gcggcatc | | | | 268 |

<210> SEQ ID NO 2
<211> LENGTH: 689
<212> TYPE: DNA
<213> ORGANISM: Homo sapiens

<400> SEQUENCE: 2

| | | | | | |
|---|---|---|---|---|---|
| gggagatcat | cgggggacat | gaggccaagc | cccactcccg | cccctacatg | gcttatctta | 60 |
| tgatctggga | tcagaagtct | ctgaagaggt | gcggtggctt | cctgatacga | gacgacttcg | 120 |
| tgctgacagc | tgctcactgt | tggggaagct | ccataaatgt | caccttgggg | gcccacaata | 180 |
| tcaaagaaca | ggagccgacc | cagcagttta | tccctgtgaa | agacccatc | ccccatccag | 240 |
| cctataatcc | taagaacttc | tccaacgaca | tcatgctact | gcagctggag | agaaaggcca | 300 |
| agcggaccag | agctgtgcag | cccctcaggc | tacctagcaa | caaggcccag | gtgaagccag | 360 |
| ggcagacatg | cagtgtggcc | ggctggggc | agacggcccc | cctgggaaaa | cactcacaca | 420 |
| cactacaaga | ggtgaagatg | acagtgcagg | aagatcgaaa | gtgcgaatct | gacttacgcc | 480 |
| attattacga | cagtaccatt | gagttgtgcg | tggggggacc | agagattaaa | aagacttcct | 540 |
| ttaaggggga | ctctggaggc | cctcttgtgt | gtaacaaggt | ggcccagggc | attgtctcct | 600 |
| atggacgaaa | caatggcatg | cctccacgag | cctgcaccaa | agtctcaagc | tttgtacact | 660 |
| ggataaagaa | aaccatgaaa | cgctactaa | | | | 689 |

<210> SEQ ID NO 3
<211> LENGTH: 955
<212> TYPE: DNA
<213> ORGANISM: Homo sapiens
<220> FEATURE:
<221> NAME/KEY: misc_feature
<222> LOCATION: (122)..(810)
<223> OTHER INFORMATION: Active granzyme B

<400> SEQUENCE: 3

| | | | | | |
|---|---|---|---|---|---|
| ccaagagcta | aaagagagta | agggggaaac | aacagcagct | ccaaccaggg | cagccttcct | 60 |
| gagaagatgc | aaccaatcct | gcttctgctg | gccttcctcc | tgctgcccag | ggcagatgca | 120 |
| ggggagatca | tcgggggaca | tgaggccaag | cccactccc | gcccctacat | ggcttatctt | 180 |
| atgatctggg | atcagaagtc | tctgaagagg | tgcggtggct | tcctgataca | agacgacttc | 240 |
| gtgctgacag | ctgctcactg | ttggggaagc | tccataaatg | tcaccttggg | ggcccacaat | 300 |
| atcaaagaac | aggagccgac | ccagcagttt | atccctgtga | aagacccat | ccccatcca | 360 |
| gcctataatc | ctaagaactt | ctccaacgac | atcatgctac | tgcagctgga | gagaaaggcc | 420 |
| aagcggacca | gagctgtgca | gcccctcagg | ctacctagca | acaaggccca | ggtgaagcca | 480 |
| gggcagacat | gcagtgtggc | cggctggggg | cagacggccc | cctgggaaa | acactcacac | 540 |

-continued

```
acactacaag aggtgaagat gacagtgcag gaagatcgaa agtgcgaatc tgacttacgc    600
cattattacg acagtaccat tgagttgtgc gtgggggacc cagagattaa aaagacttcc    660
tttaaggggg actctggagg ccctcttgtg tgtaacaagg tggcccaggg cattgtctcc    720
tatggacgaa acaatggcat gcctccacga gcctgcacca aagtctcaag ctttgtacac    780
tggataaaga aaccatgaa acgctactaa ctacaggaag caaactaagc ccccgctgta    840
atgaaacacc ttctctggag ccaagtccag atttacactg ggagaggtgc cagcaactga    900
ataaataccT cttagctgag tggaaaaaaa aaaaaaaaa aaaaaaaaa aaaaa           955
```

```
<210> SEQ ID NO 4
<211> LENGTH: 247
<212> TYPE: PRT
<213> ORGANISM: Homo sapiens
<220> FEATURE:
<221> NAME/KEY: misc_feature
<222> LOCATION: (19)..(247)
<223> OTHER INFORMATION: Active Granzyme B

<400> SEQUENCE: 4
```

Met Gln Pro Ile Leu Leu Leu Ala Phe Leu Leu Leu Pro Arg Ala
1               5                   10                  15

Asp Ala Gly Glu Ile Ile Gly Gly His Glu Ala Lys Pro His Ser Arg
            20                  25                  30

Pro Tyr Met Ala Tyr Leu Met Ile Trp Asp Gln Lys Ser Leu Lys Arg
        35                  40                  45

Cys Gly Gly Phe Leu Ile Gln Asp Asp Phe Val Leu Thr Ala Ala His
    50                  55                  60

Cys Trp Gly Ser Ser Ile Asn Val Thr Leu Gly Ala His Asn Ile Lys
65                  70                  75                  80

Glu Gln Glu Pro Thr Gln Gln Phe Ile Pro Val Lys Arg Pro Ile Pro
                85                  90                  95

His Pro Ala Tyr Asn Pro Lys Asn Phe Ser Asn Asp Ile Met Leu Leu
            100                 105                 110

Gln Leu Glu Arg Lys Ala Lys Arg Thr Arg Ala Val Gln Pro Leu Arg
        115                 120                 125

Leu Pro Ser Asn Lys Ala Gln Val Lys Pro Gly Gln Thr Cys Ser Val
    130                 135                 140

Ala Gly Trp Gly Gln Thr Ala Pro Leu Gly Lys His Ser His Thr Leu
145                 150                 155                 160

Gln Glu Val Lys Met Thr Val Gln Glu Asp Arg Lys Cys Glu Ser Asp
                165                 170                 175

Leu Arg His Tyr Tyr Asp Ser Thr Ile Glu Leu Cys Val Gly Asp Pro
            180                 185                 190

Glu Ile Lys Lys Thr Ser Phe Lys Gly Asp Ser Gly Gly Pro Leu Val
        195                 200                 205

Cys Asn Lys Val Ala Gln Gly Ile Val Ser Tyr Gly Arg Asn Asn Gly
    210                 215                 220

Met Pro Pro Arg Ala Cys Thr Lys Val Ser Ser Phe Val His Trp Ile
225                 230                 235                 240

Lys Lys Thr Met Lys Arg Tyr
                245

```
<210> SEQ ID NO 5
<211> LENGTH: 900
<212> TYPE: DNA
<213> ORGANISM: Homo sapiens
```

<400> SEQUENCE: 5

```
cggcacgagg ctgagaagat gcaaccaatc ctgcttctgc tggccttcct cctgctgccc    60
agggcagatg cagacttttc cttcagggga gatcatcggg ggacatgagg ccaagcccca   120
ctcccgcccc tacatggctt atcttatgat ctgggatcag aagtctctga agaggtgcgg   180
tggcttcctg atacaagacg acttcgtgct gacagctgct cactgttggg gaagctccat   240
aaatgtcacc ttgggggccc acaatatcaa agaacaggag ccgacccagc agtttatccc   300
tgtgaaaaga cccatccccc atccagccta taatcctaag aacttctcca acgacatcat   360
gctactgcag ctggagagaa aggccaagcg gaccagagct gtgcagcccc tcaggctacc   420
tagcaacaag gcccaggtga agccagggca gacatgcagt gtggccggct ggggcagac   480
ggcccccctg gaaaacact cacacacact acaagaggtg aagatgacag tgcaggaaga   540
tcgaaagtgc gaatctgact acgccatta ttacgacagt accattgagt tgtgcgtggg   600
ggacccagag attaaaaaga cttcctttaa ggggactct ggaggcccc ttgtgtgtaa   660
caaggtggcc cagggcattg tctcctatgg acgaaacaat ggcatgcctc acgagcctg   720
caccaaagtc tcaagctttg tacactggat aaagaaaacc atgaaacgct actaactaca   780
ggaagcaaac taagcccccg ctgtaatgaa acaccttctc tggagccaag tccagattta   840
cactgggaga ggtgccagca actgaataaa tacctcttag ctgagtggaa aaaaaaaaa   900
```

<210> SEQ ID NO 6
<211> LENGTH: 235
<212> TYPE: PRT
<213> ORGANISM: Homo sapiens
<220> FEATURE:
<221> NAME/KEY: misc_feature
<222> LOCATION: (7)..(235)
<223> OTHER INFORMATION: Active Granzyme B

<400> SEQUENCE: 6

Met Gln Thr Phe Pro Ser Gly Glu Ile Ile Gly Gly His Glu Ala Lys
1               5                   10                  15

Pro His Ser Arg Pro Tyr Met Ala Tyr Leu Met Ile Trp Asp Gln Lys
            20                  25                  30

Ser Leu Lys Arg Cys Gly Gly Phe Leu Ile Gln Asp Asp Phe Val Leu
        35                  40                  45

Thr Ala Ala His Cys Trp Gly Ser Ser Ile Asn Val Thr Leu Gly Ala
    50                  55                  60

His Asn Ile Lys Glu Gln Glu Pro Thr Gln Gln Phe Ile Pro Val Lys
65                  70                  75                  80

Arg Pro Ile Pro His Pro Ala Tyr Asn Pro Lys Asn Phe Ser Asn Asp
                85                  90                  95

Ile Met Leu Leu Gln Leu Glu Arg Lys Ala Lys Arg Thr Arg Ala Val
            100                 105                 110

Gln Pro Leu Arg Leu Pro Ser Asn Lys Ala Gln Val Lys Pro Gly Gln
        115                 120                 125

Thr Cys Ser Val Ala Gly Trp Gly Gln Thr Ala Pro Leu Gly Lys His
    130                 135                 140

Ser His Thr Leu Gln Glu Val Lys Met Thr Val Gln Glu Asp Arg Lys
145                 150                 155                 160

Cys Glu Ser Asp Leu Arg His Tyr Tyr Asp Ser Thr Ile Glu Leu Cys
                165                 170                 175

Val Gly Asp Pro Glu Ile Lys Lys Thr Ser Phe Lys Gly Asp Ser Gly
            180                 185                 190

Gly Pro Leu Val Cys Asn Lys Val Ala Gln Gly Ile Val Ser Tyr Gly
            195                 200                 205

Arg Asn Asn Gly Met Pro Pro Arg Ala Cys Thr Lys Val Ser Ser Phe
        210                 215                 220

Val His Trp Ile Lys Lys Thr Met Lys Arg Tyr
225                 230                 235

<210> SEQ ID NO 7
<211> LENGTH: 1452
<212> TYPE: DNA
<213> ORGANISM: Mus musculus

<400> SEQUENCE: 7

```
gggggtacaa ggtcacagag cccctctgc cttcttcctc tcctagaggt taaaagagag    60
caaggacaac actcttgacg ctgggaccta ggcggccttc cggggaagat gaagatcctc   120
ctgctactgc tgaccttgtc tctggcctcc aggacaaagg caggggagat catcggggga   180
catgaagtca agccccactc tcgaccctac atggccttac tttcgatcaa ggatcagcag   240
cctgaggcga tatgtggggg cttccttatt cgagaggact ttgtgctgac tgctgctcac   300
tgtgaaggaa gtataataaa tgtcactttg ggggcccaca acatcaaaga acaggagaag   360
acccagcaag tcatccctat ggtaaaatgc attcccacc cagactataa tcctaagaca   420
ttctccaatg acatcatgct gctaaagctg aagagtaagg ccaagaggac tagagctgtg   480
aggccctca acctgcccag cgcaatgtc aatgtgaagc caggagatgt gtgctatgtg    540
gctggttggg gaaggatggc cccaatgggc aaatactcaa acacgctaca agaggttgag   600
ctgacagtac agaaggatcg ggagtgtgag tcctacttta aaaatcgtta caacaaaacc   660
aatcagatat gtgcggggga cccaaagacc aaacgtgctt cctttcgggg ggattctgga   720
ggcccgcttg tgtgtaaaaa agtggctgca ggcatagttt cctatggata taggatggt   780
tcacctccac gtgctttcac caaagtctcg agtttcttat cctggataaa gaaacaatg   840
aaaagcagct aactacagaa gcaacatgga tcctgctctg attacccatc gtccctagag   900
ctgagtccag gattgctcta ggacaggtgg caggatctga ataaaggact gcaaagactg   960
gcttcatgtc cattcacaag gaccagctct gtccttggca ggccaatgga cacctcttc  1020
tgccaccatg ctgtgacaac ccaactgaca tcttcctatg gaagtttgcc ctctccacaa  1080
aagaagtaga atgtttgcat tggagctggg catgctctgc ttcccctcag tgccccgaga  1140
atgttatcta atgctagtca tcattaatag ctccctacag aactttcata cagttgcacc  1200
caagttgctg atgtgttctc tagaatagag caagaaatag taaacagaat tccttttgcc  1260
tctctgtact attttccccc aaataccaag atttgtatgt tttataaagc taattcctt  1320
atcaaatgac atcttttaat ttttacatta atggcttatt ttcaaggtac aacctgattt  1380
ttttatggac aaaaatgatg taaaatcaaa taaaactaat taatatatcc attaaaaaaa  1440
aaaaaaaaaa aa                                                    1452
```

<210> SEQ ID NO 8
<211> LENGTH: 247
<212> TYPE: PRT
<213> ORGANISM: Mus musculus
<220> FEATURE:
<221> NAME/KEY: misc_feature
<222> LOCATION: (19)..(247)
<223> OTHER INFORMATION: Active Granzyme B

<400> SEQUENCE: 8

```
Met Lys Ile Leu Leu Leu Leu Thr Leu Ser Leu Ala Ser Arg Thr
1               5                   10                  15

Lys Ala Gly Glu Ile Ile Gly Gly His Glu Val Lys Pro His Ser Arg
            20                  25                  30

Pro Tyr Met Ala Leu Leu Ser Ile Lys Asp Gln Gln Pro Glu Ala Ile
        35                  40                  45

Cys Gly Gly Phe Leu Ile Arg Glu Asp Phe Val Leu Thr Ala Ala His
50                  55                  60

Cys Glu Gly Ser Ile Ile Asn Val Thr Leu Gly Ala His Asn Ile Lys
65                  70                  75                  80

Glu Gln Glu Lys Thr Gln Gln Val Ile Pro Met Val Lys Cys Ile Pro
                85                  90                  95

His Pro Asp Tyr Asn Pro Lys Thr Phe Ser Asn Asp Ile Met Leu Leu
            100                 105                 110

Lys Leu Lys Ser Lys Ala Lys Arg Thr Arg Ala Val Arg Pro Leu Asn
        115                 120                 125

Leu Pro Arg Arg Asn Val Asn Val Lys Pro Gly Asp Val Cys Tyr Val
130                 135                 140

Ala Gly Trp Gly Arg Met Ala Pro Met Gly Lys Tyr Ser Asn Thr Leu
145                 150                 155                 160

Gln Glu Val Glu Leu Thr Val Gln Lys Asp Arg Glu Cys Glu Ser Tyr
                165                 170                 175

Phe Lys Asn Arg Tyr Asn Lys Thr Asn Gln Ile Cys Ala Gly Asp Pro
            180                 185                 190

Lys Thr Lys Arg Ala Ser Phe Arg Gly Asp Ser Gly Pro Leu Val
        195                 200                 205

Cys Lys Lys Val Ala Ala Gly Ile Val Ser Tyr Gly Tyr Lys Asp Gly
210                 215                 220

Ser Pro Pro Arg Ala Phe Thr Lys Val Ser Ser Phe Leu Ser Trp Ile
225                 230                 235                 240

Lys Lys Thr Met Lys Ser Ser
                245
```

<210> SEQ ID NO 9
<211> LENGTH: 1113
<212> TYPE: DNA
<213> ORGANISM: Rattus norvegicus

<400> SEQUENCE: 9

```
cataagatgt atgtgtaggg ggtgtaagag tactcgtgag gggtgtgggc agtgttatag    60
ggtgctggtg agcaaaccct ctgggaccta ggtggccttc agggaagat gaagctcctc    120
ttgctcctgc tgagcttctc tctggcccc aagacagagg caggggagat catcggggga    180
catgaagcca gccccactc tcgaccctac atggcctatc ttcagatcat ggatgagtat    240
tctgggagta agaagtgtgg cggcttcctt atacgagaag actttgtgct gactgctgct    300
cactgttcgg gaagcaaaat aaatgtcacg ttggggccc acaacatcaa agaacaggag    360
aagatgcaac aaatcatccc tgtggtgaaa atcattcccc acccagcgta taattctaag    420
acaatctcca atgacatcat gctgttaaag ctgaagagta aggccaagag gtctagcgct    480
gtgaagcctc tcaatctgcc cagacgcaac gtcaaagtga accaggaga tgtgtgctat    540
gtggctggtt ggggaaagct gggcccaatg ggcaaatact cagacacact acaagaggtt    600
gagctaacag tacaggagga tcagaagtgt gagtcctact taaaaaatta tttcgacaaa    660
gccaatgaga tatgtgcagg ggacccaaag atcaaacgtg cttcctttcg ggggactct    720
```

-continued

```
ggagggcctc ttgtgtgtaa aaaagtggcc gcgggcatcg tctcctatgg acaaaatgat    780
ggttcaactc cacgggcatt caccaaagtc tcgactttcc tatcatggat aaagaaaact    840
atgaaaaaga gctaactaca agaagcaaca tggatcattt cctgactaac catctgccct    900
atagctgagt ccaggattgc tctaggacag atggcagcaa ctgaataaag cacttttttt    960
ctgagactgg ttgactggtt tcatgtccat tcacagtgat caaccctgtc cttggcagat    1020
gaatggaatg cttctgccac aaggctgtga caacccagct gacatctgct agttcaccct    1080
ctctacaaga gaagaagaat gtttgattgt ccg                                 1113
```

<210> SEQ ID NO 10
<211> LENGTH: 248
<212> TYPE: PRT
<213> ORGANISM: Rattus norvegicus
<220> FEATURE:
<221> NAME/KEY: misc_feature
<222> LOCATION: (19)..(248)
<223> OTHER INFORMATION: Active Granzyme B

<400> SEQUENCE: 10

```
Met Lys Leu Leu Leu Leu Leu Ser Phe Ser Leu Ala Pro Lys Thr
1               5                   10                  15

Glu Ala Gly Glu Ile Ile Gly Gly His Glu Ala Lys Pro His Ser Arg
            20                  25                  30

Pro Tyr Met Ala Tyr Leu Gln Ile Met Asp Glu Tyr Ser Gly Ser Lys
        35                  40                  45

Lys Cys Gly Gly Phe Leu Ile Arg Glu Asp Phe Val Leu Thr Ala Ala
    50                  55                  60

His Cys Ser Gly Ser Lys Ile Asn Val Thr Leu Gly Ala His Asn Ile
65                  70                  75                  80

Lys Glu Gln Glu Lys Met Gln Gln Ile Ile Pro Val Val Lys Ile Ile
                85                  90                  95

Pro His Pro Ala Tyr Asn Ser Lys Thr Ile Ser Asn Asp Ile Met Leu
            100                 105                 110

Leu Lys Leu Lys Ser Lys Ala Lys Arg Ser Ser Ala Val Lys Pro Leu
        115                 120                 125

Asn Leu Pro Arg Arg Asn Val Lys Val Lys Pro Gly Asp Val Cys Tyr
    130                 135                 140

Val Ala Gly Trp Gly Lys Leu Gly Pro Met Gly Lys Tyr Ser Asp Thr
145                 150                 155                 160

Leu Gln Glu Val Glu Leu Thr Val Gln Glu Asp Gln Lys Cys Glu Ser
                165                 170                 175

Tyr Leu Lys Asn Tyr Phe Asp Lys Ala Asn Glu Ile Cys Ala Gly Asp
            180                 185                 190

Pro Lys Ile Lys Arg Ala Ser Phe Arg Gly Asp Ser Gly Gly Pro Leu
        195                 200                 205

Val Cys Lys Lys Val Ala Ala Gly Ile Val Ser Tyr Gly Gln Asn Asp
    210                 215                 220

Gly Ser Thr Pro Arg Ala Phe Thr Lys Val Ser Thr Phe Leu Ser Trp
225                 230                 235                 240

Ile Lys Lys Thr Met Lys Lys Ser
                245
```

<210> SEQ ID NO 11
<211> LENGTH: 559
<212> TYPE: DNA
<213> ORGANISM: Marmota monax

```
<400> SEQUENCE: 11
ctgctcactg ttggggaagg ccaatgaacg tcaccctggg agcacacaac attgagaatc    60
tggagaagac ccagcaggtc atcccagtga aagaaccat ccccccaccca gactatgatg   120 ctcattattt ctacaatgac atcatgttat tggagctaga gaaaaaagcc aaccttaatc   180
cagctgtgca gcctatcaag ctgcccaggg gcaaggacaa ggtgaagcct gggaaggtgt   240
gccttgtggc tggctgggc agaatggccc gaaatggcaa ataccccaac acactgcagg    300
aggtaaagct gaaagtgcag aagcaccagg tgtgcgagcg cgaggaatta ttaaaagagt   360
actacaagag tagcatccag atatgtgtgg gggatccaaa ggaaaacaaa gcttcctttc   420 aggggactc cggaggccct cttgtgtgta accatgtggc ccaaggaatt gtctcttatg    480
gaaataaaaa tgggaaacct ccccgtgtct acaccaaagt ctccagattc ctacaatgga   540
taaagaaaac catgaaacg                                                559
```

```
<210> SEQ ID NO 12
<211> LENGTH: 186
<212> TYPE: PRT
<213> ORGANISM: Marmota monax

<400> SEQUENCE: 12

Ala His Cys Trp Gly Arg Pro Met Asn Val Thr Leu Gly Ala His Asn
1               5                   10                  15

Ile Glu Asn Leu Glu Lys Thr Gln Gln Val Ile Pro Val Lys Arg Thr
            20                  25                  30

Ile Pro His Pro Asp Tyr Asp Ala His Tyr Phe Tyr Asn Asp Ile Met
        35                  40                  45

Leu Leu Glu Leu Glu Lys Lys Ala Asn Leu Asn Pro Ala Val Gln Pro
    50                  55                  60

Ile Lys Leu Pro Arg Gly Lys Asp Lys Val Lys Pro Gly Lys Val Cys
65                  70                  75                  80

Leu Val Ala Gly Trp Gly Arg Met Ala Arg Asn Gly Lys Tyr Pro Asn
                85                  90                  95

Thr Leu Gln Glu Val Lys Leu Lys Val Gln Lys His Gln Val Cys Glu
            100                 105                 110

Arg Glu Glu Leu Leu Lys Glu Tyr Tyr Lys Ser Ser Ile Gln Ile Cys
        115                 120                 125

Val Gly Asp Pro Lys Glu Asn Lys Ala Ser Phe Gln Gly Asp Ser Gly
    130                 135                 140

Gly Pro Leu Val Cys Asn His Val Ala Gln Gly Ile Val Ser Tyr Gly
145                 150                 155                 160

Asn Lys Asn Gly Lys Pro Pro Arg Val Tyr Thr Lys Val Ser Arg Phe
                165                 170                 175

Leu Gln Trp Ile Lys Lys Thr Met Lys Arg
            180                 185
```

```
<210> SEQ ID NO 13
<211> LENGTH: 876
<212> TYPE: DNA
<213> ORGANISM: Bos taurus

<400> SEQUENCE: 13
tctgggcagt cttcctggag agatggtcct gctcctgctc ctggtggccc ttctgtcccc    60
tactggggag gcagggaaaa tcatcggggg tcacgaggcc aagccacact cccgtcccta   120
catggcgttt cttctgttca agacttcagg gaaatctcac atatgtgggg gtttccttgt   180
```

```
gcgtgaggac ttcgtgctga cagcagctca ctgcctggga agctcaatca atgtcaccct    240
gggggcccat aacatcatgg aacgagagag gacccagcag gtcatcccag tgagaagacc    300
catcccccac ccagactata atgatgagac tttggccaac gacatcatgt tactgaagct    360
gactaggaag gctgacatta cggataaagt gagcccatc aatctgccca ggagcttggc     420
ggaggtgaag ccagggatga tgtgcagtgt ggccggctgg gggcgactgg gggtaaatat    480
gccctctaca gacaatctac aggaggtaga tcttgaagtc caaagtgagg agaaatgtat    540
cgctcgcttc aaaaactaca tccccttcac acagatatgt gctggagatc caagcaagag    600
gaagaattct ttctcgggtg actctggggg cccgcttgtg tgtaatggtg tggcccaggg    660
cattgtgtcc tatggaagaa atgatgggac aactccagat gtctacacca gaatctccag    720
ctttctgtcc tggatccatt caacaatgag acggtacaaa cgccaggat cagtgtgatg      780 tgtgctcagg gtggaccct ccatgttccc tgggattgga agcattgatc aaagtgtgtg     840
aaggaaggtt gcctggaact taataaacat tcatct                              876
```

```
<210> SEQ ID NO 14
<211> LENGTH: 251
<212> TYPE: PRT
<213> ORGANISM: Bos taurus
<220> FEATURE:
<221> NAME/KEY: misc_feature
<222> LOCATION: (18)..(251)
<223> OTHER INFORMATION: Active Granzyme B

<400> SEQUENCE: 14

Met Val Leu Leu Leu Leu Val Ala Leu Leu Ser Pro Thr Gly Glu
1               5                   10                  15

Ala Gly Lys Ile Ile Gly Gly His Glu Ala Lys Pro His Ser Arg Pro
            20                  25                  30

Tyr Met Ala Phe Leu Leu Phe Lys Thr Ser Gly Lys Ser His Ile Cys
        35                  40                  45

Gly Gly Phe Leu Val Arg Glu Asp Phe Val Leu Thr Ala Ala His Cys
    50                  55                  60

Leu Gly Ser Ser Ile Asn Val Thr Leu Gly Ala His Asn Ile Met Glu
65                  70                  75                  80

Arg Glu Arg Thr Gln Gln Val Ile Pro Val Arg Arg Pro Ile Pro His
                85                  90                  95

Pro Asp Tyr Asn Asp Glu Thr Leu Ala Asn Asp Ile Met Leu Leu Lys
            100                 105                 110

Leu Thr Arg Lys Ala Asp Ile Thr Asp Lys Val Ser Pro Ile Asn Leu
        115                 120                 125

Pro Arg Ser Leu Ala Glu Val Lys Pro Gly Met Met Cys Ser Val Ala
    130                 135                 140

Gly Trp Gly Arg Leu Gly Val Asn Met Pro Ser Thr Asp Asn Leu Gln
145                 150                 155                 160

Glu Val Asp Leu Glu Val Gln Ser Glu Glu Lys Cys Ile Ala Arg Phe
                165                 170                 175

Lys Asn Tyr Ile Pro Phe Thr Gln Ile Cys Ala Gly Asp Pro Ser Lys
            180                 185                 190

Arg Lys Asn Ser Phe Ser Gly Asp Ser Gly Gly Pro Leu Val Cys Asn
        195                 200                 205

Gly Val Ala Gln Gly Ile Val Ser Tyr Gly Arg Asn Asp Gly Thr Thr
    210                 215                 220

Pro Asp Val Tyr Thr Arg Ile Ser Ser Phe Leu Ser Trp Ile His Ser
225                 230                 235                 240
```

Thr Met Arg Arg Tyr Lys Arg Gln Gly Ser Val
            245                 250

<210> SEQ ID NO 15
<211> LENGTH: 922
<212> TYPE: DNA
<213> ORGANISM: Pan troglodytes
<220> FEATURE:
<221> NAME/KEY: misc_feature
<222> LOCATION: (122)..(922)
<223> OTHER INFORMATION: Active granzyme B

<400> SEQUENCE: 15

| | | |
|---|---|---|
| ccaagagcta aaagagagca aggagaaaac aacagcagct ccaaccaggg cagccttcct | 60 |
| gagaagatgc aaccaatcct gcttctgctg gccttcctcc tgctgcccag ggcagatgca | 120 |
| ggggagatca tcggcggaca tgaggccaag ccccactccc gcccctacat ggcttatctt | 180 |
| atgatctggg atcagaagac tctgaagagg tgcggtggct tcctgatacg agaggacttc | 240 |
| gtgctgacag ctgctcactg ttggggaagc tccataaatg tcaccttggg ggcccacaat | 300 |
| atcaaggaac aggagccgac ccagcagttt atccctgtga aaagacccat cccccatcca | 360 |
| gcctataatc ctaagaacta ctccaacgac atcatgctac tgcagctgga gagaaaggcc | 420 |
| aagcggacca gagctgtgca gcccctcagg ctacctagca caaggcccca ggtgaagcca | 480 |
| gggcaggtgt gcagtgtggc cggctggggg cagacggccc ccctgggaaa acactcacac | 540 |
| acactacaag aggtgaagat gacagtgcag gaagatcgaa agtgcgaatc tgacttacgc | 600 |
| cattattatg acagtaccat tgagttgtgc gtggggacc cagagattaa aaagacttcc | 660 |
| tttaagggggg actctggagg ccctcttgtg tgtaacaagg tggcccaggg cattgtctcc | 720 |
| tatggacgaa acaatggcat gcctccacga gcctgcacca agtctcaag ctttgtacac | 780 |
| tggataaaga aaccatgaa acgccactaa ctacaggaag caaactaagc ccccgctgtg | 840 |
| atgaaacacc ttctctggag ccaagccaga tttacactgg gagaggtgcc agcaactgaa | 900 |
| taaataccctc ttagctgagt gg | 922 |

<210> SEQ ID NO 16
<211> LENGTH: 247
<212> TYPE: PRT
<213> ORGANISM: Pan troglodytes
<220> FEATURE:
<221> NAME/KEY: misc_feature
<222> LOCATION: (21)..(247)
<223> OTHER INFORMATION: Active granzyme B

<400> SEQUENCE: 16

Met Gln Pro Ile Leu Leu Leu Leu Ala Phe Leu Leu Leu Pro Arg Ala
1               5                   10                  15

Asp Ala Gly Glu Ile Ile Gly Gly His Glu Ala Lys Pro His Ser Arg
                20                  25                  30

Pro Tyr Met Ala Tyr Leu Met Ile Trp Asp Gln Lys Thr Leu Lys Arg
            35                  40                  45

Cys Gly Gly Phe Leu Ile Arg Glu Asp Phe Val Leu Thr Ala Ala His
        50                  55                  60

Cys Trp Gly Ser Ser Ile Asn Val Thr Leu Gly Ala His Asn Ile Lys
65                  70                  75                  80

Glu Gln Glu Pro Thr Gln Gln Phe Ile Pro Val Lys Arg Pro Ile Pro
                85                  90                  95

His Pro Ala Tyr Asn Pro Lys Asn Tyr Ser Asn Asp Ile Met Leu Leu
            100                 105                 110

```
Gln Leu Glu Arg Lys Ala Lys Arg Thr Arg Ala Val Gln Pro Leu Arg
            115                 120                 125
Leu Pro Ser Asn Lys Ala Gln Val Lys Pro Gly Gln Val Cys Ser Val
        130                 135                 140
Ala Gly Trp Gly Gln Thr Ala Pro Leu Gly Lys His Ser His Thr Leu
145                 150                 155                 160
Gln Glu Val Lys Met Thr Val Gln Glu Asp Arg Lys Cys Glu Ser Asp
                165                 170                 175
Leu Arg His Tyr Tyr Asp Ser Thr Ile Glu Leu Cys Val Gly Asp Pro
            180                 185                 190
Glu Ile Lys Lys Thr Ser Phe Lys Gly Asp Ser Gly Gly Pro Leu Val
        195                 200                 205
Cys Asn Lys Val Ala Gln Gly Ile Val Ser Tyr Gly Arg Asn Asn Gly
    210                 215                 220
Met Pro Pro Arg Ala Cys Thr Lys Val Ser Ser Phe Val His Trp Ile
225                 230                 235                 240
Lys Lys Thr Met Lys Arg His
                245
```

<210> SEQ ID NO 17
<211> LENGTH: 669
<212> TYPE: DNA
<213> ORGANISM: Danio renio
<220> FEATURE:
<221> NAME/KEY: misc_feature
<222> LOCATION: (135)..(669)
<223> OTHER INFORMATION: Active Granzyme B

<400> SEQUENCE: 17

```
atagtaaacg gcagtgtagc aaaacctcac tccagacctt acatggtttc tgttcagctg      60
gatggtcaac atatctgcgg tggattcctc attactgaag agtttgtctt gactgctgca     120
cattgctgga atggagaaga aaatctgacg gttgtggttg gtgctcacga cttaagacaa     180
agtatggctt cagatcgcat agaagtggag tcttacatcc gccatccaag ctataactca     240
aaatttattt ggaatgacat catggttttt aagatagata aaaaggtcaa actgaacaac     300
aagattaaac cgatatcatt gccaagtgat ggtgaacata ttaaagcagg tgctgactgt     360
agtgttgccg ctggggagat tttgtggatg aaaggcccac tgagtgaccg tctaatggaa     420
gcaaacgtga ctacaaaaag tgacaaatac tgccaagata atgggatcc taaatatgtg     480
cccaaacata tgatctgtgt ttatgggcaa ggtggatcct gcaaagggga ttcaggaggt     540
cctttggttt gtggaaacac tgcagttggt gtcacatcct ttggtgatgc aagggtttgc     600
gatagtcctg aacaaccaga agtttataca aggatttcag catatcgcgt atggatccaa     660
tccataatt                                                             669
```

<210> SEQ ID NO 18
<211> LENGTH: 223
<212> TYPE: PRT
<213> ORGANISM: Danio renio

<400> SEQUENCE: 18

```
Ile Val Asn Gly Ser Val Ala Lys Pro His Ser Arg Pro Tyr Met Val
1               5                   10                  15
Ser Val Gln Leu Asp Gly Gln His Ile Cys Gly Gly Phe Leu Ile Thr
            20                  25                  30
Glu Glu Phe Val Leu Thr Ala Ala His Cys Trp Asn Gly Glu Glu Asn
        35                  40                  45
```

Leu Thr Val Val Val Gly Ala His Asp Leu Arg Gln Ser Met Ala Ser
 50                  55                  60

Asp Arg Ile Glu Val Glu Ser Tyr Ile Arg His Pro Ser Tyr Asn Ser
 65                  70                  75                  80

Lys Phe Ile Trp Asn Asp Ile Met Val Phe Lys Ile Asp Lys Lys Val
                 85                  90                  95

Lys Leu Asn Asn Lys Ile Lys Pro Ile Ser Leu Pro Ser Asp Gly Glu
            100                 105                 110

His Ile Lys Ala Gly Ala Asp Cys Ser Val Ala Gly Trp Gly Asp Leu
        115                 120                 125

Trp Met Lys Gly Pro Leu Ser Asp Arg Leu Met Glu Ala Asn Val Thr
130                 135                 140

Thr Lys Ser Asp Lys Tyr Cys Gln Asp Lys Trp Gly Ser Lys Tyr Val
145                 150                 155                 160

Pro Lys His Met Ile Cys Val Tyr Gly Gln Gly Ser Cys Lys Gly
                165                 170                 175

Asp Ser Gly Gly Pro Leu Val Cys Gly Asn Thr Ala Val Gly Val Thr
            180                 185                 190

Ser Phe Gly Asp Ala Arg Val Cys Asp Ser Pro Glu Gln Pro Glu Val
        195                 200                 205

Tyr Thr Arg Ile Ser Ala Tyr Arg Val Trp Gln Ser Ile Ile
210                 215                 220

<210> SEQ ID NO 19
<211> LENGTH: 678
<212> TYPE: DNA
<213> ORGANISM: Gallus gallus
<220> FEATURE:
<221> NAME/KEY: misc_feature
<222> LOCATION: (138)..(678)
<223> OTHER INFORMATION: Active Granzyme B

<400> SEQUENCE: 19
ggtcagatca tcgggggcca cgaggccaag ccccactccc acccctacat ggcgtacctg      60
aagttgagga tgtctgcctg cggaggattc ctggtggccc tgattgggt gatgacggcc     120
gcacactgct tgggggaaa catcaccgtc atcctggggg ctcacgatat ctacgaacca     180
gagcagagcc agcaggtccg agggtcctc aaatactacc cacacccgc ttcccaccgg     240
ccttcccctc tgtcctccac ccactctgct cacagtcctc ctctttccca gctgacagcg     300
aaggtcaagc tcaacaaata cgtccgcacc attgcgctgc ccaaaaccag cagcgacctc     360
cccacgggca cctcgtgcac catagcagga tggggcctga ttgatgagga cgagagaacc     420
agcaaaactct tcgaaaccga agtctccatc tacagccgca gaaaatgcat tctgttctac     480
ccacacctcg acaacggcat ggtgtgcgcc ggcagcttcc atgagatgaa ggactccagc     540
cagggtgatt ccggagggcc gctggtgtgc aataaggtag cacagggtgt tgtttccttc     600
gggtacgaca gcccgcctgg tgtctatgct cgcattgcca actacctacc ctggatcaag     660
aaagtcatga agaagtaa                                                   678

<210> SEQ ID NO 20
<211> LENGTH: 225
<212> TYPE: PRT
<213> ORGANISM: Gallus gallus
<220> FEATURE:
<221> NAME/KEY: misc_feature
<222> LOCATION: (3)..(225)
<223> OTHER INFORMATION: Active Granzyme B

<400> SEQUENCE: 20

```
Gly Gln Ile Ile Gly Gly His Glu Ala Lys Pro His Ser His Pro Tyr
1               5                   10                  15
Met Ala Tyr Leu Lys Leu Arg Met Ser Ala Cys Gly Gly Phe Leu Val
            20                  25                  30
Ala Pro Asp Trp Val Met Thr Ala Ala His Cys Leu Gly Gly Asn Ile
        35                  40                  45
Thr Val Ile Leu Gly Ala His Asp Ile Tyr Glu Pro Glu Gln Ser Gln
    50                  55                  60
Gln Val Arg Gly Val Leu Lys Tyr Tyr Pro His Pro Ala Ser His Arg
65                  70                  75                  80
Pro Ser Pro Leu Ser Ser Thr His Ser Ala His Ser Pro Pro Leu Ser
                85                  90                  95
Gln Leu Thr Ala Lys Val Lys Leu Asn Lys Tyr Val Arg Thr Ile Ala
            100                 105                 110
Leu Pro Lys Thr Ser Ser Asp Leu Pro Thr Gly Thr Ser Cys Thr Ile
        115                 120                 125
Ala Gly Trp Gly Leu Ile Asp Glu Asp Glu Arg Thr Ser Lys Leu Phe
    130                 135                 140
Glu Thr Glu Val Ser Ile Tyr Ser Arg Arg Lys Cys Ile Leu Phe Tyr
145                 150                 155                 160
Pro His Leu Asp Asn Gly Met Val Cys Ala Gly Ser Phe His Glu Met
                165                 170                 175
Lys Asp Ser Ser Gln Gly Asp Ser Gly Gly Pro Leu Val Cys Asn Lys
            180                 185                 190
Val Ala Gln Gly Val Val Ser Phe Gly Tyr Asp Ser Pro Pro Gly Val
        195                 200                 205
Tyr Ala Arg Ile Ala Asn Tyr Leu Pro Trp Ile Lys Lys Val Met Lys
    210                 215                 220
Lys
225
```

```
<210> SEQ ID NO 21
<211> LENGTH: 735
<212> TYPE: DNA
<213> ORGANISM: Fugu rubipres
<220> FEATURE:
<221> NAME/KEY: misc_feature
<222> LOCATION: (182)..(735)
<223> OTHER INFORMATION: Active Granzyme B
```

<400> SEQUENCE: 21

```
gtcttgcttc cttttggttt tgcttctccc gaaggggcgt ctgacagcgg catcgtgggt      60
gggaaagagg cgaagcctca ttccagaccc tacatggctt cactgcaggt tgagaaagaa     120
cacacctgtg gagggatact cattcgccag gactttgtcc tcacctctgc acactgcaaa     180
cacgccggga tgacagtggt cctcggagct acaatatca gcaggcagga ggccagccag     240
cagaggatgg aggtggccga gttcatccct caccccaat acaccggaga gtacgattat     300
gatgtcatgc tgctgaagct caaacgtgtg gcggtgctga caagtacgt gagacccatc     360
gaactcctga agaaaggcgg gagcaatcga gcgcaccttc gctgcaccgt ggttgggtgg     420
gggcggactg gagaggacct gcccgcctcc aagtgctga aggaggccac cgagcagacg     480
cagttcgact cgagtgcaa aaatatttgg cagcagtatt ttaatggaac acaaatgatt     540
tgcaccaat ttgacagaaa gaaggggga gtttgccagg gagactccgg cggaccgctg     600
ctctgcaaca acaagcttcg ggggttaatg gcgttcacct acaggacaa gtgcagccat     660
```

```
gccaggtatc tcacgtctt catgaaagtc tccttctttg tcccgtggat tcagagcgtg      720
atgcagaggt tctag                                                      735
```

```
<210> SEQ ID NO 22
<211> LENGTH: 244
<212> TYPE: PRT
<213> ORGANISM: Fugu rubipres

<400> SEQUENCE: 22

Val Leu Leu Pro Phe Gly Phe Ala Ser Pro Glu Gly Ala Ser Asp Ser
1               5                   10                  15

Gly Ile Val Gly Gly Lys Glu Ala Lys Pro His Ser Arg Pro Tyr Met
            20                  25                  30

Ala Ser Leu Gln Val Glu Lys Glu His Thr Cys Gly Gly Ile Leu Ile
        35                  40                  45

Arg Gln Asp Phe Val Leu Thr Ser Ala His Cys Lys His Ala Gly Met
    50                  55                  60

Thr Val Val Leu Gly Ala His Asn Ile Ser Arg Gln Glu Ala Ser Gln
65                  70                  75                  80

Gln Arg Met Glu Val Ala Glu Phe Ile Pro His Pro Gln Tyr Thr Gly
                85                  90                  95

Glu Tyr Asp Tyr Asp Val Met Leu Leu Lys Leu Lys Arg Val Ala Val
            100                 105                 110

Leu Asn Lys Tyr Val Arg Pro Ile Glu Leu Leu Lys Lys Gly Gly Ser
        115                 120                 125

Asn Arg Ala His Leu Arg Cys Thr Val Val Gly Trp Gly Arg Thr Gly
    130                 135                 140

Glu Asp Leu Pro Ala Ser Lys Val Leu Lys Glu Ala Thr Glu Gln Thr
145                 150                 155                 160

Gln Phe Asp Phe Glu Cys Lys Asn Ile Trp Gln Gln Tyr Phe Asn Gly
                165                 170                 175

Thr Gln Met Ile Cys Thr Lys Phe Asp Arg Lys Lys Gly Gly Val Cys
            180                 185                 190

Gln Gly Asp Ser Gly Gly Pro Leu Leu Cys Asn Asn Lys Leu Arg Gly
        195                 200                 205

Leu Met Ala Phe Thr Tyr Arg Asp Lys Cys Ser His Ala Arg Tyr Pro
    210                 215                 220

His Val Phe Met Lys Val Ser Phe Phe Val Pro Trp Ile Gln Ser Val
225                 230                 235                 240

Met Gln Arg Phe

<210> SEQ ID NO 23
<211> LENGTH: 884
<212> TYPE: DNA
<213> ORGANISM: Homo sapiens
<220> FEATURE:
<221> NAME/KEY: misc_feature
<223> OTHER INFORMATION: Granzyme A

<400> SEQUENCE: 23
cagccacaat gaggaactcc tatagatttc tggcatcctc tctctcagtt gtcgtttctc      60
tcctgctaat tcctgaagat gtctgtgaaa aaattattgg aggaaatgaa gtaactcctc     120
attcaagacc ctacatggtc ctacttagtc ttgacagaaa aaccatctgt gctgggcctt     180
tgattgcaaa agactgggtg ttgactgcag ctcactgtaa cttgaacaaa ggtcccagg      240 tcattcttgg ggctcactca ataaccaggg aagagccaac aaaacagata atgcttgtta     300
```

```
agaaagagtt tccctatcca tgctatgacc cagccacacg cgaaggtgac cttaaacttt    360
tacagctgac ggaaaaagca aaattaaca aatatgtgac tatccttcat ctacctaaaa     420
agggggatga tgtgaaacca ggaaccatgt gccaagttgc agggtggggc aggactcaca    480
atagtgcatc ttggtccgat actctgagag aagtcaatat caccatcata gacagaaaag    540
tctgcaatga tcgaaatcac tataatttta accctgtgat tggaatgaat atggtttgtg    600
ctggaagcct ccgaggtgga agagactcgt gcaatggaga ttctggaagc cctttgttgt    660 gcgaggtgt tttccgaggg gtcacttcct ttggccttga aaataaatgc ggagaccctc     720
gtgggcctgg tgtctatatt cttctctcaa agaaacacct caactggata attatgacta    780
tcaagggagc agtttaaata accgtttcct ttcatttact gtggcttctt aatcttttca    840
caaataaaat caatttgcat gactgtaaaa aaaaaaaaa aaaa                      884
```

<210> SEQ ID NO 24
<211> LENGTH: 262
<212> TYPE: PRT
<213> ORGANISM: Homo sapiens
<220> FEATURE:
<221> NAME/KEY: misc_feature
<223> OTHER INFORMATION: Granzyme A

<400> SEQUENCE: 24

```
Met Arg Asn Ser Tyr Arg Phe Leu Ala Ser Ser Leu Ser Val Val Val
1               5                   10                  15

Ser Leu Leu Leu Ile Pro Glu Asp Val Cys Glu Lys Ile Ile Gly Gly
            20                  25                  30

Asn Glu Val Thr Pro His Ser Arg Pro Tyr Met Val Leu Leu Ser Leu
        35                  40                  45

Asp Arg Lys Thr Ile Cys Ala Gly Ala Leu Ile Ala Lys Asp Trp Val
    50                  55                  60

Leu Thr Ala Ala His Cys Asn Leu Asn Lys Arg Ser Gln Val Ile Leu
65                  70                  75                  80

Gly Ala His Ser Ile Thr Arg Glu Glu Pro Thr Lys Gln Ile Met Leu
                85                  90                  95

Val Lys Lys Glu Phe Pro Tyr Pro Cys Tyr Asp Pro Ala Thr Arg Glu
            100                 105                 110

Gly Asp Leu Lys Leu Leu Gln Leu Thr Glu Lys Ala Lys Ile Asn Lys
        115                 120                 125

Tyr Val Thr Ile Leu His Leu Pro Lys Lys Gly Asp Asp Val Lys Pro
    130                 135                 140

Gly Thr Met Cys Gln Val Ala Gly Trp Gly Arg Thr His Asn Ser Ala
145                 150                 155                 160

Ser Trp Ser Asp Thr Leu Arg Glu Val Asn Ile Thr Ile Ile Asp Arg
                165                 170                 175

Lys Val Cys Asn Asp Arg Asn His Tyr Asn Phe Asn Pro Val Ile Gly
            180                 185                 190

Met Asn Met Val Cys Ala Gly Ser Leu Arg Gly Gly Arg Asp Ser Cys
        195                 200                 205

Asn Gly Asp Ser Gly Ser Pro Leu Leu Cys Glu Gly Val Phe Arg Gly
    210                 215                 220

Val Thr Ser Phe Gly Leu Glu Asn Lys Cys Gly Asp Pro Arg Gly Pro
225                 230                 235                 240

Gly Val Tyr Ile Leu Leu Ser Lys Lys His Leu Asn Trp Ile Ile Met
                245                 250                 255
```

Thr Ile Lys Gly Ala Val
        260

<210> SEQ ID NO 25
<211> LENGTH: 894
<212> TYPE: DNA
<213> ORGANISM: Mus musculus
<220> FEATURE:
<221> NAME/KEY: misc_feature
<223> OTHER INFORMATION: Granzyme C

<400> SEQUENCE: 25

```
cacacctcct tcctcccctt ccaagggctt tgtctactct gccctcctcc atcctgagca      60
gccttcctgg gaagatgcca ccagtcctga ttctcctgac cctacttctg cctctcagag     120
ctggagcaga ggagataatc ggaggcaatg agatcagtcc acattcccgt ccctacatgg     180
catattatga gtttctgaaa gttggtggga agaagatgtt ctgcggaggc ttcctggttc     240
gagacaaatt cgtgctaaca gctgctcact gcaaaggacg ctcaatgaca gtcacactgg     300
gggctcacaa catcaaggct aaggaggaga cacagcagat catccctgtg gcaaaagcca     360
ttccccatcc agactataat cctgatgacc gttctaatga catcatgcta ttaaagctgg     420
tgagaaatgc caagaggact agagctgtga ggcccctcaa cctgcccagg cgcaatgctc     480
atgtgaagcc aggggatgag tgctatgtgg ctggttgggg aaaggtaacc ccggacgggg     540
aattcccaaa aacactgcac gaagttaagc tgacagtaca gaaggatcag gtgtgtgagt     600
cccagttcca agttcttac aacagagcta atgagatatg tgtgggagac tcaaagatca     660
agggagcttc ctttgaggag gattctggag gcccgcttgt gtgtaaaaga gcagctgcag     720
gcatcgtctc ctacgggcaa actgatggat cagctccaca gtcttcaca agagttttga     780
gttttgtatc gtggataaag aaaacgatga acacagcta actacaagaa gcaaactaga     840
tcctgatctg accagccatc ttccccatag ctgagtccag gattgctcta ggac           894
```

<210> SEQ ID NO 26
<211> LENGTH: 248
<212> TYPE: PRT
<213> ORGANISM: Mus musculus
<220> FEATURE:
<221> NAME/KEY: misc_feature
<223> OTHER INFORMATION: Granzyme C

<400> SEQUENCE: 26

Met Pro Pro Val Leu Ile Leu Leu Thr Leu Leu Pro Leu Arg Ala
1               5                   10                  15

Gly Ala Glu Glu Ile Ile Gly Gly Asn Glu Ile Ser Pro His Ser Arg
            20                  25                  30

Pro Tyr Met Ala Tyr Tyr Glu Phe Leu Lys Val Gly Gly Lys Lys Met
        35                  40                  45

Phe Cys Gly Gly Phe Leu Val Arg Asp Lys Phe Val Leu Thr Ala Ala
    50                  55                  60

His Cys Lys Gly Arg Ser Met Thr Val Thr Leu Gly Ala His Asn Ile
65                  70                  75                  80

Lys Ala Lys Glu Glu Thr Gln Gln Ile Ile Pro Val Ala Lys Ala Ile
                85                  90                  95

Pro His Pro Asp Tyr Asn Pro Asp Asp Arg Ser Asn Asp Ile Met Leu
            100                 105                 110

Leu Lys Leu Val Arg Asn Ala Lys Arg Thr Arg Ala Val Arg Pro Leu
        115                 120                 125

Asn Leu Pro Arg Arg Asn Ala His Val Lys Pro Gly Asp Glu Cys Tyr

```
              130                 135                 140
Val Ala Gly Trp Gly Lys Val Thr Pro Asp Gly Glu Phe Pro Lys Thr
145                 150                 155                 160

Leu His Glu Val Lys Leu Thr Val Gln Lys Asp Gln Val Cys Glu Ser
                165                 170                 175

Gln Phe Gln Ser Ser Tyr Asn Arg Ala Asn Glu Ile Cys Val Gly Asp
            180                 185                 190

Ser Lys Ile Lys Gly Ala Ser Phe Glu Glu Asp Ser Gly Gly Pro Leu
        195                 200                 205

Val Cys Lys Arg Ala Ala Ala Gly Ile Val Ser Tyr Gly Gln Thr Asp
    210                 215                 220

Gly Ser Ala Pro Gln Val Phe Thr Arg Val Leu Ser Phe Val Ser Trp
225                 230                 235                 240

Ile Lys Lys Thr Met Lys His Ser
                245

<210> SEQ ID NO 27
<211> LENGTH: 842
<212> TYPE: DNA
<213> ORGANISM: Mus musculus
<220> FEATURE:
<221> NAME/KEY: misc_feature
<223> OTHER INFORMATION: Granzyme D

<400> SEQUENCE: 27
atgccaccaa tcctgattct cctgacccta cttctgcctc tcagagctgg agcagaggag      60
atcatcggcg gccatgtggt gaagccacac tcccgcccct acatggcatt cgttatgtct     120
gtggatatta aggggaacag gatatactgt ggaggcttcc tgattcaaga tgactttgtg     180
ctgacggctg ctcactgcaa aaacagctca atgacagtca cactgggggc ccacaacatc     240
acggctaagg aggagacaca gcagatcatc cctgtggcaa agacattcc ccatccagat      300 tataatgcta ctatcttcta cagtgacatc atgctgttaa agctggagag taaggccaag     360
agaactaaag ctgtgagacc cctcaagttg cccagatcca atgcccgggt gaagccaggg     420
gatgtgtgca gtgtggctgg ctgggggtca aggtccatca atgacactaa gcatctgcc      480 cgcctgcgag aggttcaact ggtcatccag gaggacgagg aatgcaaaaa acgtttccga     540
tactacactg agaccacaga gatttgtgct ggagacttga gaaaataaa gactcctttc      600 aagggtgact cggggggacc ccttgtgtgt cacaaccaag catatggact tttcgcctat     660
gcaaaaaacg gaacaatctc ttcaggaatc ttcactaagg ttgtgcactt cctgccgtgg     720
ataagctgga acatgaagtt gctctaacag gagttaaacc acccgtgcct gaccagcctg     780
tccgacctca ggcaagaacc atgtggagtg ggcagcaaag aatgaaaatt cacaataaat     840
aa                                                                   842

<210> SEQ ID NO 28
<211> LENGTH: 248
<212> TYPE: PRT
<213> ORGANISM: Mus musculus
<220> FEATURE:
<221> NAME/KEY: misc_feature
<223> OTHER INFORMATION: Granzyme D

<400> SEQUENCE: 28

Met Pro Pro Ile Leu Ile Leu Leu Thr Leu Leu Leu Pro Leu Arg Ala
1               5                  10                  15

Gly Ala Glu Glu Ile Ile Gly Gly His Val Val Lys Pro His Ser Arg
            20                  25                  30
```

Pro Tyr Met Ala Phe Val Met Ser Val Asp Ile Lys Gly Asn Arg Ile
            35                  40                  45

Tyr Cys Gly Gly Phe Leu Ile Gln Asp Asp Phe Val Leu Thr Ala Ala
        50                  55                  60

His Cys Lys Asn Ser Ser Met Thr Val Thr Leu Gly Ala His Asn Ile
65                  70                  75                  80

Thr Ala Lys Glu Glu Thr Gln Gln Ile Ile Pro Val Ala Lys Asp Ile
                85                  90                  95

Pro His Pro Asp Tyr Asn Ala Thr Ile Phe Tyr Ser Asp Ile Met Leu
            100                 105                 110

Leu Lys Leu Glu Ser Lys Ala Lys Arg Thr Lys Ala Val Arg Pro Leu
        115                 120                 125

Lys Leu Pro Arg Ser Asn Ala Arg Val Lys Pro Gly Asp Val Cys Ser
    130                 135                 140

Val Ala Gly Trp Gly Ser Arg Ser Ile Asn Asp Thr Lys Ala Ser Ala
145                 150                 155                 160

Arg Leu Arg Glu Val Gln Leu Val Ile Gln Glu Asp Glu Cys Lys
                165                 170                 175

Lys Arg Phe Arg Tyr Tyr Thr Glu Thr Glu Ile Cys Ala Gly Asp
            180                 185                 190

Leu Lys Lys Ile Lys Thr Pro Phe Lys Gly Asp Ser Gly Gly Pro Leu
        195                 200                 205

Val Cys His Asn Gln Ala Tyr Gly Leu Phe Ala Tyr Ala Lys Asn Gly
    210                 215                 220

Thr Ile Ser Ser Gly Ile Phe Thr Lys Val Val His Phe Leu Pro Trp
225                 230                 235                 240

Ile Ser Trp Asn Met Lys Leu Leu
                245

<210> SEQ ID NO 29
<211> LENGTH: 1018
<212> TYPE: DNA
<213> ORGANISM: Mus musculus
<220> FEATURE:
<221> NAME/KEY: misc_feature
<223> OTHER INFORMATION: Granzyme E

<400> SEQUENCE: 29

```
ggtcatcctg ggcctggagc agcaggtgcg aggtaggctg cgccgccccg tcttgttcat     60
cctgctggcc aggggcagcc tccgcacagc cccgcccctc cttcctcccc ttccaagggc    120
tttgtctcct ttgctctcct tcaactgagc agccttcctg ggaagatgcc accagtcctg    180
attctcctga ccctacttct gcctcttgga gctggagcag aggagatcat cggcggccat    240
gtggtgaagc cacactcccg cccctacatg gcgtttgtta agtctgtgga tattgaaggt    300
aataggagat actgtggagg cttcttggtt caagatgact ttgtgctgac tgctgctcac    360
tgcaggaaca ggacaatgac agtcacactg ggggcccaca acatcaaggc taaggaggag    420
acacagcaga tcatccctgt ggcaaaagcc attccccatc cagattataa tgccactgcc    480
ttcttcagtg acatcatgct gttaaagctg gagagtaagg ccaagagaac taaagctgtg    540
agacccctca gttgcccag acccaatgcc cgggtgaagc cagggatgt gtgcagtgtg     600
gctggctggg ggtcaaggtc catcaatgac actaaagcat ctgcccgcct gcgagaggct    660
caactggtca tccaggagga tgaggaatgc aaaaaacgtt tccgacacta cactgagacc    720
acagagattt gtgctggaga cttgaagaaa ataaagactc ctttcaaggg tgactctggg    780
```

```
ggaccoctcg tgtgtgacaa caaagcttat ggacttttag cctatgcaaa aaacaggaca    840
atctcttcag gagtcttcac taagattgtg cacttcctgc cgtggataag caggaacatg    900
aagctgctct aacagtgtta aaccaccogt gcctgaccag cctgtccgac ctcaggcaag    960
aaccacgtgg agtgggcagc aaagaatgaa aattcacaat aaataacctc cagactgc     1018
```

<210> SEQ ID NO 30
<211> LENGTH: 248
<212> TYPE: PRT
<213> ORGANISM: Mus musculus
<220> FEATURE:
<221> NAME/KEY: misc_feature
<223> OTHER INFORMATION: Granzyme E

<400> SEQUENCE: 30

```
Met Pro Pro Val Leu Ile Leu Leu Thr Leu Leu Leu Pro Leu Gly Ala
1               5                   10                  15

Gly Ala Glu Glu Ile Ile Gly Gly His Val Val Lys Pro His Ser Arg
            20                  25                  30

Pro Tyr Met Ala Phe Val Lys Ser Val Asp Ile Glu Gly Asn Arg Arg
        35                  40                  45

Tyr Cys Gly Gly Phe Leu Val Gln Asp Asp Phe Val Leu Thr Ala Ala
    50                  55                  60

His Cys Arg Asn Arg Thr Met Thr Val Thr Leu Gly Ala His Asn Ile
65                  70                  75                  80

Lys Ala Lys Glu Glu Thr Gln Gln Ile Ile Pro Val Ala Lys Ala Ile
                85                  90                  95

Pro His Pro Asp Tyr Asn Ala Thr Ala Phe Phe Ser Asp Ile Met Leu
            100                 105                 110

Leu Lys Leu Glu Ser Lys Ala Lys Arg Thr Lys Ala Val Arg Pro Leu
        115                 120                 125

Lys Leu Pro Arg Pro Asn Ala Arg Val Lys Pro Gly Asp Val Cys Ser
    130                 135                 140

Val Ala Gly Trp Gly Ser Arg Ser Ile Asn Asp Thr Lys Ala Ser Ala
145                 150                 155                 160

Arg Leu Arg Glu Ala Gln Leu Val Ile Gln Glu Asp Glu Glu Cys Lys
                165                 170                 175

Lys Arg Phe Arg His Tyr Thr Glu Thr Thr Glu Ile Cys Ala Gly Asp
            180                 185                 190

Leu Lys Lys Ile Lys Thr Pro Phe Lys Gly Asp Ser Gly Gly Pro Leu
        195                 200                 205

Val Cys Asp Asn Lys Ala Tyr Gly Leu Leu Ala Tyr Ala Lys Asn Arg
    210                 215                 220

Thr Ile Ser Ser Gly Val Phe Thr Lys Ile Val His Phe Leu Pro Trp
225                 230                 235                 240

Ile Ser Arg Asn Met Lys Leu Leu
                245
```

<210> SEQ ID NO 31
<211> LENGTH: 1027
<212> TYPE: DNA
<213> ORGANISM: Mus musculus
<220> FEATURE:
<221> NAME/KEY: misc_feature
<223> OTHER INFORMATION: Granzyme F

<400> SEQUENCE: 31

```
gccttctgct ccagtgccac cctgatgcag gcctcctgag aacttttccg atgcttccct    60
```

```
ctctccttgg gccacacccg ctctctacag acctccttcc tccccttcca agggctttgt    120
ctactctgcc ctcctccatc ctgagcagtc ctttattcag atgccaccaa tcctgattct    180
cctgacccct cttctgcctc tcagagctgg agcagaggag atcatcgggg ccatgaggt    240 caagccccac tcccgccctt acatggcacg tgtgaggttt gtgaaagata atggaaaaag    300
acattcctgt ggaggcttcc tggttcaaga ctactttgtg ctgacggctg ctcactgcac    360
tggaagctca atgagagtca tactgggggc ccacaacatc agggctaagg aagagacaca    420
gcagatcatc cctgtggcaa agccattcc ccacccagct tatgatgata aggacaacac    480
cagtgacatc atgctattaa agctggagag taaggccaag agaactaaag ctgtgaggcc    540
cctcaagttg cccagaccca atgcccgggt gaagccaggg catgtttgca gtgtggctgg    600
ctgggggaga acatccatca atgcaacaca aagatcttcc tgcctacgag aggctcaact    660
gatcatccag aaggataagg aatgcaaaaa atacttctat aagtatttca agaccatgca    720
gatttgtgct ggagacccaa agaaaataca gtctacttac agtggtgact ccggggggacc    780 cctcgtgtgt aacaacaaag cttatggagt tttaacctat gggctaaaca ggacaatcgg    840
tccaggagtc ttcactaagg ttgtgcacta cctgccgtgg ataagcagga acatgaagct    900
gctctaacag gagttaaacc acccgtgcct gaccagcctg tccgacctca ggcaagaacc    960
atgtggagtg agcagcaaag aatgaaaatt cataataaat aacctccaga gtgcatagag   1020
ctgaaaa                                                              1027
```

<210> SEQ ID NO 32
<211> LENGTH: 248
<212> TYPE: PRT
<213> ORGANISM: Mus musculus
<220> FEATURE:
<221> NAME/KEY: misc_feature
<223> OTHER INFORMATION: Granzyme F

<400> SEQUENCE: 32

```
Met Pro Pro Ile Leu Ile Leu Leu Thr Leu Leu Pro Leu Arg Ala
1               5                   10                  15

Gly Ala Glu Glu Ile Ile Gly Gly His Glu Val Lys Pro His Ser Arg
            20                  25                  30

Pro Tyr Met Ala Arg Val Arg Phe Val Lys Asp Asn Gly Lys Arg His
        35                  40                  45

Ser Cys Gly Gly Phe Leu Val Gln Asp Tyr Phe Val Leu Thr Ala Ala
    50                  55                  60

His Cys Thr Gly Ser Ser Met Arg Val Ile Leu Gly Ala His Asn Ile
65                  70                  75                  80

Arg Ala Lys Glu Glu Thr Gln Gln Ile Ile Pro Val Ala Lys Ala Ile
                85                  90                  95

Pro His Pro Ala Tyr Asp Asp Lys Asp Asn Thr Ser Asp Ile Met Leu
            100                 105                 110

Leu Lys Leu Glu Ser Lys Ala Lys Arg Thr Lys Ala Val Arg Pro Leu
        115                 120                 125

Lys Leu Pro Arg Pro Asn Ala Arg Val Lys Pro Gly His Val Cys Ser
    130                 135                 140

Val Ala Gly Trp Gly Arg Thr Ser Ile Asn Ala Thr Gln Arg Ser Ser
145                 150                 155                 160

Cys Leu Arg Glu Ala Gln Leu Ile Ile Gln Lys Asp Lys Glu Cys Lys
                165                 170                 175

Lys Tyr Phe Tyr Lys Tyr Phe Lys Thr Met Gln Ile Cys Ala Gly Asp
            180                 185                 190
```

```
Pro Lys Lys Ile Gln Ser Thr Tyr Ser Gly Asp Ser Gly Pro Leu
        195                 200                 205

Val Cys Asn Asn Lys Ala Tyr Gly Val Leu Thr Tyr Gly Leu Asn Arg
        210                 215                 220

Thr Ile Gly Pro Gly Val Phe Thr Lys Val Val His Tyr Leu Pro Trp
225                 230                 235                 240

Ile Ser Arg Asn Met Lys Leu Leu
                245

<210> SEQ ID NO 33
<211> LENGTH: 799
<212> TYPE: DNA
<213> ORGANISM: Mus musculus
<220> FEATURE:
<221> NAME/KEY: misc_feature
<223> OTHER INFORMATION: Granzyme G

<400> SEQUENCE: 33
ctgctctgcc ctccttcatc ctgagcagcc ttcctgggaa gatgccacca atcctgattc      60
tcctgaccct acttctgcct ctcagagctg gagcagagga gatcatcggc ggccatgagg     120
tgaagccaca ctcccgcccc tacatggcgt tcattaagtc tgtggatatc gaagggaaga     180
agaaatactg cggaggcttc ttggttcaag atgattttgt gctgacggct gctcactgca     240
gaaacaggtc aatgacagtc acactggggg cccacaacat caaggctaag gaggagacac     300
agcagatcat ccctgtggca aaagccattc ccatccagc ttttaataga agcatggca      360 ccaatgacat tatgttatta aaactggaga gtaaggccaa gagaactaaa gctgtgaggc     420
ccctcaagtt gcccagaccc aatgccaggg tgaagccagg ggatgtgtgc agtgtggctg     480 gctggggaa acatccatc aatgccacta aagcatctgc ccgcctgcga gaggctcaac     540
tgatcatcca ggaggacgag gaatgcaaaa aactctggta cacctattcc aagaccacgc     600
agatctgtgc tggagaccca aaaaagtac aggctcctta cgagggtgaa tcggggggac     660
ccctcgtgtg tgacaaccta gcttatggag ttgtatccta tggaataaac aggacaatca     720
ctccaggagt cttcactaag gttgtgcact tcctgccgtg gataagcaca acatgaagc     780 tgctctaaca ggagttaaa                                                  799

<210> SEQ ID NO 34
<211> LENGTH: 248
<212> TYPE: PRT
<213> ORGANISM: Mus musculus
<220> FEATURE:
<221> NAME/KEY: misc_feature
<223> OTHER INFORMATION: Granzyme G

<400> SEQUENCE: 34

Met Pro Pro Ile Leu Ile Leu Leu Thr Leu Leu Pro Leu Arg Ala
1               5                   10                  15

Gly Ala Glu Glu Ile Ile Gly Gly His Glu Val Lys Pro His Ser Arg
            20                  25                  30

Pro Tyr Met Ala Phe Ile Lys Ser Val Asp Ile Glu Gly Lys Lys
        35                  40                  45

Tyr Cys Gly Gly Phe Leu Val Gln Asp Asp Phe Val Leu Thr Ala Ala
    50                  55                  60

His Cys Arg Asn Arg Ser Met Thr Val Thr Leu Gly Ala His Asn Ile
65                  70                  75                  80

Lys Ala Lys Glu Glu Thr Gln Gln Ile Ile Pro Val Ala Lys Ala Ile
                85                  90                  95
```

Pro His Pro Ala Phe Asn Arg Lys His Gly Thr Asn Asp Ile Met Leu
             100                 105                 110

Leu Lys Leu Glu Ser Lys Ala Lys Arg Thr Lys Ala Val Arg Pro Leu
         115                 120                 125

Lys Leu Pro Arg Pro Asn Ala Arg Val Lys Pro Gly Asp Val Cys Ser
130                 135                 140

Val Ala Gly Trp Gly Lys Thr Ser Ile Asn Ala Thr Lys Ala Ser Ala
145                 150                 155                 160

Arg Leu Arg Glu Ala Gln Leu Ile Ile Gln Glu Asp Glu Cys Lys
             165                 170                 175

Lys Leu Trp Tyr Thr Tyr Ser Lys Thr Thr Gln Ile Cys Ala Gly Asp
             180                 185                 190

Pro Lys Lys Val Gln Ala Pro Tyr Glu Gly Ser Gly Gly Pro Leu
         195                 200                 205

Val Cys Asp Asn Leu Ala Tyr Gly Val Val Ser Tyr Gly Ile Asn Arg
210                 215                 220

Thr Ile Thr Pro Gly Val Phe Thr Lys Val Val His Phe Leu Pro Trp
225                 230                 235                 240

Ile Ser Thr Asn Met Lys Leu Leu
             245

<210> SEQ ID NO 35
<211> LENGTH: 792
<212> TYPE: DNA
<213> ORGANISM: Mus musculus
<220> FEATURE:
<221> NAME/KEY: misc_feature
<223> OTHER INFORMATION: Granzyme K

<400> SEQUENCE: 35

```
atgaggtttt cttcatgggc tctggtttcc ctggtggctg cgtttatat gtcttcagag      60
tgtttccata ctgaaattat tggagggagg gaagtccagc cgcattccag gccatttatg    120
gcgtccatcc agtaccgcag caagcatatt tgtggaggag tcctgatcca cccacagtgg    180
gtgctaacag ccgcccactg ctactcttgg tttcccagag gccactctcc caccgtggtt    240
ttaggagcac attctctttc caagaatgag cccatgaagc agacatttga aattaaaaag    300
ttcatcccat tctcacgact tcagtccggt tccgcatcgc atgacatcat gctgataaag    360
cttcgcactg ctgcagaact aaacaagaat gtccaactgc ttcacctggg atccaaaaac    420
tatcttagag atgggaccaa atgccaggtg actggctggg gaaccaccaa gccagatctg    480
ttaaccgcct ctgataccct gagagaagtc actgttacca tcataagtag aaaacgctgt    540
aacagccaaa gctactacaa ccacaaacct gttataacca aggacatgat atgtgcagga    600
gatgccagag gtcaaaagga ttcctgcaag ggtgactctg gtggccctt gatctgcaaa     660
ggcatcttcc atgccctagt ctctcagggc tataaatgtg catcgccaa aaagcctgga     720
atctatacgc tattaactaa gaaataccag acctggatca aaagcaagct tgccccatca    780
cgtgcacatt ga                                                        792
```

<210> SEQ ID NO 36
<211> LENGTH: 263
<212> TYPE: PRT
<213> ORGANISM: Mus musculus
<220> FEATURE:
<221> NAME/KEY: misc_feature
<223> OTHER INFORMATION: Granzyme K

<400> SEQUENCE: 36

```
Met Arg Phe Ser Ser Trp Ala Leu Val Ser Leu Val Ala Gly Val Tyr
 1               5                  10                  15

Met Ser Ser Glu Cys Phe His Thr Glu Ile Ile Gly Gly Arg Glu Val
             20                  25                  30

Gln Pro His Ser Arg Pro Phe Met Ala Ser Ile Gln Tyr Arg Ser Lys
         35                  40                  45

His Ile Cys Gly Gly Val Leu Ile His Pro Gln Trp Val Leu Thr Ala
 50                  55                  60

Ala His Cys Tyr Ser Trp Phe Pro Arg Gly His Ser Pro Thr Val Val
 65              70                  75                  80

Leu Gly Ala His Ser Leu Ser Lys Asn Glu Pro Met Lys Gln Thr Phe
                 85                  90                  95

Glu Ile Lys Lys Phe Ile Pro Phe Ser Arg Leu Gln Ser Gly Ser Ala
             100                 105                 110

Ser His Asp Ile Met Leu Ile Lys Leu Arg Thr Ala Ala Glu Leu Asn
         115                 120                 125

Lys Asn Val Gln Leu Leu His Leu Gly Ser Lys Asn Tyr Leu Arg Asp
130                 135                 140

Gly Thr Lys Cys Gln Val Thr Gly Trp Gly Thr Thr Lys Pro Asp Leu
145                 150                 155                 160

Leu Thr Ala Ser Asp Thr Leu Arg Glu Val Thr Val Thr Ile Ile Ser
                 165                 170                 175

Arg Lys Arg Cys Asn Ser Gln Ser Tyr Tyr Asn His Lys Pro Val Ile
                 180                 185                 190

Thr Lys Asp Met Ile Cys Ala Gly Asp Ala Arg Gly Gln Lys Asp Ser
             195                 200                 205

Cys Lys Gly Asp Ser Gly Gly Pro Leu Ile Cys Lys Gly Ile Phe His
210                 215                 220

Ala Leu Val Ser Gln Gly Tyr Lys Cys Gly Ile Ala Lys Lys Pro Gly
225                 230                 235                 240

Ile Tyr Thr Leu Leu Thr Lys Lys Tyr Gln Thr Trp Ile Lys Ser Lys
                 245                 250                 255

Leu Ala Pro Ser Arg Ala His
                 260
```

<210> SEQ ID NO 37
<211> LENGTH: 1047
<212> TYPE: DNA
<213> ORGANISM: Homo sapiens
<220> FEATURE:
<221> NAME/KEY: misc_feature
<223> OTHER INFORMATION: Granzyme H

<400> SEQUENCE: 37

```
ggagtcaaca ccaacagctc tgacctgggc agccttcctg agaaaatgca gccattcctc    60
ctcctgttgg cctttcttct gaccctgggg gctgggacag aggagatcat cgggggccat   120
gaggccaagc cccactcccg cccctacatg gcctttgttc agtttctgca agagaagagt   180
cggaagaggt gtggcggcat cctagtgaga aaggactttg tgctgacagc tgctcactgc   240
cagggaagct ccataaatgt caccttgggg gcccacaata tcaaggaaca ggagcggacc   300
cagcagttta tccctgtgaa agacccatcc cccatccag cctataatcc taagaacttc   360
tccaacgaca tcatgctact gcagctggag agaaaggcca agtggaccac agctgtgcgg   420
cctctcaggc tacctagcag caaggcccag gtgaagccag gcagctgtg cagtgtggct   480 ggctggggtt atgtctcaat gagcacttta gcaaccacac tgcaggaagt gttgctgaca   540
```

-continued

```
gtgcagaagg actgccagtg tgaacgtctc ttccatggca attacagcag agccactgag      600
atttgtgtgg gggatccaaa gaagacacag accggtttca agggggactc cggggggccc      660
ctcgtgtgta aggacgtagc ccaaggtatt ctctcctatg gaaacaaaaa agggacacct      720
ccaggagtct acatcaaggt ctcacacttc ctgccctgga taaagagaac aatgaagcgc      780
ctctaacagc aggcatgaga ctaaccttcc tctgggcctg accatctctg ggacagaggc      840
aagaatcccc aaggggtggg cagtcagggt tgcaggactg taataaatgg atctctggtg      900
tagaaaaaaa aaaaaaaaaa aaaaaaaaaa aaaaaaaaaa aaaaaaaaaa aaaaaaaaaa      960
aaaaaaaaaa aaaaaaaaaa aaaaaaaaaa aaaaaaaaaa aaaaaaaaaa aaaaaaaaaa     1020
aaaaaaaaaa aaaaaaaaaa aaaaaaa                                         1047

<210> SEQ ID NO 38
<211> LENGTH: 246
<212> TYPE: PRT
<213> ORGANISM: Homo sapiens
<220> FEATURE:
<221> NAME/KEY: misc_feature
<223> OTHER INFORMATION: Granzyme H

<400> SEQUENCE: 38

Met Gln Pro Phe Leu Leu Leu Ala Phe Leu Leu Thr Pro Gly Ala
1               5                   10                  15

Gly Thr Glu Glu Ile Ile Gly Gly His Glu Ala Lys Pro His Ser Arg
            20                  25                  30

Pro Tyr Met Ala Phe Val Gln Phe Leu Gln Glu Lys Ser Arg Lys Arg
        35                  40                  45

Cys Gly Gly Ile Leu Val Arg Lys Asp Phe Val Leu Thr Ala Ala His
    50                  55                  60

Cys Gln Gly Ser Ser Ile Asn Val Thr Leu Gly Ala His Asn Ile Lys
65                  70                  75                  80

Glu Gln Glu Arg Thr Gln Gln Phe Ile Pro Val Lys Arg Pro Ile Pro
                85                  90                  95

His Pro Ala Tyr Asn Pro Lys Asn Phe Ser Asn Asp Ile Met Leu Leu
            100                 105                 110

Gln Leu Glu Arg Lys Ala Lys Trp Thr Thr Ala Val Arg Pro Leu Arg
        115                 120                 125

Leu Pro Ser Ser Lys Ala Gln Val Lys Pro Gly Gln Leu Cys Ser Val
    130                 135                 140

Ala Gly Trp Gly Tyr Val Ser Met Ser Thr Leu Ala Thr Thr Leu Gln
145                 150                 155                 160

Glu Val Leu Leu Thr Val Gln Lys Asp Cys Gln Cys Glu Arg Leu Phe
                165                 170                 175

His Gly Asn Tyr Ser Arg Ala Thr Glu Ile Cys Val Gly Asp Pro Lys
            180                 185                 190

Lys Thr Gln Thr Gly Phe Lys Gly Asp Ser Gly Gly Pro Leu Val Cys
        195                 200                 205

Lys Asp Val Ala Gln Gly Ile Leu Ser Tyr Gly Asn Lys Lys Gly Thr
    210                 215                 220

Pro Pro Gly Val Tyr Ile Lys Val Ser His Phe Leu Pro Trp Ile Lys
225                 230                 235                 240

Arg Thr Met Lys Arg Leu
                245

<210> SEQ ID NO 39
```

<211> LENGTH: 1074
<212> TYPE: DNA
<213> ORGANISM: Homo sapiens
<220> FEATURE:
<221> NAME/KEY: misc_feature
<223> OTHER INFORMATION: Granzyme K

<400> SEQUENCE: 39

```
gatcaacaca tttcatctgg gcttcttaaa tctaaatctt taaaatgact aagttttctt      60
ccttttctct gttttttccta atagttgggg cttatatgac tcatgtgtgt ttcaatatgg    120
aaattattgg agggaaagaa gtgtcacctc attccaggcc atttatgcc tccatccagt      180
atggcggaca tcacgtttgt ggaggtgttc tgattgatcc acagtgggtg ctgacagcag    240
cccactgcca atatcggttt accaaaggcc agtctcccac tgtggtttta ggcgcacact    300
ctctctcaaa gaatgaggcc tccaaacaaa cactggagat caaaaatttt ataccattct    360
caagagttac atcagatcct caatcaaatg atatcatgct ggttaagctt caaacagccg    420
caaaactcaa taaacatgtc aagatgctcc acataagatc aaaacctct cttagatctg      480
gaaccaaatg caaggttact ggctggggag ccaccgatcc agattcatta agaccttctg    540
acaccctgcg agaagtcact gttactgtcc taagtcgaaa actttgcaac agccaaagtt    600
actacaacgg cgacccttt atcaccaaag acatggtctg tgcaggagat gccaaaggcc      660
agaaggattc ctgtaagggt gactcagggg gccccttgat ctgtaaaggt gtcttccacg    720
ctatagtctc tggaggtcat gaatgtggtg ttgccacaaa gcctggaatc tacaccctgt    780
taaccaagaa ataccagact tggatcaaaa gcaaccttgt cccgcctcat acaaattaag    840
ttacaaataa ttttattgga tgcacttgct tcttttttcc taatatgctc gcaggttaga    900
gttgggtgta agtaaagcag agcacatatg gggtccattt ttgcacttgt aagtcatttt    960
attaaggaat caagttcttt ttcacttgta tcactgatgt atttctacca tgctggtttt   1020
attctaaata aaatttagaa gactcaaaaa aaaaaaaaaa aaaaaaaaaa aaaa          1074
```

<210> SEQ ID NO 40
<211> LENGTH: 264
<212> TYPE: PRT
<213> ORGANISM: Homo sapiens
<220> FEATURE:
<221> NAME/KEY: misc_feature
<223> OTHER INFORMATION: Granzyme K

<400> SEQUENCE: 40

```
Met Thr Lys Phe Ser Ser Phe Ser Leu Phe Phe Leu Ile Val Gly Ala
1               5                   10                  15

Tyr Met Thr His Val Cys Phe Asn Met Glu Ile Ile Gly Gly Lys Glu
            20                  25                  30

Val Ser Pro His Ser Arg Pro Phe Met Ala Ser Ile Gln Tyr Gly Gly
        35                  40                  45

His His Val Cys Gly Gly Val Leu Ile Asp Pro Gln Trp Val Leu Thr
    50                  55                  60

Ala Ala His Cys Gln Tyr Arg Phe Thr Lys Gly Gln Ser Pro Thr Val
65                  70                  75                  80

Val Leu Gly Ala His Ser Leu Ser Lys Asn Glu Ala Ser Lys Gln Thr
                85                  90                  95

Leu Glu Ile Lys Lys Phe Ile Pro Phe Ser Arg Val Thr Ser Asp Pro
            100                 105                 110

Gln Ser Asn Asp Ile Met Leu Val Lys Leu Gln Thr Ala Ala Lys Leu
        115                 120                 125
```

```
Asn Lys His Val Lys Met Leu His Ile Arg Ser Lys Thr Ser Leu Arg
            130                 135                 140
Ser Gly Thr Lys Cys Lys Val Thr Gly Trp Gly Ala Thr Asp Pro Asp
145                 150                 155                 160
Ser Leu Arg Pro Ser Asp Thr Leu Arg Glu Val Thr Val Thr Val Leu
                165                 170                 175
Ser Arg Lys Leu Cys Asn Ser Gln Ser Tyr Tyr Asn Gly Asp Pro Phe
            180                 185                 190
Ile Thr Lys Asp Met Val Cys Ala Gly Asp Ala Lys Gly Gln Lys Asp
            195                 200                 205
Ser Cys Lys Gly Asp Ser Gly Gly Pro Leu Ile Cys Lys Gly Val Phe
            210                 215                 220
His Ala Ile Val Ser Gly Gly His Glu Cys Gly Val Ala Thr Lys Pro
225                 230                 235                 240
Gly Ile Tyr Thr Leu Leu Thr Lys Lys Tyr Gln Thr Trp Ile Lys Ser
                245                 250                 255
Asn Leu Val Pro Pro His Thr Asn
            260
```

<210> SEQ ID NO 41
<211> LENGTH: 951
<212> TYPE: DNA
<213> ORGANISM: Homo sapiens
<220> FEATURE:
<221> NAME/KEY: misc_feature
<223> OTHER INFORMATION: Granzyme M

<400> SEQUENCE: 41

```
ccacagcggc atggaggcct gcgtgtcttc actgctggtg ctggccctgg gggccctgtc      60
agtaggcagc tcctttggga cccagatcat cggggggccgg gaggtgatcc cccactcgcg    120
cccgtacatg gcctcactgc agagaaatgg ctcccacctg tgcggggggtg tcctggtgca    180
cccaaagtgg gtgctgacgg ctgcccactg cctggcccag cggatggccc agctgaggct    240
ggtgctgggg ctccacaccc tggacagccc cggtctcacc ttccacatca aggcagccat    300
ccagcaccct cgctacaagc ccgtccctgc cctggagaac gacctcgcgc tgcttcagct    360
ggacgggaaa gtgaagccca gccggaccat ccggccgttg gccctgccca gtaagcgcca    420
ggtggtggca gcagggactc ggtgcagcat ggccggctgg gggctgaccc accagggcgg    480
gcgcctgtcc cgggtgctgc gggagctgga cctccaagtg ctggacaccc gcatgtgtaa    540
caacagccgc ttctggaacg gcagcctctc ccccagcatg gtctgcctgg cggccgactc    600
caaggaccag gctccctgca agggtgactc gggcgggccc ctggtgtgtg gcaaaggccg    660
ggtgttggcc ggagtcctgt ccttcagctc cagggtctgc actgacatct tcaagcctcc    720
cgtggccacc gctgtggcgc cttacgtgtc ctggatcagg aaggtcaccg ccgatcggc    780
ctgatgccct ggggtgatgg gaccccctc gctgtctcca caggacccctt ccctccagg    840
ggtgcagtgg ggtgggtgag acgggtggg agggacaggg agggaccaat aaatcataat    900
gaagaaaaaa aaaaaaaaaa aaaaaaaaaa aaaaaaaaaa aaaaaaaaa a             951
```

<210> SEQ ID NO 42
<211> LENGTH: 257
<212> TYPE: PRT
<213> ORGANISM: Homo sapiens
<220> FEATURE:
<221> NAME/KEY: misc_feature
<223> OTHER INFORMATION: Granzyme M

<400> SEQUENCE: 42

```
Met Glu Ala Cys Val Ser Ser Leu Leu Val Leu Ala Leu Gly Ala Leu
1               5                   10                  15

Ser Val Gly Ser Ser Phe Gly Thr Gln Ile Ile Gly Gly Arg Glu Val
            20                  25                  30

Ile Pro His Ser Arg Pro Tyr Met Ala Ser Leu Gln Arg Asn Gly Ser
            35                  40                  45

His Leu Cys Gly Gly Val Leu Val His Pro Lys Trp Val Leu Thr Ala
50                  55                  60

Ala His Cys Leu Ala Gln Arg Met Ala Gln Leu Arg Leu Val Leu Gly
65                  70                  75                  80

Leu His Thr Leu Asp Ser Pro Gly Leu Thr Phe His Ile Lys Ala Ala
                85                  90                  95

Ile Gln His Pro Arg Tyr Lys Pro Val Pro Ala Leu Glu Asn Asp Leu
            100                 105                 110

Ala Leu Leu Gln Leu Asp Gly Lys Val Lys Pro Ser Arg Thr Ile Arg
            115                 120                 125

Pro Leu Ala Leu Pro Ser Lys Arg Gln Val Val Ala Ala Gly Thr Arg
130                 135                 140

Cys Ser Met Ala Gly Trp Gly Leu Thr His Gln Gly Gly Arg Leu Ser
145                 150                 155                 160

Arg Val Leu Arg Glu Leu Asp Leu Gln Val Leu Asp Thr Arg Met Cys
                165                 170                 175

Asn Asn Ser Arg Phe Trp Asn Gly Ser Leu Ser Pro Ser Met Val Cys
            180                 185                 190

Leu Ala Ala Asp Ser Lys Asp Gln Ala Pro Cys Lys Gly Asp Ser Gly
            195                 200                 205

Gly Pro Leu Val Cys Gly Lys Gly Arg Val Leu Ala Gly Val Leu Ser
            210                 215                 220

Phe Ser Ser Arg Val Cys Thr Asp Ile Phe Lys Pro Pro Val Ala Thr
225                 230                 235                 240

Ala Val Ala Pro Tyr Val Ser Trp Ile Arg Lys Val Thr Gly Arg Ser
                245                 250                 255

Ala

<210> SEQ ID NO 43
<211> LENGTH: 880
<212> TYPE: DNA
<213> ORGANISM: Rattus norvegicus
<220> FEATURE:
<221> NAME/KEY: misc_feature
<223> OTHER INFORMATION: Granzyme C

<400> SEQUENCE: 43
cctgggagga tgccaccagt cctgatactc ctgaccctac ttctgcctct tggagccaga     60
gcagaggaga tcatcggagg caatgaggtc agtccgcatt cccgccccta catggcatat    120
tttgagtttc tcaatgataa cgggaagaag acgttctgcg gaggcttcct ggtgagagac    180
aacttcgtgc tgacggctgc tcactgcaga ggaagatcaa tgacagtcac actgggggcc    240
cacaacatca aggctaaaga aagacacag cagattatcc ctgtggcaaa cgccactccc    300
caccctgcct ataatcctga taaacgttcc aatgacatca tgctattaaa gctggtgaga    360
agtgccaaga ggactagcgc tgtgaggcct ctcaacctgc caggcgcaa tgcccatgtg     420 aagccaggag atgtgtgcta catggctggc tggggaaaga taaccccaca ggggaattc     480 cccaacacac tgcgggaggt tgagctgaca gtacagaagg atcgggtctg tgagtcccag    540
```

```
ttccaacgtt cttacatcaa agcgagtgag atatgtgtgg gagactcaaa gaccaaggga      600
gcttcctttg aggaagattc tggagggcct cttgtgtgta aaaaggcagc tgcaggcatt      660
gtctcctacg ggaaaactga tggatcagct ccacaggtct tcacgagagt tttaagcttt      720
ttatcctgga taaagaaaac tatgaaaaac agctaaatac aagaagcagc atggatcatt      780
tcctgactaa ccatcttccc tatagctgag tccaggagtg ctctaggaca gatggcagca      840
actgaataaa gcactttttt ctgactggaa aaaaaaaaa                             880
```

<210> SEQ ID NO 44
<211> LENGTH: 248
<212> TYPE: PRT
<213> ORGANISM: Rattus norvegicus
<220> FEATURE:
<221> NAME/KEY: misc_feature
<223> OTHER INFORMATION: Granzyme C

<400> SEQUENCE: 44

```
Met Pro Pro Val Leu Ile Leu Leu Thr Leu Leu Leu Pro Leu Gly Ala
1               5                   10                  15

Arg Ala Glu Glu Ile Ile Gly Gly Asn Glu Val Ser Pro His Ser Arg
            20                  25                  30

Pro Tyr Met Ala Tyr Phe Glu Phe Leu Asn Asp Asn Gly Lys Lys Thr
        35                  40                  45

Phe Cys Gly Gly Phe Leu Val Arg Asp Asn Phe Val Leu Thr Ala Ala
    50                  55                  60

His Cys Arg Gly Arg Ser Met Thr Val Thr Leu Gly Ala His Asn Ile
65                  70                  75                  80

Lys Ala Lys Glu Lys Thr Gln Gln Ile Ile Pro Val Ala Asn Ala Thr
                85                  90                  95

Pro His Pro Ala Tyr Asn Pro Asp Lys Arg Ser Asn Asp Ile Met Leu
            100                 105                 110

Leu Lys Leu Val Arg Ser Ala Lys Arg Thr Ser Ala Val Arg Pro Leu
        115                 120                 125

Asn Leu Pro Arg Arg Asn Ala His Val Lys Pro Gly Asp Val Cys Tyr
    130                 135                 140

Met Ala Gly Trp Gly Lys Ile Thr Pro Gln Gly Glu Phe Pro Asn Thr
145                 150                 155                 160

Leu Arg Glu Val Glu Leu Thr Val Gln Lys Asp Arg Val Cys Glu Ser
                165                 170                 175

Gln Phe Gln Arg Ser Tyr Ile Lys Ala Ser Glu Ile Cys Val Gly Asp
            180                 185                 190

Ser Lys Thr Lys Gly Ala Ser Phe Glu Glu Asp Ser Gly Gly Pro Leu
        195                 200                 205

Val Cys Lys Lys Ala Ala Ala Gly Ile Val Ser Tyr Gly Lys Thr Asp
    210                 215                 220

Gly Ser Ala Pro Gln Val Phe Thr Arg Val Leu Ser Phe Leu Ser Trp
225                 230                 235                 240

Ile Lys Lys Thr Met Lys Asn Ser
                245
```

<210> SEQ ID NO 45
<211> LENGTH: 823
<212> TYPE: DNA
<213> ORGANISM: Rattus norvegicus
<220> FEATURE:
<221> NAME/KEY: misc_feature
<223> OTHER INFORMATION: Granzyme J -continued

<400> SEQUENCE: 45

```
atgattacga attccggttg gcctgtccta ccagtcaaca ctgaaggagg agagatcata    60
tggggtacag agtccaaacc ccactcccgg ccttacatgg cattcataaa tttttatgat   120
agcaattcag acctcaatcg ctgtggcggt ttcctggtgg caaaagacat tgtaatgaca   180
gcagctcact gtaatggaag aaatataaaa gtaatcttag gtgctcacaa tatcaagaaa   240
cgagaaaaca cccaggtcat ctctgttcta aaggccaaac ctcacgagaa ctttaatagt   300
gattcactgg ttaatgacat catgctcctg aagttggaac gcaaagctca actcaatggt   360
gttgtgaaga ctattgccct tcctaggagc caggactggg tgaaacctgg caggtgtgc    420
acagtggcag gttggggac cttggccaat tgtactttgt ctaacacact tcaagaagtg    480
aatctagaag ttcaaaaagg tcagaagtgc caagcatgt ccagaaacta caatgactcc    540
atccagcttt gtgtgggaaa ccccaatgag aggaaggcta ctgctggggg agactcaggg   600
ggtccatttg tgtgcaatgg agtggcccag gcattgtca gttatcgctt gtgtacttgg    660
acacctcctc gagtattcac cagaatctcc agcttcatac cgtggattca gaaaacaatg   720
aaactccttc aacaacccta gaacacaaaa cctgtgtctg ggccaatgtc cagcatcctg   780
gggtatggct atctgagtct taataaagaa atctgtctgc agg                     823
```

<210> SEQ ID NO 46
<211> LENGTH: 246
<212> TYPE: PRT
<213> ORGANISM: Rattus norvegicus
<220> FEATURE:
<221> NAME/KEY: misc_feature
<223> OTHER INFORMATION: Granzyme J

<400> SEQUENCE: 46

```
Met Ile Thr Asn Ser Gly Trp Pro Val Leu Pro Val Asn Thr Glu Gly
1               5                   10                  15

Gly Glu Ile Ile Trp Gly Thr Glu Ser Lys Pro His Ser Arg Pro Tyr
            20                  25                  30

Met Ala Phe Ile Asn Phe Tyr Asp Ser Asn Ser Asp Leu Asn Arg Cys
        35                  40                  45

Gly Gly Phe Leu Val Ala Lys Asp Ile Val Met Thr Ala Ala His Cys
    50                  55                  60

Asn Gly Arg Asn Ile Lys Val Ile Leu Gly Ala His Asn Ile Lys Lys
65                  70                  75                  80

Arg Glu Asn Thr Gln Val Ile Ser Val Leu Lys Ala Lys Pro His Glu
                85                  90                  95

Asn Phe Asn Ser Asp Ser Leu Val Asn Asp Ile Met Leu Leu Lys Leu
            100                 105                 110

Glu Arg Lys Ala Gln Leu Asn Gly Val Val Lys Thr Ile Ala Leu Pro
        115                 120                 125

Arg Ser Gln Asp Trp Val Lys Pro Gly Gln Val Cys Thr Val Ala Gly
    130                 135                 140

Trp Gly Thr Leu Ala Asn Cys Thr Leu Ser Asn Thr Leu Gln Glu Val
145                 150                 155                 160

Asn Leu Glu Val Gln Lys Gly Gln Lys Cys Gln Gly Met Ser Arg Asn
                165                 170                 175

Tyr Asn Asp Ser Ile Gln Leu Cys Val Gly Asn Pro Asn Glu Arg Lys
            180                 185                 190

Ala Thr Ala Gly Gly Asp Ser Gly Gly Pro Phe Val Cys Asn Gly Val
        195                 200                 205
```

```
Ala Gln Gly Ile Val Ser Tyr Arg Leu Cys Thr Trp Thr Pro Pro Arg
        210                 215                 220

Val Phe Thr Arg Ile Ser Ser Phe Ile Pro Trp Ile Gln Lys Thr Met
225                 230                 235                 240

Lys Leu Leu Gln Gln Pro
            245
```

<210> SEQ ID NO 47
<211> LENGTH: 884
<212> TYPE: DNA
<213> ORGANISM: Rattus norvegicus
<220> FEATURE:
<221> NAME/KEY: misc_feature
<223> OTHER INFORMATION: Granzyme K

<400> SEQUENCE: 47

```
cctcgacacc gaggccctgt aattatgagc ttttcttcat ctgctctggt tttccttgtg      60
gccgggattt atatgtcttc agagagtttc catactgaaa ttattggagg gagagaagta     120
cagccacatt ccaggccttt tatggcttcc atccagtacc gcggcaagca tatttgtgga     180
ggagtcctga tccatccgca gtgggtgcta acagccgccc actgctactc tcgaggccac     240
tctcccacgg ttgttttagg agcacattct ctttcaaaga atgagcccat gaaacagaca     300
tttgagatta aggaattcat cccgttctca ggatttaagt ctggaacgaa tgacatcatg     360
ctgataaagc ttcgcacggc tgcagaactg aacaagcatg tccaactgct tcacctgaga     420
tccaaaaact atattagaga tggaactaaa tgccaggtta ctggctgggg atccaccaag     480
ccagatgtgt taaccacctc tgatacactg caggaagtca ctgttaccat cataagtaga     540
aaacgctgca acagccagag ctactacaac cataaacctg ttataaccaa ggacatgatc     600
tgtgcagggg atcgcagagg cgaaaaggat tcctgcaagg gtgactctgg tggtcctttg     660
atctgcaaag gtgtcttcca tgccctagtc tctgggggct ataaatgtgg catctccaac     720
aagcctggag tctacaccct gttgactaag aaatatcaga cctggatcaa agcaagctt     780
gccccgtcga gtgcacattg agatgacaag tggttttctt ggatctgcca gtcacttgct     840
tcttttttcca ggacaagctt gcagactggc tttctcttcg ggcc                     884
```

<210> SEQ ID NO 48
<211> LENGTH: 258
<212> TYPE: PRT
<213> ORGANISM: Rattus norvegicus
<220> FEATURE:
<221> NAME/KEY: misc_feature
<223> OTHER INFORMATION: Granzyme K

<400> SEQUENCE: 48

```
Met Ser Phe Ser Ser Ser Ala Leu Val Phe Leu Val Ala Gly Ile Tyr
1               5                   10                  15

Met Ser Ser Glu Ser Phe His Thr Glu Ile Ile Gly Gly Arg Glu Val
            20                  25                  30

Gln Pro His Ser Arg Pro Phe Met Ala Ser Ile Gln Tyr Arg Gly Lys
        35                  40                  45

His Ile Cys Gly Gly Val Leu Ile His Pro Gln Trp Val Leu Thr Ala
    50                  55                  60

Ala His Cys Tyr Ser Arg Gly His Ser Pro Thr Val Val Leu Gly Ala
65                  70                  75                  80

His Ser Leu Ser Lys Asn Glu Pro Met Lys Gln Thr Phe Glu Ile Lys
                85                  90                  95

Glu Phe Ile Pro Phe Ser Gly Phe Lys Ser Gly Thr Asn Asp Ile Met
```

Leu Ile Lys Leu Arg Thr Ala Ala Glu Leu Asn Lys His Val Gln Leu
            115                 120                 125

Leu His Leu Arg Ser Lys Asn Tyr Ile Arg Asp Gly Thr Lys Cys Gln
            130                 135                 140

Val Thr Gly Trp Gly Ser Thr Lys Pro Asp Val Leu Thr Thr Ser Asp
145                 150                 155                 160

Thr Leu Gln Glu Val Thr Val Thr Ile Ile Ser Arg Lys Arg Cys Asn
                165                 170                 175

Ser Gln Ser Tyr Tyr Asn His Lys Pro Val Ile Thr Lys Asp Met Ile
            180                 185                 190

Cys Ala Gly Asp Arg Arg Gly Glu Lys Asp Ser Cys Lys Gly Asp Ser
            195                 200                 205

Gly Gly Pro Leu Ile Cys Lys Gly Val Phe His Ala Leu Val Ser Gly
            210                 215                 220

Gly Tyr Lys Cys Gly Ile Ser Asn Lys Pro Gly Val Tyr Thr Leu Leu
225                 230                 235                 240

Thr Lys Lys Tyr Gln Thr Trp Ile Lys Ser Lys Leu Ala Pro Ser Ser
                245                 250                 255

Ala His

<210> SEQ ID NO 49
<211> LENGTH: 35
<212> TYPE: DNA
<213> ORGANISM: Artificial sequence
<220> FEATURE:
<223> OTHER INFORMATION: Synthetic primer

<400> SEQUENCE: 49
catgccatgg gggagatcat cgggggacat gaggc                                    35

<210> SEQ ID NO 50
<211> LENGTH: 32
<212> TYPE: DNA
<213> ORGANISM: Artificial sequence
<220> FEATURE:
<223> OTHER INFORMATION: Synthetic primer

<400> SEQUENCE: 50
gctctagatt agtagcgttt catggttttc tt                                       32

<210> SEQ ID NO 51
<211> LENGTH: 1601
<212> TYPE: DNA
<213> ORGANISM: Herpes simplex virus-2

<400> SEQUENCE: 51
cagctgcttc atgcccgtgg tccgctgttc gcgtttgctg gccgtgtccc cggaagaaat         60
cgatttgcat gtctttagct ccaggatgac gcacacacct cccaacgttt tgtcattggc        120
gaattcgaac acgcagatgc agtctgggcg gcgcggcccg aggtccactt cgcatattaa        180
ggtgacgcgc gtggcctcga acagcgagcg accctgcagc gacccgctca tcagcgtcag        240
cagcgttcca caaatcctgg tggcgttgaa ctcccgcacc tctcgggcga acgccttgta        300
gaagcgggta tggcttctca cgccggccaa cagcacgcgc tgcgttcgg tcaggctgct         360 cgtgcgagcg ggcctaccga cggccgcgcg gcgtcccgtc ctagccatcg ccagggggcc        420
tccgaagccc gcggggatcc ggagctgccc acgctgctgc gggtttatat agacggaccc        480
cacggggtgg ggaagaccac cacctccgcg cagctgatgg aggccctggg gccgcgcgac        540

```
aatatcgtct acgtccccga gccgatgact tactggcagg tgctgggggc ctccgagacc    600
ctgacgaaca tctacaacac gcagcaccgt ctggaccgcg gcgagatatc ggccggggag    660
gcggcggtgg taatgaccag cgcccagata acaatgagca cgccttatgc ggcgacggac    720
gccgttttgg ctcctcatat cggggggggag gctgtgggcc cgcaagcccc gccccggcc    780
ctcacccttg ttttcgaccg gcaccctatc gcctccctgc tgtgctaccc ggccgcgcgg    840
tacctcatgg gaagcatgac cccccaggcc gtgttggcgt tcgtggccct catgccccg     900
accgcgcccg gcacgaacct ggtcctgggt gtccttccgg aggccgaaca cgccgaccgc    960
ctggccagac gccaacgccc gggcgagcgg ctttgacctgg ccatgctgtc cgccattcgc    1020
cgtgtctacg atctactcgc caacacggtg cggtacctgc agcgcggcgg gaggtggcgg    1080
gaggactggg gccggctgac gggggtcgcc gcggcgaccc cgcgccccga ccccgaggac    1140
ggcgcggggt ctctgccccg catcgaggac acgctgtttg ccctgttccg cgttcccgag    1200
ctgctggccc caacgggga cttgtaccac atttttgcct gggtcttgga cgtcttggcc    1260
gaccgcctcc ttccgatgca tctatttgtc ctggattacg atcagtcgcc cgtcgggtgt    1320
cgagacgccc tgttgcgcct caccgccggg atgatcccaa cccgcgtcac aaccgccggg    1380
tccatcgccg agatacgcga cctggcgcgc acgtttgccc gcgaggtggg gggagtttag    1440
ttcaaacacg gaagcccgaa cggaaggcct cccggcgatg acggcaataa aagaacagaa    1500
taaaaggcat tgttgtcgtg tggtgtgtcc ataagcgcgg gggttcgggg ccagggctgg    1560
caccgtatca gcaccccacc gaaaaacgga gcgggccgat c                       1601
```

<210> SEQ ID NO 52
<211> LENGTH: 376
<212> TYPE: PRT
<213> ORGANISM: Herpes simplex virus-2

<400> SEQUENCE: 52

```
Met Ala Ser His Ala Gly Gln Gln His Ala Pro Ala Phe Gly Gln Ala
1               5                   10                  15

Ala Arg Ala Ser Gly Pro Thr Asp Gly Arg Ala Ala Ser Arg Pro Ser
            20                  25                  30

His Arg Gln Gly Ala Ser Glu Ala Arg Gly Asp Pro Glu Leu Pro Thr
        35                  40                  45

Leu Leu Arg Val Tyr Ile Asp Gly Pro His Gly Val Gly Lys Thr Thr
    50                  55                  60

Thr Ser Ala Gln Leu Met Glu Ala Leu Gly Pro Arg Asp Asn Ile Val
65                  70                  75                  80

Tyr Val Pro Glu Pro Met Thr Tyr Trp Gln Val Leu Gly Ala Ser Glu
                85                  90                  95

Thr Leu Thr Asn Ile Tyr Asn Thr Gln His Arg Leu Asp Arg Gly Glu
            100                 105                 110

Ile Ser Ala Gly Glu Ala Ala Val Val Met Thr Ser Ala Gln Ile Thr
        115                 120                 125

Met Ser Thr Pro Tyr Ala Ala Thr Asp Ala Val Leu Ala Pro His Ile
    130                 135                 140

Gly Gly Glu Ala Val Gly Pro Gln Ala Pro Pro Ala Leu Thr Leu
145                 150                 155                 160

Val Phe Asp Arg His Pro Ile Ala Ser Leu Leu Cys Tyr Pro Ala Ala
                165                 170                 175

Arg Tyr Leu Met Gly Ser Met Thr Pro Gln Ala Val Leu Ala Phe Val
            180                 185                 190
```

```
Ala Leu Met Pro Pro Thr Ala Pro Gly Thr Asn Leu Val Leu Gly Val
            195                 200                 205

Leu Pro Glu Ala Glu His Ala Asp Arg Leu Ala Arg Arg Gln Arg Pro
    210                 215                 220

Gly Glu Arg Leu Asp Leu Ala Met Leu Ser Ala Ile Arg Arg Val Tyr
225                 230                 235                 240

Asp Leu Leu Ala Asn Thr Val Arg Tyr Leu Gln Arg Gly Gly Arg Trp
                245                 250                 255

Arg Glu Asp Trp Gly Arg Leu Thr Gly Val Ala Ala Thr Pro Arg
                260                 265                 270

Pro Asp Pro Glu Asp Gly Ala Gly Ser Leu Pro Arg Ile Glu Asp Thr
            275                 280                 285

Leu Phe Ala Leu Phe Arg Val Pro Glu Leu Leu Ala Pro Asn Gly Asp
    290                 295                 300

Leu Tyr His Ile Phe Ala Trp Val Leu Asp Val Leu Ala Asp Arg Leu
305                 310                 315                 320

Leu Pro Met His Leu Phe Val Leu Asp Tyr Asp Gln Ser Pro Val Gly
                325                 330                 335

Cys Arg Asp Ala Leu Leu Arg Leu Thr Ala Gly Met Ile Pro Thr Arg
                340                 345                 350

Val Thr Thr Ala Gly Ser Ile Ala Glu Ile Arg Asp Leu Ala Arg Thr
            355                 360                 365

Phe Ala Arg Glu Val Gly Gly Val
    370                 375

<210> SEQ ID NO 53
<211> LENGTH: 1799
<212> TYPE: DNA
<213> ORGANISM: Herpes simplex virus-1

<400> SEQUENCE: 53
gggtcctagg ctccatgggg accgtatacg tggacaggct ctggagcatc gcacgactgc      60
gtgatattac cggagacctt ctgcgggacg agccgggtca cgcggctgac ggagcgtccg     120
ttgggcgaca acaccaggaa cggggcacag gtacactatc ttgtcacccg gagcgcgagg     180
gactgcagga gcttcaggga gtggcgcagc tgcttcatcc ccgtggcccg ttgctcgcgt     240 tgctggcgg tgtccccgga agaaatatat ttgcatgtct ttagttctat gatgacacaa     300
accccgccca gcgtcttgtc attggcgaat tcgaacacgc agatgcagtc ggggcggcgc     360
ggtcccaggt ccacttcgca tattaaggtg acgcgtgtgg cctcgaacac cgagcgaccc     420
tgcagcgacc cgcttaacag cgtcaacagc gtgccgcaga tcttggtggc gtgaaactcc     480
cgcacctctt tggcaagcgc cttgtagaag cgcgtatggc ttcgtacccc tgccatcaac     540
acgcgtctgc gttcgaccag gctgcgcgtt ctcgcggcca tagcaaccga cgtacggcgt     600
tgcgccctcg ccggcagcaa gaagccacgg aagtccgcct ggagcagaaa atgcccacgc     660
tactgcgggt ttatatagac ggtcctcacg ggatggggaa aaccaccacc acgcaactgc     720
tggtggccct gggttcgcgc gacgatatcg tctacgtacc cgagccgatg acttactggc     780
aggtgctggg ggcttccgag acaatcgcga acatctacac cacacaacac cgcctcgacc     840
agggtgagat atcggccggg gacgcggcgg tggtaatgac aagcgcccag ataacaatgg     900
gcatgcctta tgccgtgacc gacgccgttc tggctcctca tgtcgggggg gaggctggga     960
gttcacatgc cccgccccg gccctcaccc tcatcttcga ccgccatccc atcgccgccc    1020
tcctgtgcta cccggccgcg cgataccttta tgggcagcat gaccccccag gccgtgctgg    1080
```

```
cgttcgtggc cctcatcccg ccgaccttgc ccggcacaaa catcgtgttg ggggcccttc   1140
cggaggacag acacatcgac cgcctggcca aacgccagcg ccccggcgag cggcttgacc   1200
tggctatgct ggccgcgatt cgccgcgttt acgggctgct tgccaatacg gtgcggtatc   1260
tgcagggcgg cgggtcgtgg tgggaggatt ggggacagct ttcggggacg gccgtgccgc   1320 cccaggtgc cgagcccag agcaacgcgg cccacgacc ccatatcggg gacacgttat   1380
ttaccctgtt tcgggccccc gagttgctgg cccccaacgg cgacctgtat aacgtgtttg   1440
cctgggcctt ggacgtcttg gccaaacgcc tccgtcccat gcacgtcttt atcctggatt   1500
acgaccaatc gcccgccggc tgccgggacg ccctgctgca acttacctcc gggatggtcc   1560
agacccacgt caccacccca ggctccatac cgacgatctg cgacctggcg cgcacgtttg   1620
cccgggagat gggggaggct aactgaaaca cggaaggaga caataccgga aggaacccgc   1680
gctatgacgg caataaaaag acagaataaa acgcacgggt gttgggtcgt tgttcataa   1740 acgcggggtt cggtcccagg gctggcactc tgtcgatacc ccaccgagac cccattggg   1799

<210> SEQ ID NO 54
<211> LENGTH: 376
<212> TYPE: PRT
<213> ORGANISM: Herpes simplex virus-1

<400> SEQUENCE: 54

Met Ala Ser Tyr Pro Cys His Gln His Ala Ser Ala Phe Asp Gln Ala
1               5                   10                  15

Ala Arg Ser Arg Gly His Ser Asn Arg Arg Thr Ala Leu Arg Pro Arg
            20                  25                  30

Arg Gln Gln Glu Ala Thr Glu Val Arg Leu Glu Gln Lys Met Pro Thr
        35                  40                  45

Leu Leu Arg Val Tyr Ile Asp Gly Pro His Gly Met Gly Lys Thr Thr
    50                  55                  60

Thr Thr Gln Leu Leu Val Ala Leu Gly Ser Arg Asp Asp Ile Val Tyr
65                  70                  75                  80

Val Pro Glu Pro Met Thr Tyr Trp Gln Val Leu Gly Ala Ser Glu Thr
                85                  90                  95

Ile Ala Asn Ile Tyr Thr Thr Gln His Arg Leu Asp Gln Gly Glu Ile
            100                 105                 110

Ser Ala Gly Asp Ala Ala Val Val Met Thr Ser Ala Gln Ile Thr Met
        115                 120                 125

Gly Met Pro Tyr Ala Val Thr Asp Ala Val Leu Ala Pro His Val Gly
    130                 135                 140

Gly Glu Ala Gly Ser Ser His Ala Pro Pro Ala Leu Thr Leu Ile
145                 150                 155                 160

Phe Asp Arg His Pro Ile Ala Ala Leu Leu Cys Tyr Pro Ala Ala Arg
                165                 170                 175

Tyr Leu Met Gly Ser Met Thr Pro Gln Ala Val Leu Ala Phe Val Ala
            180                 185                 190

Leu Ile Pro Pro Thr Leu Pro Gly Thr Asn Ile Val Leu Gly Ala Leu
        195                 200                 205

Pro Glu Asp Arg His Ile Asp Arg Leu Ala Lys Arg Gln Arg Pro Gly
    210                 215                 220

Glu Arg Leu Asp Leu Ala Met Leu Ala Ala Ile Arg Arg Val Tyr Gly
225                 230                 235                 240

Leu Leu Ala Asn Thr Val Arg Tyr Leu Gln Gly Gly Gly Ser Trp Trp
                245                 250                 255
```

```
Glu Asp Trp Gly Gln Leu Ser Gly Thr Ala Val Pro Pro Gln Gly Ala
            260                 265                 270

Glu Pro Gln Ser Asn Ala Gly Pro Arg Pro His Ile Gly Asp Thr Leu
        275                 280                 285

Phe Thr Leu Phe Arg Ala Pro Glu Leu Leu Ala Pro Asn Gly Asp Leu
    290                 295                 300

Tyr Asn Val Phe Ala Trp Ala Leu Asp Val Leu Ala Lys Arg Leu Arg
305                 310                 315                 320

Pro Met His Val Phe Ile Leu Asp Tyr Asp Gln Ser Pro Ala Gly Cys
            325                 330                 335

Arg Asp Ala Leu Leu Gln Leu Thr Ser Gly Met Val Gln Thr His Val
        340                 345                 350

Thr Thr Pro Gly Ser Ile Pro Thr Ile Cys Asp Leu Ala Arg Thr Phe
    355                 360                 365

Ala Arg Glu Met Gly Glu Ala Asn
370                 375
```

<210> SEQ ID NO 55
<211> LENGTH: 1518
<212> TYPE: DNA
<213> ORGANISM: Herpes simplex virus-1

<400> SEQUENCE: 55

```
tgacgcatgt ggaggctaac agtgtcgaat aacgctttac aaacaattat taacgcccgg     60
ttaccaggcg aagaggggct gtggcagatt catctgcagg acggaaaaat cagcgccatt    120
gatgcgcaat ccggcgtgat gcccataact gaaaacagcc tggatgccga caaggttta    180
gttataccgc cgtttgtgga gccacatatt cacctggaca ccacgcaaac cgccggacaa    240
ccgaactgga atcagtccgg cacgctgttt gaaggcattg aacgctgggc cgagcgcaaa    300
gcgttattaa cccatgacga tgtgaaacaa cgcgcatggc aaacgctgaa atggcagatt    360
gccaacggca ttcagcatgt gcgtacccat gtcgatgttt cggatgcaac gctaactgcg    420
ctgaaagcaa tgctggaagt gaagcaggaa gtcgcgccgt ggattgatct gcaaatcgtc    480
gccttccctc aggaagggat tttgtcgtat cccaacggtg aagcgttgct ggaagaggcg    540
ttacgcttag gggcagatgt agtggggcg attccgcatt ttgaatttac ccgtgaatac    600
ggcgtggagt cgctgcataa aaccttcgcc ctggcgcaaa aatacgaccg tctcatcgac    660
gttcactgtg atgagatcga tgacgagcag tcgcgctttg tcgaaaccgt tgctgccctg    720
gcgcaccatg aaggcatggg cgcgcgagtc accgccagcc acaccacggc aatgcactcc    780
tataacgggg cgtataccte acgcctgttc cgcttgctga aaatgtccgg tattaacttt    840
gtcgccaacc cgctggtcaa tattcatctg caaggacgtt tcgatacgta tccaaaacgt    900
cgcggcatca cgcgcgttaa agagatgctg agtccggca ttaacgtctg ctttggtcac    960
gatgatgtct tcgatccgtg gtatccgctg gaacggcga atatgctgca agtgctgcat   1020
atggggctgc atgtttgcca gttgatgggc tacgggcaga ttaacgatgg cctgaattta   1080
atcacccacc acagcgcaag gacgttgaat ttgcaggatt acggcattgc cgccggaaac   1140
agcgccaacc tgattatcct gccggctgaa aatgggtttg atgcgctgcg ccgtcaggtt   1200
ccggtacgtt attcggtacg tggcggcaag gtgattgcca gcacacaacc ggcacaaacc   1260
accgtatatc tggagcagcc agaagccatc gattacaaac gttgaacgac tgggttacag   1320
cgagcttagt ttatgccgga tgcgcggtga acgcctattc cggcctacgt agagcactga   1380
actcgtaggc ctgataagcg tagcgcatca ggcaattcca gccgctgatc tgtgtcagcg   1440
```

```
gctaccgtga ttcattcccg ccaacaaccg cgcattcctc caacgccatg tgcaaaaatg    1500
ccttcgcagc ggctgtct                                                  1518
```

<210> SEQ ID NO 56
<211> LENGTH: 427
<212> TYPE: PRT
<213> ORGANISM: Herpes simplex virus-1

<400> SEQUENCE: 56

```
Met Ser Asn Asn Ala Leu Gln Thr Ile Ile Asn Ala Arg Leu Pro Gly
1               5                   10                  15

Glu Glu Gly Leu Trp Gln Ile His Leu Gln Asp Gly Lys Ile Ser Ala
            20                  25                  30

Ile Asp Ala Gln Ser Gly Val Met Pro Ile Thr Glu Asn Ser Leu Asp
        35                  40                  45

Ala Glu Gln Gly Leu Val Ile Pro Pro Phe Val Glu Pro His Ile His
    50                  55                  60

Leu Asp Thr Thr Gln Thr Ala Gly Gln Pro Asn Trp Asn Gln Ser Gly
65                  70                  75                  80

Thr Leu Phe Glu Gly Ile Glu Arg Trp Ala Glu Arg Lys Ala Leu Leu
                85                  90                  95

Thr His Asp Asp Val Lys Gln Arg Ala Trp Gln Thr Leu Lys Trp Gln
            100                 105                 110

Ile Ala Asn Gly Ile Gln His Val Arg Thr His Val Asp Val Ser Asp
        115                 120                 125

Ala Thr Leu Thr Ala Leu Lys Ala Met Leu Glu Val Lys Gln Glu Val
    130                 135                 140

Ala Pro Trp Ile Asp Leu Gln Ile Val Ala Phe Pro Gln Glu Gly Ile
145                 150                 155                 160

Leu Ser Tyr Pro Asn Gly Glu Ala Leu Leu Glu Glu Ala Leu Arg Leu
                165                 170                 175

Gly Ala Asp Val Val Gly Ala Ile Pro His Phe Glu Phe Thr Arg Glu
            180                 185                 190

Tyr Gly Val Glu Ser Leu His Lys Thr Phe Ala Leu Ala Gln Lys Tyr
        195                 200                 205

Asp Arg Leu Ile Asp Val His Cys Asp Glu Ile Asp Asp Glu Gln Ser
    210                 215                 220

Arg Phe Val Glu Thr Val Ala Ala Leu Ala His His Glu Gly Met Gly
225                 230                 235                 240

Ala Arg Val Thr Ala Ser His Thr Thr Ala Met His Ser Tyr Asn Gly
                245                 250                 255

Ala Tyr Thr Ser Arg Leu Phe Arg Leu Leu Lys Met Ser Gly Ile Asn
            260                 265                 270

Phe Val Ala Asn Pro Leu Val Asn Ile His Leu Gln Gly Arg Phe Asp
        275                 280                 285

Thr Tyr Pro Lys Arg Arg Gly Ile Thr Arg Val Lys Glu Met Leu Glu
    290                 295                 300

Ser Gly Ile Asn Val Cys Phe Gly His Asp Asp Val Phe Asp Pro Trp
305                 310                 315                 320

Tyr Pro Leu Gly Thr Ala Asn Met Leu Gln Val Leu His Met Gly Leu
                325                 330                 335

His Val Cys Gln Leu Met Gly Tyr Gly Gln Ile Asn Asp Gly Leu Asn
            340                 345                 350

Leu Ile Thr His His Ser Ala Arg Thr Leu Asn Leu Gln Asp Tyr Gly
```

-continued

```
        355                 360                 365

Ile Ala Ala Gly Asn Ser Ala Asn Leu Ile Ile Leu Pro Ala Glu Asn
    370                 375                 380

Gly Phe Asp Ala Leu Arg Arg Gln Val Pro Val Arg Tyr Ser Val Arg
385                 390                 395                 400

Gly Gly Lys Val Ile Ala Ser Thr Gln Pro Ala Gln Thr Thr Val Tyr
                405                 410                 415

Leu Glu Gln Pro Glu Ala Ile Asp Tyr Lys Arg
            420                 425
```

APOPTOSIS-INDUCING GENES FOR TREATING CANCER

FIELD

The invention relates to the field of molecular biology. More particularly, the invention relates to recombinant nucleic acids and treatment of disorders or diseases, such as cancer.

BACKGROUND

Cancer is widely recognized as one of the major challenges to the healthcare industry, in terms of the variety of specific disease processes embraced by the term, the number of people and animals afflicted, and the effort and resources devoted to its treatment. For years, cancer has resisted man's attempts to understand and, hence, control the disease. Although that resistance has been overcome in certain contexts, the major, broad-based therapeutic approaches to cancer treatment continue to be burdened by deleterious side effects. For example, chemotherapy involves the delivery of cytotoxic compounds that target dividing cells, thus preferentially, but imperfectly, destroying cancer cells. Healthy dividing cells are also lost, however, and the treatments can lead to serious, life-threatening complications and the treatments frequently result in pain, nausea, hair loss, and a highly increased risk of serious infection. Radiotherapy, another broad-based approach, also exhibits imperfect targeting of cancer cells, with the result that healthy as well as cancerous cells can receive a lethal dose of radiation, leading to side effects such as pain, loss of vigor, and an increased risk of secondary malignancies, up to 20%, in some cases.

By way of example, ovarian carcinoma represents a significant women's health concern, as it is the most common cause of death from gynecological malignancy in the Western world (1). Within the spectrum of ovarian carcinomas, surface epithelial tumors represent 90% of all malignant ovarian neoplasms (2). Survival rates for surface epithelial ovarian carcinoma (30-40%) have remained relatively constant for the past 30 years (1), primarily due to the fact that metastatic spread via the lymphatics and by peritoneal implantation is clinically silent, resulting in a late stage at presentation.

Despite the abundance of molecular studies in the field of cancer research, significant independent prognostic indicators used in treatment stratification of patients with ovarian tumors are primarily clinical. They include age at diagnosis, International Federation of Gynecology and Obstetrics (FIGO) stage at presentation, and residual disease after surgery. Common molecular abnormalities described in ovarian tumors include mutations in the TP53 tumor suppressor gene, genetic amplification of the growth factor Her-2/neu (c-erbB-2), and loss of the distal half of chromosome 1 Sq (3-6). The expression of Survivin has also recently been demonstrated to be aberrantly elevated in over 70% of epithelial ovarian tumors (7, 8).

Ovarian carcinoma is the fifth leading cause of death from cancer among women in the United States, and the fourth among women over 40 years of age, resulting in an estimated 14,000 deaths per year (1). Although treatment of early stage ovarian cancer yields 5-year survival rates close to 90% (39), approximately 25-40% of patients (especially those with unfavorable prognostic indicators) are likely to relapse. Patients who clinically relapse less than 6 months after chemotherapy have very limited treatment options, often with low response rates to standard chemotherapeutic agents and a poor median survival (11 months) (9). For this reason there is a pressing need for the development of novel therapies that will effectively treat advanced and recurrent ovarian carcinoma.

The immune system also plays a role in combating cancer. CTL-mediated immunity is an important natural response to tumor cell growth (11, 40). It is also an important therapeutic avenue that has been explored in clinical trials to reduce tumor cell proliferation (41-43). Most immunotherapy studies targeted to cancer cells rely on the use of activated T-lymphocytes to perform this action. These studies can be hampered by the lack of antigen-presenting tumor cells within the patient. Suicide gene approaches are currently being tried by a number of different groups to treat cancer (44, 45), but specificity and efficacy concerns remain.

Successful treatment of ovarian cancer ultimately depends on clinical response to therapy. Early-stage ovarian cancer is most sensitive to platinum-based chemotherapy regimens, which have been the gold standard in the treatment of this disease (9). The preferred therapeutic regimen for advanced stage ovarian carcinoma relies on a combination of a platinum-based compound (cisplatin or carboplatin) and a taxane (commonly paclitaxel) (10). Treatment of advanced stage and recurrent ovarian carcinoma is frequently hampered by high rates of chemoresistance. Research on the development and efficacy of therapeutics for ovarian carcinoma is critical to improve patient survival. Accordingly, the medical and veterinary communities continue to seek treatment modalities that will provide better targeting of cancer cells with a capacity to deliver an efficacious dose of cytotoxin to such cells.

Molecular biology has been contributing significant advances to health care for several decades. Although early efforts to harness recombinant DNA technologies for use in health care were occasionally problematic, the past decade has seen a dramatic increase in the reliability and efficacy of recombinant DNA methodologies used to provide health care. Today, man's understanding of the processes controlling gene expression has developed to the point where the medical and veterinary communities are receptive to this approach to the treatment and amelioration of a wide variety of conditions and diseases.

Programmed cell death (also referred to as apoptosis) is distinguishable, both morphologically and functionally, from necrosis. Programmed cell death is a natural form of death that organisms use to dispose of cells. Cells dying by programmed cell death usually shrink, rarely lyse, and are efficiently removed from the organism (rapidly recognized and engulfed by macrophages) without the appearance of inflammation.

Apoptosis was initially used to describe a subset of programmed cell deaths sharing a particular set of morphological features that include membrane blebbing, shrinkage of cytoplasm, chromatic condensation and formation of a "DNA ladder" (i.e., DNA fragmentation). During apoptosis, cells lose their cell junctions and microvilli, the cytoplasm condenses, and nuclear chromatin marginates into a number of discrete masses. While the nucleus fragments, the cytoplasm contracts and both mitochondria and ribosomes become densely compacted. After dilation of the endoplasmic reticulum and its fusion with the plasma membrane, the cell breaks up into several membrane-bound vesicles, referred to as apoptotic bodies, which are usually phagocytosed by adjacent cells. Activation of particular genes, such as tumor suppressor genes in vertebrates, is thought to be necessary for apoptosis to occur. Apoptosis induced by numerous cytotoxic agents can usually be suppressed by expression of the anti-apoptotic gene bcl-2, which produces a cytoplasmic protein, Bcl-2.

Survivin has recently been identified as an inhibitor of apoptosis protein (IAP), a relatively small group of related proteins that inhibit the apoptotic process by interfering with caspase function. The first IAP was discovered in baculovirus and IAPs have now been reported in *Drosophila*, chick, mouse and human. Five human IAPs have been identified: HIAP1, HIAP2, XIAP (X-chromosome linked IAP), NAIP (neuronal apoptosis inhibiting protein) and Survivin. The gene encoding human Survivin is located on chromosome 17q25. Survivin is a 16.5 kD protein originally identified as cytoplasmic, but now known to be present in the nucleus and mitochondria as well. Survivin contains a single partially conserved BIR domain, and a highly charged carboxyl-terminus coiled-coil region instead of a RING finger, which inhibits apoptosis induced by growth factor withdrawal, UV-irradiation, Fas ligand, and other pro-apoptotic stimuli.

The Survivin promoter has been shown to be relatively silent in non-malignant cells and tissues both in vitro and in vivo (23, 24). Furthermore the survivin gene is relatively silent in non-transformed, differentiated cells (25). Expression of Survivin occurs in G2/M in a cell cycle-dependent manner, and the gene product localizes to mitotic spindle microtubules and intercellular acto-myosin bridges, i.e., midbodies, during cell division. Interference with this topography, or blocking survivin expression, caused increased caspase-3 activity in G2/M and a profound dysregulation of mitotic progression. Remarkably, Survivin was identified as one of the top four "transcriptomes," out of 3.5 million mRNAs uniformly expressed in cancer but not in normal tissues. Additionally, it has been shown that transformed cells are exquisitely sensitive to manipulation at this mitotic stage as interference with Survivin expression and function using dominant-negative mutants with point mutations in the conserved baculovirus IAP repeat (BIR) domain, or survivin antisense, resulted in aberrant mitoses and spontaneous apoptosis.

Unlike other members of the IAP family, Survivin has only one BIR domain and does not have a carboxy-terminal RING finger. Instead, Survivin has a carboxy-terminal coiled-coil region. Based on overall sequence conservation, the absence of a carboxy terminus RING finger and the presence of a single, partially conserved, BIR domain, Survivin shares the highest degree of similarity with its *C. elegans* and yeast orthologs. Importantly, Survivin is minimally expressed in adult tissues, but is prominently expressed in most common human cancers, including cancers of the lung, colon, breast, pancreas, prostate, and central nervous system, and in about 50% of high-grade non-Hodgkin's lymphomas. For example, Survivin has been detected in adenocarcinoma of the pancreas, breast adenocarcinoma, colon cancer, head and neck squamous cell carcinoma, neuroblastoma, malignant thymoma, and prostate cancer. This expression pattern suggests that overexpression of Survivin or alterations in survivin gene regulation may commonly occur during tumorigenesis. Survivin is highly expressed in all common human cancers. These observations indicate that apoptosis inhibition may be a general feature of neoplasia.

One of the central functions of apoptosis in maintaining homeostasis is the elimination of damaged and potentially harmful cells. For this process to be effective, the apoptotic machinery must communicate with monitors, or checkpoints, of cell health, sensing DNA damage, adverse environmental conditions, and oncogene or viral transformation. Checkpoint activation under these conditions initiates apoptosis via the assembly of an evolutionarily conserved "apoptosome," which in mammalian cells comprises an upstream cell-death protease, Caspase-9, the adapter/cofactor protein Apaf-1, mitochondrion-derived cytochrome C and dATP/ATP. Although it is debated how apoptosome assembly promotes Caspase-9 catalytic activity, this process culminates with downstream activation of effector caspases and cleavage of critical cellular substrates. The apoptotic mechanism also appears to monitor cell cycle transitions, assembly of a bipolar mitotic apparatus, the ploidy level of the genome, and the timing of cytokinesis. In this context, dysregulated expression of apoptosis inhibitors Bcl-2 and Bcl-$_{XL}$ has been shown to restrain S phase entry, to promote cell cycle exit, and to cause aneuploidy, further demonstrating a role for the apoptotic machinery in cell-cycle progression.

The IAPs, or inhibitor-of-apoptosis proteins, may be regarded as functional antagonists to a class of proteins known as Apoptosis-Inducing Proteins, or AIPs. One member of the latter class of proteins, Granzyme B, is a serine protease primarily found in cytoplasmic granules of cytotoxic T lymphocytes and natural killer cells. Granzyme B plays an important role in inducing apoptotic changes in target cells by cytotoxic cell-mediated killing. Granzyme B is normally produced by natural killer (NK) cells and cytotoxic T-lymphocytes (CTLs) and is released from intracellular granules in response to stimuli that include viral or bacterial infection, abnormally proliferating cells or foreign cell invasion (11, 12). This mechanism protects the host cell from destruction by intracellular pathogens, tumors and foreign cells within the context of the normal immune system (11). Granzyme B is synthesized as a preproenzyme that is activated by two proteolytic cleavages that release an 18-amino-acid leader sequence encoded by exon 1 and a di-peptide motif (Gly-Glu) at the N-terminus. These cleavages are apparently required for full maturation of the enzyme and to allow it to fold into its catalytically active conformation. Although the active form of Granzyme B is generally viewed as that part of the full-length amino acid sequence on the C-terminal side of the di-peptide (GE) processing site, active forms may be considered to include the GE di-peptide and may further include an N-terminal methionine.

Like the caspases, Granzyme B recognizes substrates specifically at aspartic acid for cleavage. (See U.S. Pat. No. 6,537,784, incorporated herein by reference.) To gain entry into its target cell, Granzyme B relies predominantly on perforin, a pore-forming auxiliary protein. Upon entry, active Granzyme B induces apoptosis through both mitochondrial-dependent and mitochondrial-independent mechanisms (11, 13-15). A decrease in mitochondrial membrane potential, direct cleavage of nuclear proteins leading to DNA fragmentation and activation of the Caspase-3 pathway are all known effects of Granzyme B activation (11, 14-16). Granzyme B is known to catalyze cleavage and activation of several caspases, and it is also known to be involved in caspase-independent pathways (see FIG. 1). These diverse mechanisms of Granzyme-B-mediated programmed cell death ensure the successful progression of granule-mediated cell death even in target cells lacking functional caspase proteins, thus providing the host with overlapping safeguards against foreign invaders (16). Despite these sophisticated defense mechanisms, tumor cells have developed molecular evasion mechanisms against Granzyme B-mediated apoptosis (17, 18). These mechanisms include tumor-induced T-cell deletion (by suicide and fratricide), defects in tumor-infiltrating lymphocytes, and impaired presentation of tumor-associated antigens, among others. Recently, certain serpins that inactivate Granzyme-B have also been described (19, 20). It is unknown, however, whether these enzymes are clinically relevant inhibitors Granzyme B in vivo.

Thus, modulation or control of apoptosis provides an alternative route to the use of cytotoxic chemicals or radiation in facilitating the death of deleterious cells, such as cancer cells. Still, a need persists in the art for methods of specifically treating cancer in a manner that does not introduce deleterious side effects typically associated with radiotherapy, chemotherapy and combinational therapies, yet is versatile in exhibiting activity against a range of cancers and is cost-effective in providing a single approach, or set of approaches, to such treatments.

SUMMARY

The invention disclosed herein satisfies at least one of the aforementioned needs in the art by providing materials and methods relating to a recombinant nucleic acid molecule that preferentially expresses an apoptosis-inducing gene product in cancer cells, thereby inducing apoptotic destruction of those cancer cells. These materials and methods are useful in treating a disease or condition in which a cell has a deleterious effect on a tissue, organ or organism, such as a cancer condition and in ameliorating a symptom of, or providing a palliative treatment for, any such disease or condition, such as a cancer condition. In general, the invention provides an IAP (inhibitor of apoptosis protein) expression control sequence operatively linked to a gene encoding an active apoptosis-inducing protein (AIP, the gene being an AIG, or apoptosis-inducing gene).

In one aspect, the invention provides a recombinant nucleic acid molecule comprising at least one expression control region (e.g., a promoter, an operator, an enhancer, an expression factor binding site) for an inhibitor of apoptosis gene operatively linked to a polynucleotide comprising a coding region of an active apoptosis-inducing protein (IAP). A preferred expression control region is selected from the group consisting of the promoter of HIAP1, HIAP2, XIAP, NAIP and survivin. A preferred polynucleotide comprising a coding region of an active IAP is a coding region that comprises a sequence encoding a protein selected from the group consisting of Granzyme B (see, e.g., SEQ ID NOS: 4, 6, 8, 10, 12, 14, 16, 18, 20, and 22; see also Table 1), Granzyme A (see, e.g., SEQ ID NO:24), Granzyme H (see, e.g., SEQ ID NO:38), Granzyme K (see, e.g., SEQ ID NOS:36, 40 and 48), Granzyme M (see, e.g., SEQ ID NO:42), Granzyme C (see, e.g., SEQ ID NOS:26 and 44), Granzyme D (see, e.g., SEQ ID NO:28), Granzyme E (see, e.g., SEQ ID NO:30), Granzyme F (see, e.g., SEQ ID NO:32), Granzyme G (see, e.g., SEQ ID NO:34), Granzyme I, Granzyme J (see, e.g., SEQ ID NO:46), Cathepsin, Granulysin, Hemolysin, Amoebapore A, Amoebapore B, Amoebapore C, Cytosine Deaminase (see, e.g., SEQ ID NOs:55-56), Uracil Phosphoribosyltransferase, Thymidine Kinase (see, e.g., SEQ ID NOs: 51-54), and variants and fragments thereof. In some embodiments of this aspect of the invention, the coding region encodes any of the Granzyme proteins, such as a protein comprising an amino acid sequence selected from the group consisting of SEQ ID NOS: 4, 6, 8, 10, 12, 14, 16, 18, 20, 22, 24, 26, 28, 30, 32, 34, 36, 38, 40, 42, 44, 46, and 48. (See Table 1 for a list of all sequences disclosed herein.) The physical relationship of an expression control region, e.g., a promoter region, of an inhibitor of apoptosis protein (IAP) gene and a coding region for an apoptosis-inducing protein (AIP) is defined by the elements being in operative linkage, as would be known in the art. Suitable distances separating the elements are readily determinable using routine procedures known in the art. By way of example, the invention comprehends separation distances of 1,000 nucleotides or more, but it is expected that separations of less than 1,000 nucleotides, and even 100 nucleotides or less will be typical and will result in reliable operative linkages.

The recombinant nucleic acid molecules of the invention further include molecules wherein the coding region comprises a Granzyme-encoding sequence, such as a sequence selected from the group consisting of SEQ ID NOS:2, 3, 5, 7, 9, 11, 13, 15, 17, 19, 21, 23, 25, 27, 29, 31, 33, 35, 37, 39, 41, 43, 45 and 47. In some embodiments, the recombinant nucleic acid molecule comprises a coding region encoding a human Granzyme protein, such as a protein comprising an amino acid sequence selected from the group consisting of SEQ ID NOS:4, 6, 24, 26, 28, 30, 32, 34, 36, 38, 40 and 42. In some embodiments, the recombinant nucleic acid molecule comprises a mammalian sequence for a coding region encoding a Granzyme protein, such as a sequence selected from the group consisting of SEQ ID NOS:2, 3, 5, 23, 25, 27, 29, 31, 33, 35, 37, 39 and 41.

Additional embodiments of this aspect of the invention comprise a recombinant nucleic acid molecule as described above, wherein the coding region encodes an active form polypeptide. Exemplary recombinant nucleic acid molecules include molecules comprising a coding region that encodes an active form of Granzyme B, such as a protein having a sequence selected from the group consisting of amino acids 19-247 of SEQ ID NO:4, amino acids 7-235 of SEQ ID NO:6, amino acids 19-247 of SEQ ID NO:8, amino acids 10-248 of SEQ ID NO:10, amino acids 18-251 of SEQ ID NO:14, amino acids 21-247 of SEQ ID NO:16, and amino acids 3-225 of SEQ ID NO: 20. In those embodiments of the invention comprising coding regions for active forms of a Granzyme enzyme, the encoded protein, when expressed, may exhibit an N-terminal Met, and/or a GE dipeptide processing site disposed towards or at the N-terminus, but it is most likely to begin with the amino acid following the dipeptide GE (see, e.g., SEQ ID NO:4), which is expected to be released during post-translational processing. Preferred embodiments include recombinant nucleic acid molecules wherein the coding region comprises a sequence selected from the group consisting of SEQ ID NOS:2, 3, 5, and nucleotides 122-810 of SEQ ID NO: 3.

Additional embodiments according to this aspect of the invention include recombinant nucleic acid molecules as described above, wherein the IAP promoter region is the survivin promoter. An exemplary survivin promoter comprises a sequence selected from the group consisting of SEQ ID NO:1 and nucleotides 68-268 of SEQ ID NO:1 (corresponding to nucleotides 795-1062 of the Genbank Acc. No. AY795969, with the exception of the 3'-terminal C in SEQ ID NO:1, which corresponds to a G in AY795969; either sequence is functional).

Another aspect of the invention is a pharmaceutical composition comprising the recombinant nucleic acid molecule described herein and a pharmaceutically acceptable carrier. Any pharmaceutically acceptable carrier known in the art, including pharmaceutical excipients, diluents and adjuvants, is contemplated. A related aspect involves the preparation of a medicament for use in treating a disease or disorder, such as a cancer condition as described below.

Another aspect of the invention provides a process for constructing a recombinant nucleic acid molecule, as described herein, comprising operatively linking a nucleic acid comprising an Inhibitor-Apoptosis Protein (IAP) expression control region, e.g., a promoter region such as a survivin promoter region, to a polynucleotide encoding a full-length or active Apoptosis Inducing Protein (AIP), such as an active Granzyme B. In some embodiments, the process produces a recombinant molecule comprising a nucleic acid operatively linking a survivin promoter and a polynucleotide encoding an active Granzyme B. As noted above for the recombinant nucleic acid molecules according to the invention, the survivin promoter and the coding region may be physically separated by 1,000 nucleotides or more, by less than 1,000 nucleotides, or by 100 nucleotides or less.

Another aspect of the invention is drawn to a method for treating a disorder, condition or disease characterized by cell hyperproliferation, such as a disorder, condition or disease selected from the group consisting of cancer, rheumatoid arthritis, systemic lupus erythematosus, Crohn's disease, ulcerative colitis, autoimmune hepatitis, systemic vascular hypertension, pulmonary hypertension, glomerulonephritis and multiple sclerosis, comprising administering an effective dose of a pharmaceutical composition as described above to an organism in need, thereby treating the disorder, condition or disease. An effective dose is determined on an individual basis by setting, such as by optimizing, known variables using routine procedures well known in the art. The organism in need may be any mammal, including domesticated animals, pets, zoo animals, and, preferably, humans. Embodiments involving the treatment of a cancer condition include methods wherein the cancer is selected from the group consisting of cancers of the lung, colon, breast, pancreas, prostate, ovary, or central nervous system, as well as a leukemia, a pediatric tumor (e.g., an embryonal tumor as distinct from an epithelial tumor as identified above), including a bone and a soft-tissue sarcoma (e.g., osteo, ewings, and rhabdomyosarcoma), and embryonal kidney tumor (e.g., Wilms, rhabdoid, renal cell), a liver tumor (e.g., hepatoblastoma, an embryonal sarcoma, a hepatocellular carcinoma), a head and neck squamous cell carcinoma, a neuroblastoma, a melanoma, thymoma, a prostate cancer, a lymphoma, an adenocarcinoma (e.g., of the pancreas, breast, and the like).

Still other embodiments, drawn to method of treating a disease, disorder or condition other than cancer include any disease, disorder or condition characterized by at least one type of hyperproliferative cell, such as a chronic inflammatory disease, including but not limited to, arthritis in any of its forms (e.g., rheumatoid arthritis), lupus erythematosus (e.g., systemic lupus erythematosus or SLE), inflammatory bowel disease (e.g., Crohn's disease, ulcerative colitis), liver disease (e.g., autoimmune hepatitis), cardiovascular and pulmonary diseases (e.g., systemic vascular hypertension, pulmonary hypertension), renal diseases (e.g., glomerulonephritis), and multiple sclerosis.

Yet another aspect of the invention is a method for ameliorating a symptom of a cancer condition comprising administering an effective dose of a pharmaceutical composition as described herein. Amelioration of any symptom known to be associated with a cancer condition is contemplated, including amelioration of physical discomfort, e.g., pain, attributable to the presence of a tumor.

Still another aspect of the invention is drawn to a kit comprising the pharmaceutical composition described herein and a set of instructions for the administration thereof. The set of instructions can be one or more directive or suggestions, and can be provided in any form, including a separate document such as a pamphlet, or a container label.

A further aspect of the invention is drawn to a use of a recombinant nucleic acid molecule of the invention in the preparation of a medicament for the treatment of a disease selected from the group consisting of hyperproliferative cell diseases, such as a chronic inflammatory disease, including but not limited to, arthritis in any of its forms (e.g., rheumatoid arthritis), lupus erythematosus (e.g., systemic lupus erythematosus or SLE), inflammatory bowel disease (e.g., Crohn's disease, ulcerative colitis), liver disease (e.g., autoimmune hepatitis), cardiovascular and pulmonary diseases (e.g., systemic vascular hypertension, pulmonary hypertension), renal diseases (e.g., glomerulonephritis), and multiple sclerosis. A related aspect of the invention provides for a use of a recombinant nucleic acid molecule of the invention in the preparation of a medicament for the amelioration of a symptom associated with, or the palliative treatment of, a disease selected from the group identified immediately above.

Numerous additional aspects and advantages of the invention will become apparent to those skilled in the art upon consideration of the following detailed description of the invention, which describes presently preferred embodiments thereof.

DETAILED DESCRIPTION

Figure 1:
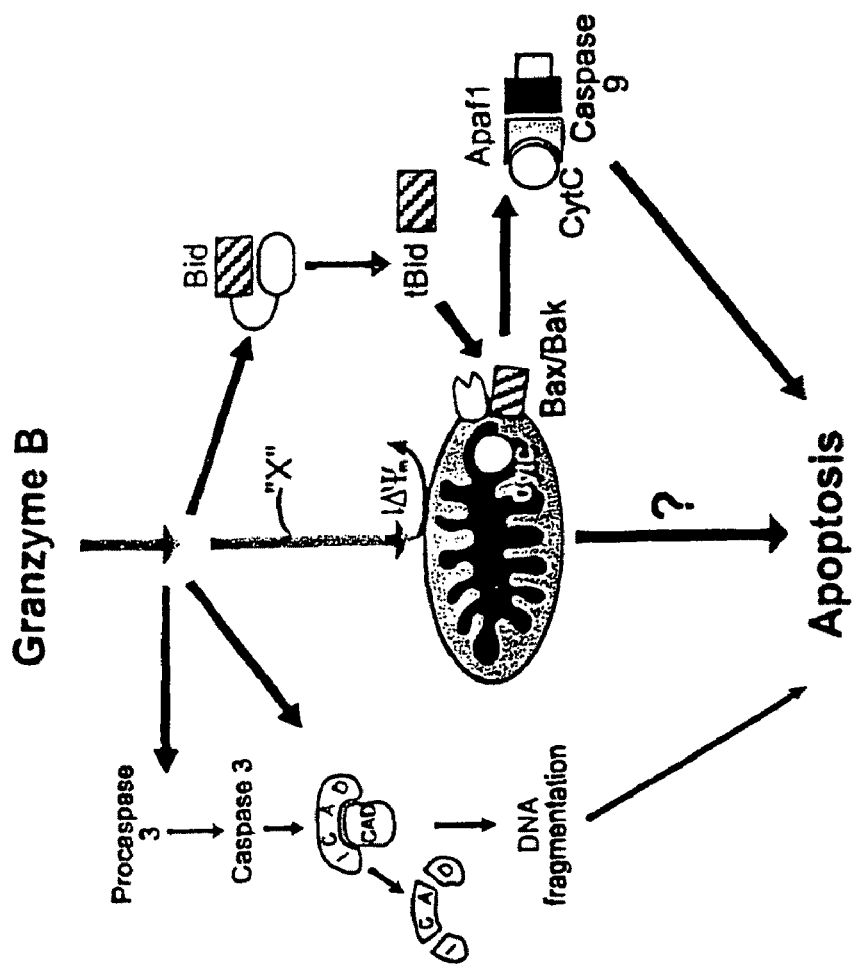
FIG. 1 shows a schematic illustration of biochemical pathways affected by Granzyme B action.
Figure 2:
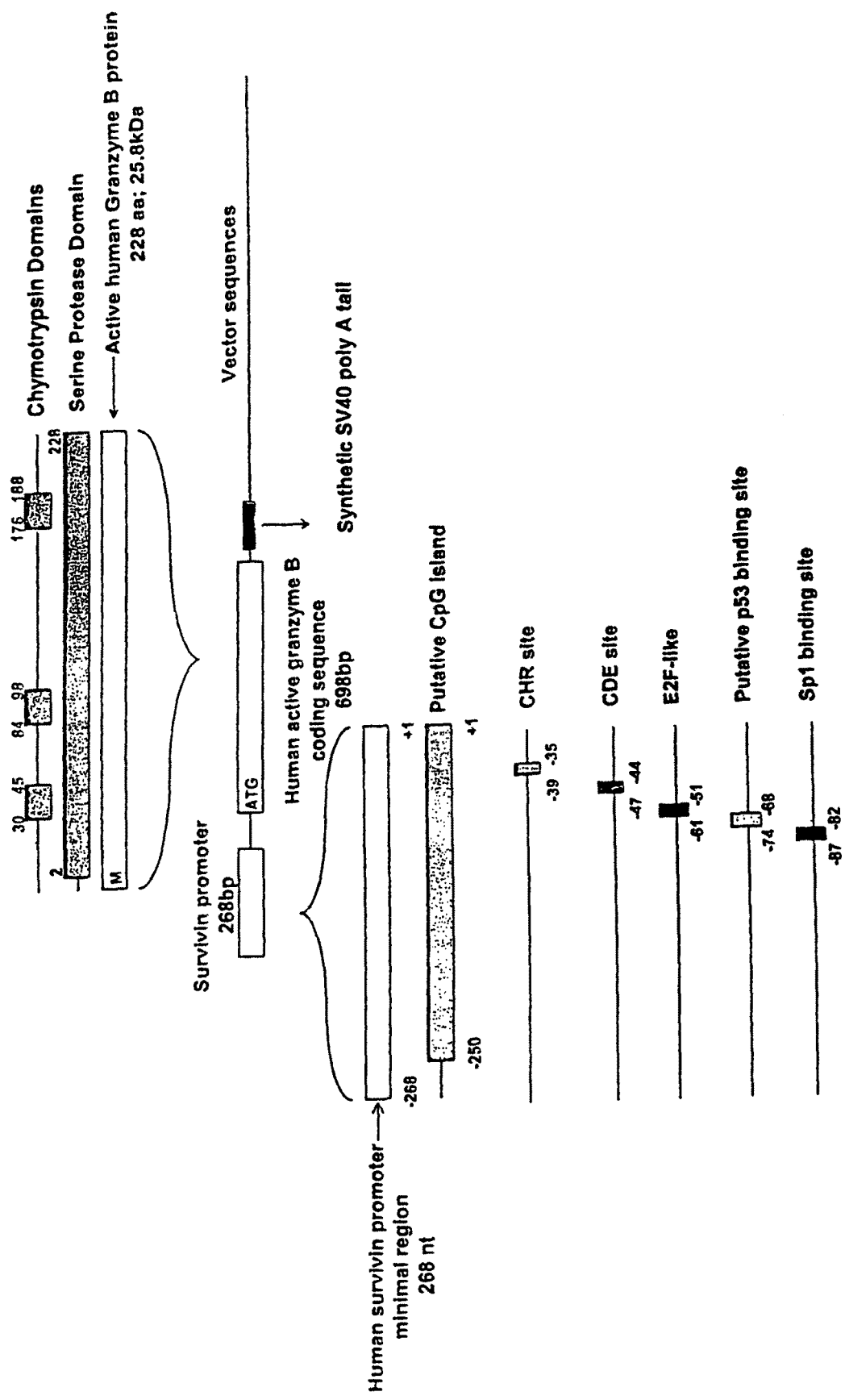
FIG. 2 illustrates a schematic map of the SAGA construct, including selected coordinates for the regions encoding the full-length and active forms of Granzyme B and significant regions of the survivin promoter.

The invention provides recombinant constructs that operatively link an inhibitor of apoptosis protein (IAP) expression control element and the coding region for a cytotoxic/cytolytic agent, such as an apoptosis-inducing protein, or AIP. Endogenous IAP expression control elements are responsible for relatively low-level expression of IAPs in certain cells, with expression at undetectable levels in other cells. Survivin, an exemplary member of the inhibitor of apoptosis (IAP) family of proteins, is widely expressed in transformed cell lines and in many different primary cancer cells, including both hematopoietic and non-hematopoietic malignancies. See, e.g., Yang et al., Gene Ther. 11(15):1215-1223 (2004), incorporated by reference herein in its entirety. It is not detectably expressed in many non-malignant adult tissues, but is essential for fetal development, as demonstrated by conventional gene-targeting experiments in mice that show embryonic lethality at day 4-6 of development. In adult cancers, including lymphoma and many epithelial carcinomas (colon, breast, gastric) the expression level of Survivin, as assayed by immunohistochemical analysis and RT-PCR, correlates with overall survival. These IAP expression control elements, as typified by the survivin promoter, are disclosed as sufficient to drive expression of cytotoxic/cytolytic agents at levels sufficient to result in cell death in primary cancer cells, while maintaining expression levels in non-cancerous cells at levels compatible with cell survival. As such, the materials and methods of the invention provide a fusion of suicide gene therapy and immunotherapy. A preferred form of the constructs according to the invention is a recombinant nucleic acid molecule having an IAP expression control element in operable linkage to a coding region for a cytotoxic/cytolytic agent, which may then be introduced to desired cells through targeted or non-targeted delivery mechanisms known in the art.

The materials and methods of the invention provide several advantages over existing methodologies for treating disease, such as cancer. Firstly, the expression control element of an IAP, such as a Survivin promoter, is relatively silent in healthy tissues, i.e., it is not sufficiently activated to potentiate significant (detectably deleterious levels) cell death in the few tissues that express it at low detectable levels. This is an attractive feature, as it would be expected to confer minimal toxic side effects. Survivin is also known to be expressed at very high levels in the majority of human malignancies, representing an additional attraction for Survivin-mediated, and other IAP-mediated, therapies. The effectiveness of the invention is demonstrated by the beneficial effect shown in treating a wide variety of tumor cells in vitro, with a demonstrated correlation of the in vitro results to in vivo results. These beneficial results, moreover, are achieved by engineering IAP expression control elements to have an effect wholly unlike their natural effects by linking them to AIP coding regions in contrast to the natural linkage to IAP coding regions. The beneficial effects of such constructs, as disclosed herein, also avoided any expression control influences that may have been provided by, e.g., the native (IAP) coding regions or encoded products (or the AIP coding regions or encoded products) to produce operative, beneficial constructs for use in treating a variety of diseases amenable to treatment focused on cell destruction, as well as for amelioration of a symptom associated with any such disease.

A preferred feature of the methodology in embodiments employing the activity of Granzyme B is the use of the active form of human Granzyme B and not the inactive zymogen. This presents an advantage over some gene therapy approaches as it is a human protein and it eliminates the need for treatment with a prodrug, a required component in many suicide gene approaches currently available (44, 45). In exemplary embodiments of the invention, intraperitoneal delivery of SAGA complexed to linearized polyethyleneimine (L-PEI) results in Survivin-specific expression of human Granzyme B exclusively within the tumor, making it a powerful, tumor-specific agent. SAGA's molecular mechanism of action is based on that of Granzyme B activity, but by using this method a number of obstacles encountered with current CTL-mediated therapy are bypassed, including avoidance of most tumor evasion mechanisms.

Granzyme B can promote activation of members of the caspase family of cysteine proteases through proteolytic processing of several members of this family. Granzyme B can also promote caspase activation indirectly, through proteolysis of the Bcl-2 family protein, Bid (46). Proteolysis of Bid by Granzyme B results in the release of mitochondrial cytochrome C into the cytosol (47). Cytochrome C efflux from mitochondria then leads to the engagement of the apoptosome pathway and ultimately to programmed cell death (48). Studies using purified Granzyme B suggest that nanomolar amounts of this enzyme are sufficient to engage the target cell death machinery (49). Ultimately, Granzyme B triggers a two-tiered apoptotic cascade involving at least seven caspases, with caspase-3 playing a major role (13). By unleashing Granzyme B in Survivin-expressing tumor cells in some embodiments of the invention, multiple pathways of apoptosis (e.g., the caspase-3 pathway, mitochondrial potential, and activation of ICAD (Inhibitor of caspase-activated DNase) are effectively activated within a tumor, a unique aspect of this single-agent therapy. As a consequence of SAGA treatment, Survivin-expressing cells are specifically targeted, leading to Survivin-specific downstream effects, including a decrease in cell proliferation and an increase in programmed cell death. The multiple molecular effects of SAGA alone resulted in a significant decrease in tumor size, tumor weight and number of tumor nodules, as well as a complete clinical remission in 3 of 15 (20%) treated animals. Strikingly, 95% of tumors isolated from SAGA-treated mice were localized to the injection site, suggesting that treatment with SAGA greatly diminishes intraperitoneal dissemination of the disease. These results are consistent with a potential role for the invention in the treatment of early as well as late stage ovarian disease.

Results presented herein also demonstrate an additive, or even synergistic, cell growth inhibitory effect of SAGA and paclitaxel in ovarian tumors in vivo. From a molecular standpoint, paclitaxel acts by inducing a G2/M block in tumor cells through promotion and stabilization of microtubule assembly (50, 51). Accumulation of tumor cells in G2/M is believed to induce an increase in Survivin expression at the transcriptional level, via the CDE/CHR domains in its promoter. An additional mechanism has been observed in which Survivin promoter activity is increased by paclitaxel immediately prior to an arrest in G2/M. Paclitaxel is therefore a logical choice for combination therapy with SAGA. A significant increase in complete clinical remission and decrease in tumor growth was observed following treatment in vivo with paclitaxel and SAGA in combination.

As demonstrated herein, the invention provides a potent tumor-targeted therapeutic approach in an intraperitoneal ovarian carcinoma tumor model. The combined anti-tumorigenic and anti-metastatic properties observed here lead to the expectation that the invention will prove usefully efficacious in treating or ameliorating a wide variety of cancers, including ovarian cancers. Preferred applications for the invention would be any cancer associated with the expression of an IAP gene at high levels, such as Survivin.

The SKOV-3 intraperitoneal model exemplified herein is an ideal animal study model for biotherapy research in ovarian carcinoma, as it simulates the intraperitoneal disseminating behavior of human ovarian carcinoma. The results establish that by manipulating an expression control element of an IAP, such as the human Survivin promoter, to drive expression of a cytotoxic gene product, such as an apoptotic gene product like the active form of human Granzyme B, therapeutics are provided that effectively inhibit intraperitoneal ovarian tumor growth and, strikingly, diminish intra-abdominal metastatic dissemination.

To facilitate a more thorough understanding of the invention, the following term definitions are provided.

"Inhibitor of apoptosis protein," or IAP, is any one of a member of a protein family known to inhibit the apoptotic process. Such proteins are found in any of a variety of animals, including humans. The human members of the family include, but are not limited to, HIAP1, HIAP2, XIAP, NAIP and Survivin.

"Apoptosis-inducing protein," or AIP, is any one of a member of a protein family known to be capable of contributing to the induction of apoptosis in at least one cell type. An exemplary member of this protein family is human Granzyme B, a serine protease. See, e.g., Trapani et al., Curr. Opin. Immunol. 15(5):533-43 (2003) and Lord et al., Immunol. Rev. 193:31-38 (2003), both incorporated by reference herein in their entireties. Members of this family of proteins are found in a variety of animals, and other members of the family include Granzyme A, as well as Granzymes H, K, and M (man), Granzymes C, D, E, F, G and K (mouse), and Granzymes C, I J, K, and M (rat). AIPs also include variants and fragments of full-length AIPs as described herein. In addition to the AIP family of proteins, the invention comprehends any cytotoxic or cytolytic coding region product known in the art, including Cathepsin; Granulysin; Hemolysin; Amoebapores A, B, and C; Cytosine Deaminase; Uracil Phosphoribosyltransferase; and Thymidine Kinase. These coding region products may function alone, or in conjunction with other compounds, such as 5-fluoro-cytosine for use with Cytosine Deaminase or gancyclovir for use with Thymidine Kinase. In the latter context, it is understood that the cytotoxic/cytolytic agent results from the combination of the expressed product and the compound.

"Promoter region" is a nucleic acid capable of detectably binding an RNA polymerase enzyme. The promoter regions according to the invention, such as the full-length survivin promoter (SEQ ID NO:1; see also Table 1) or fragment thereof (e.g., nucleotides 68-268 of SEQ ID NO:1), exhibit a sequence associable with an expression control function, regardless of whether that expression control function facilitates the modulation of expression within a given cell type or leads to differing levels of expression in different cell types, or both.

"Operatively linked" means functionally linked and, in the context of the invention, refers to linkage of an expression control element to a coding region such that expression of the coding region is capable of being influenced by the expression control element in at least one cancer cell type.

"Coding region" is given the ordinary meaning it has acquired in the field of a nucleic acid region encoding an expression product which is typically a peptide or polypeptide.

"SAGA" generally refers to the materials and methods of the invention, including a recombinant nucleic acid molecule having an inhibitor of apoptosis protein (IAP) promoter region operatively linked to a coding region for an active form of a cytotoxin/cytolytic agent such as an apoptosis-inducing protein, as well as methods for administering such a molecule to treat a condition or disease such as cancer, and a method to ameliorate a symptom of such a disease or disorder. Expressing SAGA specifically in tumor cells emulates, in part, cytotoxic natural killer T cells (NK cells) and T-lymphocyte (CTL) activities, whereby, e.g., the native CTL-Granzyme B protein initiates programmed cell death through multi-modal, non-overlapping molecular pathways from within the cancer cell. In a preferred embodiment, the material is a construct containing a survivin promoter region operatively linked to a coding region for an active form of Granzyme B, from which the acronym is derived. Depending on context, the term "SAGA" is used broadly to refer to the materials and methods of the invention, or to refer to materials and methods relating to embodiments involving the survivin promoter region operative linked to the coding region for an active form of Granzyme B.

"Pharmaceutical composition" is a composition formulated in a manner that renders it suitable for administration by at least one route to an animal such as a human. Typically, pharmaceutical compositions contain a pharmaceutically active agent in combination with a pharmaceutical carrier, diluent and/or excipient known in the art.

TABLE 1

| SEQ ID | SEQ TYPE | Description | Active Portion (Nt or aa residues) | Accession no. |
|---|---|---|---|---|
| 1 | DNA | Survivin promoter (human) | 795-1062 (68-268 | AY795969 SEQ ID NO: 1) |
| 2 | DNA | Granzyme B (human) | | |
| 3 | DNA | Granzyme B (human) | 122-810 | NM_004131 |
| 4 | AA | Granzyme B (human) | 19-247 | |
| 5 | DNA | Granzyme B variant (human) | | AY232654 |
| 6 | AA | Granzyme B variant (human) | 7-235 | |
| 7 | DNA | Granzyme B (mouse) | | NM_013542 |
| 8 | AA | Granzyme B (mouse) | 19-247 | |
| 9 | DNA | Granzyme B (rat) | | NM_138517 |
| 10 | AA | Granzyme B (rat) | 19-248 | |
| 11 | DNA | Granzyme B (woodchuck) | | AY253727 |
| 12 | AA | Granzyme B (woodchuck) | | |
| 13 | DNA | Granzyme B (cow) | | NM_174296 |
| 14 | AA | Granzyme B (cow) | 18-251 | |
| 15 | DNA | Granzyme B (chimp) | 122-922 | ensemble ID |
| 16 | AA | Granzyme B (chimp) | 21-247 | |
| 17 | DNA | Granzyme B (zebrafish) | 135-669 | ensemble ID |
| 18 | AA | Granzyme B (zebrafish) | | |
| 19 | DNA | Granzyme B (chicken) | 138-678 | ensemble ID |
| 20 | AA | Granzyme B (chicken) | 3-225 | |
| 21 | DNA | Granzyme B (puffer fish) | 182-735 | ensemble ID |
| 22 | AA | Granzyme B (puffer fish) | | |
| 23 | DNA | Granzyme A (human) | | BC015739 |
| 24 | AA | Granzyme A (human) | | |
| 25 | DNA | Granzyme C (mouse) | | NM_010371 |
| 26 | AA | Granzyme C (mouse) | | |
| 27 | DNA | Granzyme D (mouse) | | NM_010372 |
| 28 | AA | Granzyme D (mouse) | | |
| 29 | DNA | Granzyme E (mouse) | | NM_010373 |
| 30 | AA | Granzyme E (mouse) | | |
| 31 | DNA | Granzyme F (mouse) | | NM_010374 |
| 32 | AA | Granzyme F (mouse) | | |
| 33 | DNA | Granzyme G (mouse) | | NM_010375 |
| 34 | AA | Granzyme G (mouse) | | |
| 35 | DNA | Granzyme K (mouse) | | NM_008196 |
| 36 | AA | Granzyme K (mouse) | | |
| 37 | DNA | Granzyme H (human) | | BC027974 |
| 38 | AA | Granzyme H (human) | | |
| 39 | DNA | Granzyme K (human) | | BC035802 |
| 40 | AA | Granzyme K (human) | | |
| 41 | DNA | Granzyme M (human) | | BC025701 |
| 42 | AA | Granzyme M (human) | | |
| 43 | DNA | Granzyme C (rat) | | NM_134332 |
| 44 | AA | Granzyme C (rat) | | |
| 45 | DNA | Granzyme J (rat) | | U72143 |
| 46 | AA | Granzyme J (rat) | | |
| 47 | DNA | Granzyme K (rat) | | NM_017119 |
| 48 | AA | Granzyme K (rat) | | |
| 49 | DNA | PCR Primer (Gran-Nco) | | |
| 50 | DNA | PCR Primer (Gran-Xba) | | |

"Pharmaceutical carrier" is at least one compound that renders a composition suitable for administration to an animal such as a human. Any carrier known in the art may be used in the pharmaceutical compositions according to the invention.

"Effective dose" is understood in the art as that amount of a compound or substance that is capable of producing a beneficial effect in an organism to which the compound or substance is administered. An effective dose will depend on many variables, all known in the art, such as the general health and weight of the organism, the severity of the condition or disease, and the like. An effective dose is determined on an individual basis using routine procedures and is within the skill in the art.

"Ameliorating a symptom" means to reduce or lessen the severity of a symptom, such as pain, limited mobility, physiological dysfunction, and the like.

"Set of instructions" means a collection of one or more directives for the safe and efficacious administration, or other use, of a compound or composition according to the invention, such as a pharmaceutical composition. Any form known in the art may be used to provide the set of instructions.

The materials and methods disclosed herein are expected to be useful in treating any vertebrate animal, with specific contemplation of treating any mammal, including the treatment of any domesticated livestock, pet, zoo animal, or human, with a human being the preferred subject for treatment (including methods for ameliorating a symptom of a cancer). Further the invention comprehends treating any of a variety of cancers including the treatment of tumors (e.g., malignant tumors). The materials and methods are further expected to be useful in ameliorating a symptom associated with any such cancer and to be useful in preparing a medicament for the treatment of such a cancer or the amelioration of a symptom associated therewith. Exemplary tumors include, but are not limited to, central nervous system tumors (e.g., glioblastoma, astrocytoma, medulloblastoma), hepatic, gastric, pancreatic, breast, lung, ovarian, cervical carcinomas, sarcomas, head and neck tumors, prostate tumors, melanomas, lymphomas, and acute and chronic leukemias.

The constructs according to the invention may be delivered using any delivery route known in the art, including injection intratumorally, intramuscularly, intravenously, intrathecally, subcutaneously, and intraperitoneally, with intratumoral delivery being preferred. Other routes, such as topical administration, are also contemplated. In addition, any delivery vehicle known in the art is contemplated for use in the methods disclosed, including the use of a vector, such as a plasmid (eukaryotic plasmids, shuttle plasmids, wide-host-range plasmids, and the like), phagemid, virus (e.g., adenovirus, adeno-associated virus, herpesvirus, vaccinia virus, lentivirus, oncovirus), and phage. Also contemplated is the delivery of linear, single- or double-stranded nucleic acid (DNA, RNA, or a mixture), the use of protonics (proton sponge—jetPEI, the use of the antennapedia homeodomain, lipid-mediated delivery (e.g., liposomes), PEG, or any other approach known in the art.

The chimeric construct for targeting expression of a cytotoxin or cytolytic agent to cancer cells comprises an expression control element in operative linkage to the coding region for a cytotoxic expression product. The expression control element is any regulable or controllable element known to be controllably functional in at least one cancer cell type. A preferred expression control element is a promoter, which is a nucleic acid containing an RNA polymerase binding region and an expression control domain, and may contain additional elements. Suitable promoters are promoters for any of the IAP proteins found in mammals, as well as homologs and variants thereof. An exemplary expression control element is the survivin promoter from a mammalian species, and preferably the human survivin promoter, which preferably includes the 200 bp spanning nucleotides 68-268 of SEQ ID NO:1 (containing a CpG island), but may include the 268 bp of SEQ ID NO:1, alone or in combination with flanking sequence(s).

The coding region for an expressible cytotoxin/cytolytic agent may be any such coding region known in the art. Specifically contemplated by the invention are coding regions for the full-length or active forms, where applicable, of Granzyme B, Granzyme A, Granulysin, Cathepsin W, Cathepsin G, Cytosine deaminase, Thymindine kinase, *E. histolytica* amoebapore, Hemolysin, and Uracil Phosphoribosyltransferase. The invention contemplates coding regions from any known source, including any mammalian source or synthetic construction.

Variants of the expression control element or coding region for the cytotoxin/cytolytic agent are also contemplated. The variants are at least 90%, and preferably 99%, identical to one of the aforementioned elements (expression control element or coding region for a cytotoxin/cytolytic agent), or that hybridizes to one of those elements under stringent hybridization conditions of 0.015 M sodium chloride, 0.0015 M sodium citrate at 65-68° C. or 0.015 M sodium chloride, 0.0015M sodium citrate, and 50% formamide at 42° C. The variants of the expression control element retain the capacity to bind RNA polymerase and to drive expression of a coding region in a diseased cell such as a cancer cell; the coding region variants encode a polypeptide that retains an apoptosis-inducing function.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015 M sodium chloride, 0.0015 M sodium citrate at 65-68° C. or 0.015 M sodium chloride, 0.0015M sodium citrate, and 50% formamide at 42° C. See Sambrook et al., *Molecular Cloning: A Laboratory Manual*, 2$^{nd}$ Ed., Cold Spring Harbor Laboratory, (Cold Spring Harbor, N.Y. 1989).

More stringent conditions (such as higher temperature, lower ionic strength, higher formamide, or other denaturing agent) may also be used, however, the rate of hybridization will be affected. In instances wherein hybridization of deoxyoligonucleotides is concerned, additional exemplary stringent hybridization conditions include washing in 6×SSC 0.05% sodium pyrophosphate at 37° C. (for 14-base oligos), 48° C. (for 17-base oligos), 55° C. (for 20-base oligos), and 60° C. (for 23-base oligos).

In addition, the invention comprehends fragments of the above-identified expression control elements or coding regions for cytotoxin/cytolytic agents, provided that an expression control element fragment retains the activity or controllably driving expression and a cytotoxin/cytolytic agent coding region fragment encodes a polypeptide that retains the capacity to kill a cell in which it is expressed at the level expected from the expression control element operatively linked to its coding region. Further, where an expression control element contains a CpG island domain, such as in the survivin promoter, a fragment thereof will preferably retain that domain. Analogously, for a cytotoxin/cytolytic agent that exhibits serine protease activity, the coding region for a fragment thereof will preferably encode a polypeptide retaining the known active site for such activity. Additionally, fragments of Granzyme B preferably include the active site for serine protease activity.

The operable linkage of the expression control element and the coding region for the cytotoxin/cytolytic agent would be recognized by one of skill in the art as any placement, adjacent or at some distance (e.g., 1,000 nucleotides or more, but preferably 100 nucleotides or less), and any relative orientation that is understood as being compatible with the controlled expression of the encoded expression product in at least one cancer cell. In embodiments involving the survivin promoter, for example, that promoter is preferably oriented head-to-tail with the coding region and is located within 1-100 nucleotides of the coding region.

Example 1

The materials and methods of the invention exploit the high expression levels of an inhibitor-of-apoptosis (IAP) gene, such as survivin, in malignant cells, in which the IAP (e.g., survivin) promoter is used to drive the expression of an apoptosis-inducing gene, or AIG, to kill cancer cells by programmed cell death. Some embodiments provide perforin-independent Granzyme B cytotoxicity and therefore do not require pro-drug activation; these embodiments have been termed SAGA, for survivin and Granzyme B apoptosis. In this Example, the suitability of the materials and methods for treating leukemia is demonstrated.

Jurkat cells were used as an in vitro model for T-cell leukemia, and 697Bcl2 cells provided a model for B-lineage Bcl2-expressing leukemia cells. The results establish that the materials and methods disclosed herein are more efficient in killing leukemic cells than conventional chemotherapy, indicating that the invention is useful in treating leukemias, including acute lymphoblastic leukemias (e.g., T-ALL and B-ALL).

A. Chimeric Construct, SAGA

The pDRIVE survivin (Invivogen) construct was digested with BspHI and NheI to excise the survivin promoter. Active granzyme B cDNA was amplified with primers A (SEQ ID NO:49) and B (SEQ ID NO:50), containing linkers for NcoI and XbaI restriction sites, respectively. PCR was performed with Amplitaq Gold DNA polymerase (Perkin Elmer) in a total volume of 50 µl. The reaction mixture was subjected to 35 cycles of amplification with annealing at 55° C. for 40 seconds, denaturation at 94° C. for 40 seconds, and extension at 72° C. for 50 seconds. The resulting PCR fragment was digested with NcoI and XbaI, resolved on a 1% agarose gel, and purified using a Qiagen Gel extraction kit.

The resulting cDNA fragment was ligated to digested pDRIVE survivin using T4 ligase for 5 minutes at room temperature. The ligation mixture was used to transform *Escherichia coli* DH5α competent cells and plated on TB-Zeo agar plates. Resulting colonies were screened by restriction digestion, and potential clones were confirmed by automated sequencing. The resulting clone consists of the survivin promoter fused to the coding sequence of an active Granzyme B, followed by the SV40 polyadenylation signal. The resulting clone was designated SAGA.

Endotoxin-free DNA from pDRIVE survivin and SAGA were prepared using Qiagen EndoFree Maxiprep kit for all further experiments.

B. Cell Lines and Transfections

Acute T-cell leukemia cells, Jurkat, were grown in RPMI-1640 (Mediatech) supplemented with 10% FBS and grown at 37° C. in 95% air, 5% CO2. For growth analysis, cells were seeded at a density of $2 \times 10^5$ cells and for all other experiments a density of $5 \times 10^5$ was used. Transfections were performed using effectene transfection reagent, at a ratio of 1 µg DNA:25 µl effectene. Vincristine sulfate was used at a concentration of 2 µM, which represents the standard serum concentration used to induce apoptosis in tumor cells in culture.

C. Microscopic Analysis

Living cells in 12-well plates were photographed under phase contrast using a Leica Inverted microscope at 10× magnification.

D. Mitochondrial Potential

To measure mitochondrial potential from the different experimental conditions, cells were loaded with 10 µg/ml JC1 ((5,5',6,6'-tetrachloro-1,1',3,3'-tetraethylbenzimidazolylcarbocyanine iodide; Molecular Probes) for 15 minutes, at 37° C. and 5% $CO_2$. The cells were washed with phosphate-buffered saline (PBS) twice, and diluted to 300 µl in PBS. Analysis was performed by Fluorescent-activated cell sorting (FACS).

E. Annexin V

To analyze early apoptotic events, cells from the different experimental conditions were subjected to staining with an Annexin V-FLUOS kit (Roche). FACS analysis was then performed.

F. Cell Viability and Late Apoptosis/Necrosis

To determine cell viability, cells were subjected to trypan blue exclusion assays. Briefly, cells were washed with PBS, and diluted 1:1 in a solution of 0.4% trypan blue. Viable cells were counted and total viable cell number was used for growth curves. Late apoptotic/necrotic cells were also identified by staining with 0.4% trypan blue. The number of apoptotic/necrotic cells were counted and expressed as a percentage of the total number of cells.

G. DNA Fragmentation

To analyze DNA fragmentation, cellular DNA was isolated by lysis of cells in Cell Lysis Buffer (50 mM Tris-HCl, pH 8.5, 20 mM EDTA, 1% NP-40 (IGEPAL CA-630)) for 30 minutes on ice, followed by a 1 hour incubation at 56° C. with 500 µg/ml RNase A (Roche) and an overnight incubation with 1 mg/ml proteinase K (Fisher) at 37° C. After allowing the solution to cool to room temperature, proteins were precipitated with Protein precipitation solution (Gentra Systems) and isopropanol was added to the supernatants containing DNA to precipitate that DNA. The resulting RNase-treated DNA was quantified by spectrophotometry and 5 µg of DNA were resolved in a 1.8% agarose gel at 80V for 2 hours. DNA was stained by ethidium bromide and visualized with a UV transilluminator. A 1 kB Plus DNA ladder (Fisher) was run alongside the samples.

H. Western Blot

Proteins were extracted from cells by boiling in 0.5% SDS. Quantification of the protein content of the cell lysates was determined using the Lowry method. A total of 15 µg of each cell lysate were analyzed through electrophoretic separation in 12% SDS-PAGE and transferred onto a nitrocellulose membrane using a semi-dry transfer apparatus, at 20V for 1 hour. The membrane was probed with rabbit anti-caspase-3 polyclonal antibody (1:1000, Santa Cruz Biotech), rabbit anti-granzyme B (1:1000, Abcam) or mouse anti-p21 (1:1000, Santa Cruz Biotech) and HRP-conjugated anti-rabbit or anti-mouse IgG (1:5000, Santa Cruz Biotech). Detection was achieved using the ECL or ECL Advanced kits (Amersham) and exposure to X-ray film for varying amounts of time. Protein standards were used for size determination.

I. Expression of Granzyme B in Jurkat Cells

Proliferating Jurkat cells were transfected with the survivin promoter-granzyme B construct disclosed herein and termed SAGA, for 24 or 48 hours. Protein extracts were generated from transfected cells and control transfected cells, and analyzed by SDS-PAGE. A protein band corresponding to the size of active Granzyme B was detected faintly at 24 hours and marginally stronger at 48 hours, thus demonstrating the successful expression of Granzyme B from SAGA.

J. Granzyme Activity (Caspase 3)

After confirming expression of Granzyme B from SAGA, its apoptotic function was tested by assaying for caspase-3 activation. Proliferating Jurkat cells were transfected with SAGA for 24 or 48 hours, as previously described. Protein extracts were separated by SDS-PAGE. Successful caspase-3 activation was observed in SAGA-transfected cells as demonstrated by a decrease in procaspase-3 and an increase in active caspase-3, compared to control transfected cells at both 24 and 48 hours.

K. Growth of Saga-Transfected Cells is Impaired

Since SAGA-expressed Granzyme B was shown to be an active, proapoptotic agent, its effects on the growth of Jurkat cells in culture were examined and compared to the commonly used chemotherapy drug, vincristine (VCR). Proliferating Jurkat cells were seeded at a density of $2 \times 10^5$ cells and transfected with control plasmid, SAGA, or treated with $2 \mu M$ VCR. Viable cells were assayed by trypan blue exclusion at 0, 12, 24, 48 and 72 hours post-transfection/treatment. There was a small decrease in the viability of all cells, including controls, at 12 hours due the effectene treatment. Control cells recovered by 24 hours and grew consistently, with a doubling time of approx 24 hours. In contrast, VCR-treated cells had a small increase in growth at 24 hours, but by 48 hours, there was a decrease in cell number compared to time 0 that persisted through 72 hours. SAGA-transfected cells exhibited a continuous decrease in cell number over all time points, with the final living cell count at 72 hours representing 30% of the initial cell number at time 0. This is compared to 63% of living cells for VCR-treated cells and 223% of living cells for control cells.

L. Morphological Changes

SAGA transfected, VCR treated, and control cells were visualized microscopically at 0, 12, 48 and 72 hours post transfection/treatment. At 0 hours, the cells in all groups appeared healthy. At 12 hours, there was approximately 5% apoptosis seen in both SAGA- and VCR-treated cell populations. At 48 and 72 hours, more than 50% of apoptotic cells in SAGA- and VCR-treated cell populations were visualized, with a very high degree of morphologically abnormal cells in the population of cells transfected with SAGA, including late necrotic and lysed cells, appearing as cellular debris.

M. Apoptosis

Granzyme B is actively involved in NK- and CTL-mediated apoptosis, which led to a comparative investigation of the different stages of apoptosis in SAGA-transfected cells and VCR-treated cells.

1. Early Apoptosis

Annexin-V/PI is a commonly used method to detect early apoptotic events in cells. We employed this strategy to assay early apoptosis in SAGA transfected cells at 12, 24 and 48 hours. The levels of early apoptosis in these cells were higher than in control cells, but usually lower than VCR treated cells, suggesting that apoptosis in SAGA transfected cells progressed quickly.

2. Mitochondrial Potential

Granzyme B has been implicated in mitochondrial-dependent apoptosis both in vitro and in vivo. It has been reported that as a result of Granzyme B activity, there is a decrease in mitochondrial potential to allow the release of factors like Cytochrome C and AIF into the cytoplasm/nucleus, which are important events in mitochondrial-dependent apoptosis. To assay for changes in the mitochondrial potential, cells from the different experimental conditions were treated with the mitochondrial potential indicator dye JC1. The dye was incubated at $10 \mu g/ml$ in living cells at $37°$ C. for 15 minutes. After extensive washes, the cells were analyzed by FACS. A marked decrease in mitochondrial potential was observed in SAGA-transfected cells compared to control cells, as evidenced by the increase in intensity of green fluorescence and the decrease in intensity of red fluorescence, indicating the accumulation of the dye in the cytoplasm. Low mitochondrial potential is reflective of active apoptosis, and is associated with Granzyme B activity.

3. Late Apoptosis

Late apoptosis was quantified as the percentage of dead cells versus total cells. Dead cells were identified by trypan blue staining, which marked cells with compromised membranes, reflective of late-stage apoptosis. SAGA-transfected cells had higher levels of late-stage apoptosis at all time points evaluated. These results are in agreement with the microscopic observations that such cells showed a higher degree of morphologically abnormal cells and debris.

4. DNA Fragmentation

DNA fragmentation is a common sign of late-stage apoptosis that is characterized by enzyme-mediated nicks and breaks in the DNA. The enzyme is directly induced by Granzyme B. To determine whether Granzyme B expression from SAGA resulted in DNA fragmentation, DNA was extracted from transfected cells, RNase treated, and analyzed by agarose gel electrophoresis. The onset of DNA fragmentation occurred at 12 hours post-treatment for SAGA-treated cells. At 48 hours, DNA fragmentation was visible in both SAGA- and VCR-treated cells, but a higher percentage of fragmentation was observed in the SAGA-transfected cells. DNA from control cells remained intact throughout the experiment.

5. p21 Induction p21 protein expression is induced when cells receive an apoptotic stimulus, in cells with an intact p53 gene. p21 was detected in SAGA-transfected leukemia cells at 24 and 48 hours post-treatment. p21 was also induced in VCR-treated cells at 48 hours, albeit at much lower levels. The levels of p21 in control cells at both time points were negligible. These results further substantiate the occurrence of a higher degree of apoptosis in SAGA-transfected cells relative to VCR-treated cells and, perhaps more importantly, relative to control cells.

N. Combination Therapies

In addition to the single treatment effects of SAGA expression on transfected cells, the combined effects of treatment with SAGA plus VCR were also evaluated in vitro using Jurkat cells. A marked decrease in viability of cells receiving the combined treatment was observed relative to either treatment alone. The average viabilities were 86% for VCR-treated cells, 43% for SAGA-treated cells, and only 17% for cells receiving a combined treatment of SAGA and VCR, 48 hours after treatment. Rates of early and late apoptosis were synergistically increased for cells subjected to the combined therapy, as revealed by Annexin V and trypan blue staining, respectively, as well as a further decreased mitochondrial potential. DNA fragmentation was observed at the same level as for the single treatment of cells with SAGA. These results suggest that combination therapies provide a more aggressive approach to containing cell growth. Although not wishing to be bound by theory, these results are perhaps due to enhanced Granzyme B activity in the combined therapy analyzed.

Figure 4:
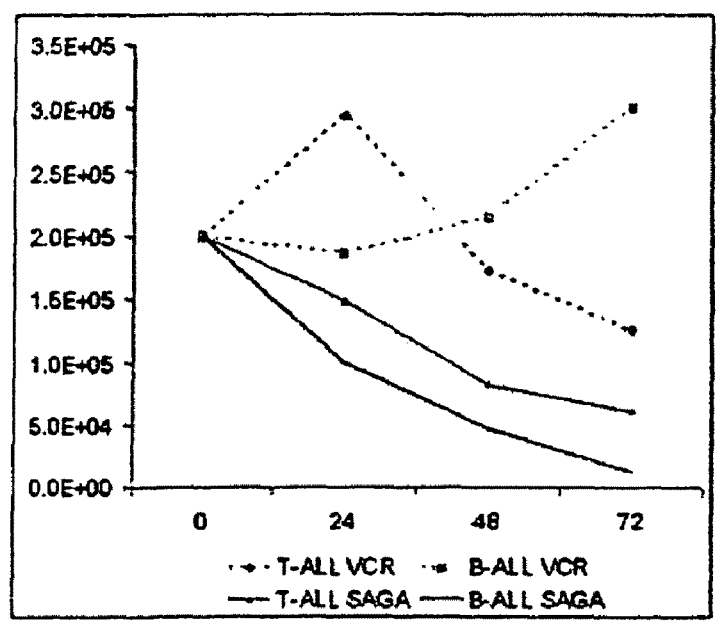
FIG. 4 shows growth curves of Jurkat cells and 697Bc12 cells.

The foregoing descriptions provide many working examples organized under a single example as an aid to the reader. Further, these descriptions emphasized the results obtained with Jurkat cells. In addition, however, 697Bcl2 cells were subjected to the same analyses (except for mitochondrial potential), with similar results except as noted below. These working examples establish that Jurkat cells responded to both vincristine therapy and SAGA, whereas 697Bcl2 cells were unaffected by normal serum concentrations of vincristine (151% of original inoculum at 72 hours), but responded to SAGA. Additionally, a minor response was observed in the form of cell growth containment when a high serum concentration of vincristine was used (5 µM). Growth curves of Jurkat cells and 697Bcl2 cells are shown in FIG. 4. At 72 hours, the percentage living cells exposed to a high dose of vincristine was 103% of the original inoculum, whereas only 52.3% of the original inoculum was present in SAGA-treated cells. By comparison, 189% of the original inoculum of control cells was found to be living at 72 hours. Furthermore, an additional chemotactic compound was tested, etoposide (used at a normal serum concentration of 5 µM), and it elicited a response in this cell line, although not as strong a response as that induced by SAGA administration. Etoposide-treated cells alive at 72 hours represented 61.8% of the original inoculum.

Figure 3:
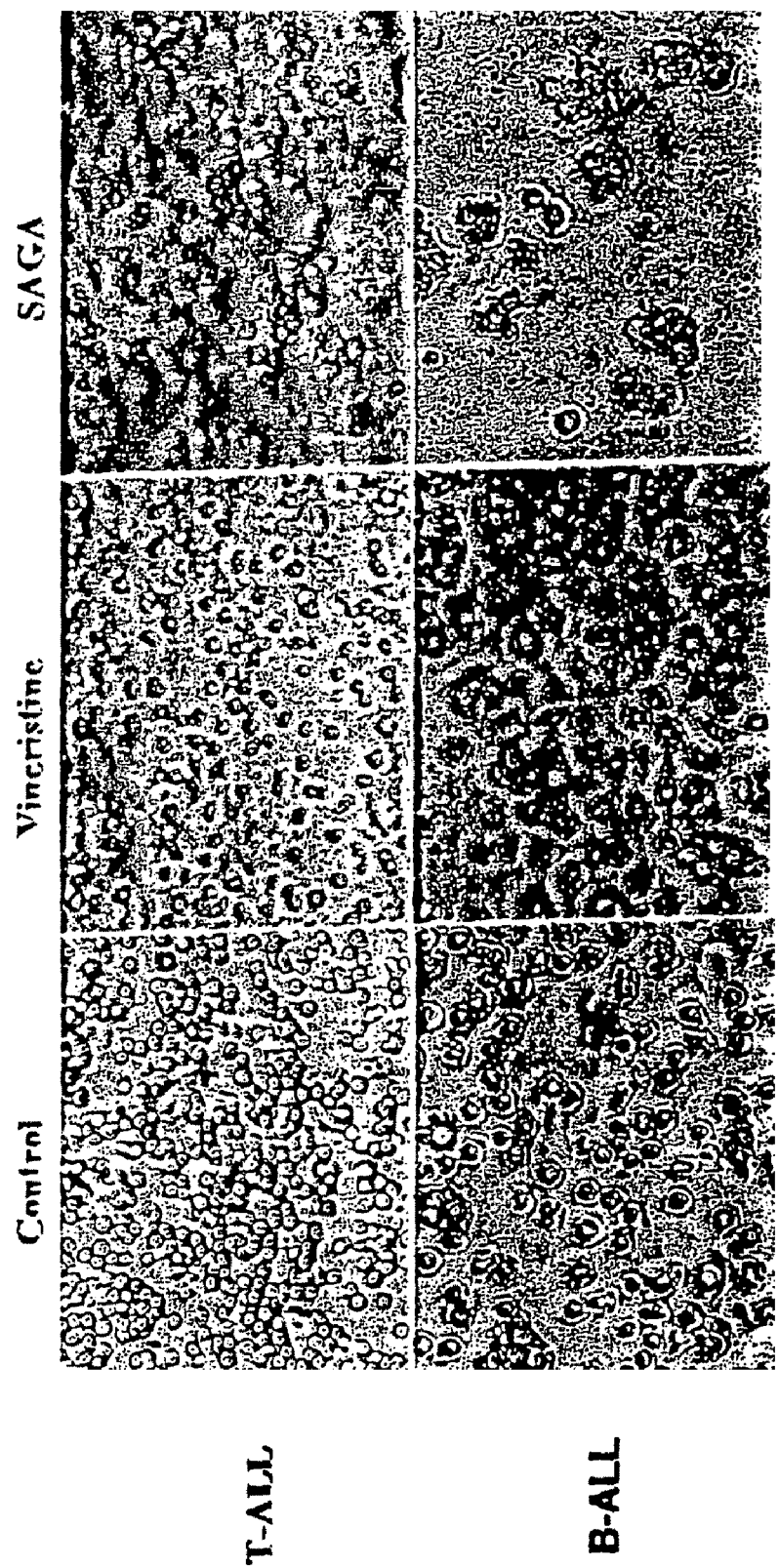
FIG. 3 provides photomicrographs illustrating the comparative morphology of leukemia cells containing, or lacking, SAGA.

Cell growth curves of Jurkat cells and 697Bcl2 cells revealed that the methods not only inhibited cell growth, they induced apoptosis. Apoptotic events were detected by Annexin V staining and by changes in mitochondrial potential, as early as 12 hours post-treatment. Rates of early apoptotic events are shown in Table 2. In addition to these events, DNA fragmentation was also observed and caspase-3 activation was evident in treated cells. Cytotoxicity was clearly visible by microscopic analysis 24 hours post-treatment (FIG. 3). The results indicate that survivin-driven AIP expression effectively enhanced cell death of leukemic blast cells derived from two common sub-types of ALL, one of which expresses the potent anti-apoptotic inhibitor, Bcl-2, known to be clinically more resistant to standard therapy.

TABLE 2

| | Early Apoptosis | | | Necrosis | | |
|---|---|---|---|---|---|---|
| | Control | Vincristine | SAGA | Control | Vincristine | SAGA |
| 24 hours | | | | | | |
| T-ALL | 2.09% | 46.5% | 41.1% | 2.11% | 18% | 18.6% |
| B-ALL | 1.19% | 1.78% | 29% | 0.44% | 1.17% | 30% |
| 48 hours | | | | | | |
| T-ALL | 6.34% | 49.4% | 66% | 6.04% | 26% | 11.3% |
| B-ALL | 2.97% | 5.09% | 29.1% | 1.45% | 2.34% | 54.1% |

Thus, the invention contemplates additive or combined therapies for the treatment of such diseases as cancer. The therapy provided by the expression of an apoptosis-inducing gene (AIG; e.g., the coding region for the active form of Granzyme B) driven by an expression control element from an IAP expression control region (e.g., a survivin promoter), may be combined with VCR therapy or any other therapy presently known in the art as therapeutically useful. The combined therapies may be administered simultaneously or separate in time, and may be administered without interruption or separated by a length of time suitable for a given treatment regimen. Additionally, any administration routes known in the art may be used for the combined therapies, whether the same or different, any administration schedule suitable under the circumstances may be employed, and any number of therapies may be so combined.

Example 2

In CNS tumors, including medulloblastoma, the expression level of Survivin, as assayed by immunohistochemical analysis and RT-PCR, correlated negatively with overall survival. Patients whose tumors expressed high levels of Survivin had poor clinical outcomes. The survivin promoter was used to drive the expression of a cytolytic region coding for the active form of granzyme B, a protein involved in cytotoxic T-Lymphocytes (CTL) and Natural Killer (NK) cell activities. Using this approach, the cell growth of Daoy cells was significantly reduced, rivaling currently used chemotherapeutic drugs. The effects of this therapy included increased caspase activation and programmed cell death. The data validate the methods of the invention as a therapeutic modality with potential for the treatment of medulloblastoma.

A. Cell Lines and Transfections

Medulloblastoma cell lines, i.e., Daoy cells (ATCC HTB-186), were grown in DMEM-(Mediatech) supplemented with 10% FBS and grown at 37° C. in 95% air, 5% $CO_2$. For growth analysis, cells were seeded at a density of $1.5 \times 10^5$ cells. Transfections were performed using effectene transfection reagent, at a ratio of 1 µg DNA:10 µl effectene. Vincristine sulfate was used at a concentration of 2 µM.

B. Microscopic Analysis

Living cells in 12-well plates were observed by phase contrast microscopy using a Leica Inverted microscope at 10× magnification.

C. Mitochondrial Potential

To measure mitochondrial potential from the different experimental conditions, cells were loaded with 10 µg/ml JC1 for 15 minutes at 37° C. and 5% $CO_2$. The cells were washed with PBS twice, and diluted to 300 µl in PBS. Analysis was performed by FACS.

D. Annexin V

To analyze early apoptotic events, cells from the different experimental conditions were subjected to staining with an Annexin V-FLUOS kit (Roche). Analysis was performed by FACS, as above.

E. Cell Viability and Late Apoptosis/Necrosis

To determine cell viability, cells were subjected to trypan blue exclusion assays. Briefly, cells were washed with PBS, and diluted 1:1 in a solution of 0.4% trypan blue. Viable cells were counted and total viable cell number was used for growth curves. Late apoptotic/necrotic cells were also identified by staining with 0.4% trypan blue. The number of apoptotic/necrotic cells were counted and expressed as a percentage of the total number of cells.

F. Granzyme Activity (Caspase 3)

We assessed the function of Granzyme B by measuring Caspase-3 activation. Proliferating Daoy cells were transfected with SAGA for 24 or 48 hours, as previously described. Two thousand cells in 50 µl were diluted with Caspase 3/7 Glo reagent (Promega) at a 1:1 ratio. The reactions were incubated at room temperature for 30 minutes and measured for luminescence in a Victor3 plate reader (Perkin Elmer). Successful Caspase-3 activation was obtained in SAGA-transfected cells, as demonstrated by a large increase in relative luminescence from these cells compared to control transfected cells at both 24 and 48 hours.

G. Growth of SAGA-Transfected Cells is Impaired

Since SAGA-expressed Granzyme B was shown to be active, its effect on the growth of Daoy cells in culture was examined and the effect was compared to the commonly used chemotherapy drug, vincristine (VCR). Proliferating Daoy cells were seeded at a density of $1.5\times10^5$ cells and transfected with control plasmid, SAGA, or treated with 2 µM VCR. Viable cells were assayed by trypan blue exclusion at 0, 24, 48 and 72 hours post-transfection/treatment. There was a 90% decrease in the viability of SAGA-transfected cells at 24 hours compared to 50% for VCR-treated cells. Control cells grew consistently, with a doubling time of approximately 48 hours.

H. Morphological Changes

SAGA-transfected, VCR-treated, and control cells were visualized microscopically at 0, 24, 48 and 72 hours post transfection/treatment. At 0 hours, the cells in all groups appeared healthy. At 24 hours, there was massive apoptosis seen in SAGA-treated cells. At 48 and 72 hours, there were high numbers of apoptotic cells in both SAGA- and VCR-treated cells, with a very high degree of morphologically abnormal cells in the population of cells transfected with SAGA.

I. Apoptosis

Granzyme B is actively involved in NK- and CTL-mediated apoptosis, which led to a comparative investigation of the different stages of apoptosis in SAGA-transfected cells and VCR-treated cells.

1. Early Apoptosis

Annexin-V/PI is a commonly used method to detect early apoptotic events in cells. We employed this strategy to assay early apoptosis in SAGA transfected cells at 24 and 48 hours. The levels of early apoptosis in these cells were higher than in control and VCR-treated cells.

2. Mitochondrial Potential

Granzyme B has been implicated in mitochondrial-dependent apoptosis both in vitro and in vivo. It has been reported that as a result of Granzyme B activity, there is a decrease in mitochondrial potential to allow the release of factors like Cytochrome C and AIF into the cytoplasm/nucleus, which are important events in mitochondrial-dependent apoptosis. To assay mitochondrial potential, cells from the different experimental conditions were treated with the mitochondrial potential indicator dye JC1. The dye was incubated at 10 µg/ml in living cells at 37° C. for 15 minutes. After extensive washes, the cells were analyzed by FACS. A marked decrease in mitochondrial potential was observed in SAGA-transfected cells compared to control cells, as evidenced by the increase in intensity of green fluorescence and the decrease in intensity of red fluorescence, indicating the accumulation of the dye in the cytoplasm. Low mitochondrial potential is reflective of active apoptosis, and is associated with Granzyme B activity.

Example 3

The methods were assessed using in vitro assays to determine the potential of these methods as cancer therapies. The construct subjected to assay, described herein (SAGA), placed the survivin promoter in operable linkage to a modified form of the cytolytic gene granzyme B that included only the coding region for the active form of Granzyme B. In using the survivin promoter to drive the expression of active Granzyme B, the assay emulated, in part, the mode of action of CTL and NK cells.

A. Cell Lines and Transfections

Representative cell lines for cervical (HeLa cells; ATCC CCL-2), breast (MCF-7 cells; ATCC HTB-22), alveolar rhabdomyosarcoma (1:13, RH28 cells; kind gift of Dr. Stephen Qualman, Center for Childhood Cancer, Columbus Children's Hospital), embryonal rhabdomyosarcoma (RD2 cells; ATCC CCL-136), hepatocellular carcinoma, (HepG2 cells; ATCC HB-8065), and colon (SW620 cells; ATCC CCL-227) cancer cells were grown in DMEM (Mediatech) supplemented with 10% FBS at 37° C. in 95% air, 5% $CO_2$. A representative cell line for glioblastoma (LN18 cells; ATCC CCL-2610) was grown in RPMI-1640 (Mediatech) supplemented with 10% FBS at 37° C. in 95% air, 5% $CO_2$. For growth analysis, cells were seeded at variable densities from $1.5\times10^5$ to $2.5\times10^5$ cells. Transfections were performed using effectene transfection reagent, at a ratio of 1 µg DNA:10 µl effectene.

B. Microscopic Analysis

Living cells in 12-well plates were observed by phase contrast microscopy using a Leica Inverted microscope at 10× magnification.

C. Growth of SAGA-Transfected Cells is Impaired

Proliferating cells lines described in section A, above, were seeded at a density of $1.5\times10^5$ to $2.5\times10^5$ cells and transfected with control plasmid or SAGA. Viable cells were assayed by trypan blue exclusion at 0, 24, 48 and 72 hours post-transfection/treatment. At 72 hours post treatment, cervical cancer cells treated with SAGA corresponded to 9.8% of the original inoculum. By comparison, control cells had grown to 540% of the original inoculum. Breast tumor cell level was at 67.1% of the original inoculum, compared to the growth of control cells to 310% of the original inoculum. Alveolar rhabdomyosarcoma cells were at 39%, while control cells were at 220%, both relative to appropriate control cells. A more refractory model cell line for glioblastoma, LN18, showed a cell level of 225% for SAGA-treated cells and 426% for control treated cells, thus confirming a reduced growth rate for these cells, despite no significant reduction in cell number. Thus, the results established that SAGA-transfected cells exhibited impaired growth.

D. Combination Therapies

In addition to the isolated effects of SAGA expression on transfected cells, the combined effects of treatment with SAGA and chemotactic agents vincristine sulfate or paclitaxel (taxol) were evaluated in vitro using the cell lines listed in A. At 24, 48 and 72 hours, a decrease in viability of cells receiving the combined treatment was observed relative to either treatment alone, specifically in cell lines more refractory to SAGA treatment alone (HepG2, LN18 and SW620). These results suggest that combination therapies provide a more aggressive approach to containing cell growth. Although not wishing to be bound by theory, these results are perhaps due to enhanced Granzyme B activity in the combined therapy analyzed due to known increased activation levels of the survivin promoter in the G2/M phase of the cell cycle.

The in vitro studies demonstrated the efficacy of this system on model cell lines in a panel encompassing malignant tumors from virtually all types of tumors (see above). The method was effective in all cell lines tested, with glioblastoma (LN18), hepatocellular carcinoma (HepG2) and colon (SW620) responding to a smaller degree than the other tumor cell types; the only cells that did not respond to treatment at all were the non-tumorigenic mammary epithelial cells (see Example 4) used as controls. Efficiency could be correlated with the different levels of activation of Survivin, the varying levels of resistance to Granzyme B apoptosis, and the efficiency of SAGA delivery to the cells. Overall, the methods were highly efficient at containing cell growth and reducing cell number for a range of cells originating in different tumors. These results indicate that the methods of the invention are useful in treating a variety of different malignancies.

Example 4

Possible effects of the materials and methods according to the invention on normal cells were assessed using in vitro assays. The SAGA construct (see Example 1 and FIG. 1) subjected to assay effectively emulated, in part, the mode of action of CTL and NK cells. The data validate the materials and methods of the invention as therapeutic modalities with potential for the treatment of malignancies while sparing normal tissues.

A. Cell Lines and Transfections

Normal (non-malignant) mammary epithelial cell lines, i.e., MCF-10A cells (ATCC CRL-10317), were grown in MEGM (Mammary Epithelial Growth Medium, Serum-free) from Clonetics, supplemented with insulin (10 µg/ml), hEGF (0.02 µg/ml), hydrocortisone (0.5 µg/ml) and cholera toxin (0.1 µg/ml) at 37° C. in 95% air, 5% $CO_2$. For growth analysis, cells were seeded at a density of $1 \times 10^4$ cells in Linbro wells. Transfections were performed using effectene transfection reagent, at a ratio of 1 µg DNA:10 µl effectene.

B. Growth of Saga-Transfected Normal Cells is Unaffected

Since SAGA is not expected to be very active in normal cells, due to relative silencing of the survivin promoter, it was expected that SAGA transfection into normal mammary epithelial cells would not significantly affect the growth of those cells. Accordingly, growth curve analyses were performed using mammary epithelial cells with, or without, SAGA. Proliferating MCF-10A cells were seeded at a density of $1 \times 10^4$ cells and transfected with a control plasmid or SAGA. Viable cells were assayed by trypan blue exclusion at 0, 24, 48 and 72 hours post-transfection. Growth of SAGA-transfected cells did not deviate from that of control treated cells at any time point assayed. Doubling times for both control and SAGA-treated MCF-10A cells were approximately 48 hours.

Example 5

The methods were assessed using in vivo assays to determine the safety of these methods as cancer therapies on normal mice. The construct subjected to assay was the above-described SAGA construct. The data further validate the methods of the invention as a therapeutic modality with potential for the treatment of malignancies while sparing normal tissues.

A. Mice

Normal mice of FVB/N background were obtained from Taconic and used at the adult age of 5 months. Mice were kept in a AAALAC approved facility at Columbus Children's Research Institute under IACUC approval. Feed and water were provided ad libitum.

B. In Vivo SAGA Treatment

SAGA DNA was combined with in vivo jetPEI at an N/P ratio (ionic ratio between jetPEI cations and DNA anions) of 7, in a solution of 5% w/v glucose. The reactions were incubated for 15 minutes before injection. Controls consisted of the reporter gene lacZ (encoding β galactosidase) under the control of a survivin promoter or a CMV promoter. The CMV-lacZ construct was used as a positive control for injection because the CMV promoter was known to be active under the conditions used. The survivin-lacZ construct provided an opportunity to experimentally confirm the tissues in which the survivin promoter would be active. Twenty micrograms of conjugated DNA were injected into the tail vein of isoflurane anesthetized mice. Retro-orbital bleeds were performed on mice from all groups at 0, 24 and 48 hours. Serum was separated by centrifugation in serum separator tubes (Becton Dickinson) for 15 minutes at room temperature. Serum was assayed for β-galactosidase activity using a β-galactosidase enzyme assay system (Promega). β-galactosidase activities in sera from mice treated with SAGA or survivin-β-galactosidase were at background levels, whereas serum from mice treated with CMV-β-galactosidase had substantially increased levels of β-galactosidase activity.

C. Gross Analysis of SAGA-Treated Mice

At 48 hours post-treatment, SAGA-treated and control-treated mice were analyzed by a clinical veterinarian prior to sacrifice by $CO_2$ inhalation. Mice were necropsied and major organs (lung, heart, liver, kidneys, stomach, intestine, brain including pituitary gland, spleen, bladder and gonads) were grossly analyzed by a veterinarian. All organs of SAGA-treated mice appeared normal and healthy, including active digestion as demonstrated by the presence of food in the stomach compartments, and regular feces in the intestinal tract. The findings in SAGA-treated mice did not deviate from control-treated mice, establishing the safety of SAGA treatment is vivo.

D. Apoptotic Analysis of SAGA-Treated Mice

Thymus and spleen from SAGA- and control-treated mice were isolated at necropsy, following 48 hours of treatment. The organs were collected into cold RPMI-1640 supplemented with 10% FBS. Thymocytes and splenocytes were isolated following maceration of the tissue in medium. Isolated cells in suspension were subjected to Annexin V-FLUOS staining and analyzed by FACS. The levels of early apoptosis observed in SAGA-treated mice were less than 1% for splenocytes and 3% for thymocytes, consistent with the levels of apoptosis seen in cells of control-treated mice.

E. Efficient Delivery of SAGA into FVB Mice

DNA was isolated from thymocytes and splenocytes of SAGA-treated mice using a Puregene DNA purification system (Gentra). DNA quality and concentration were assayed by spectrophotometry. Detection of SAGA DNA was performed by PCR amplification using human primers specific for human granzyme B cDNA (SEQ ID NO:2), 1 µg of thymocyte or splenocyte DNA in a reaction with Amplitaq Gold with initial denaturation for 10 minutes at 95° C., followed by 35 cycles of 40 seconds at 94° C., 40 seconds at 55° C. and 40 seconds at 72° C. PCR products were resolved on 1.2% agarose gels. Specific amplification of human granzyme B cDNA was achieved in both thymocytes and splenocytes isolated from SAGA-treated mice, thus confirming that the DNA was delivered to the cells effectively and the in vivo delivery of SAGA to normal cells is relatively safe.

Example 6

SAGA effectively reduces tumor growth in an intraperitoneal xenograft model of a primary intraperitoneal ovarian tumor and it inhibits the development of metastatic disease in this model.

A. Plasmid Constructs

Active human Granzyme B cDNA was amplified from an EST obtained from a human T-cell library with specific oligonucleotide primers containing engineered palindromic sequences for NcoI and XbaI restriction sites. A Polymerase Chain Reaction was performed with Amplitaq Gold DNA polymerase (Perkin Elmer) for 35 cycles with denaturation at 94° C. for 40 seconds, annealing at 55° C. for 40 seconds, and extension at 72° C. for 50 seconds. The resulting PCR fragment was digested with NcoI and AbaI, resolved on a 1% agarose gel, and purified using a Qiagen Gel extraction kit.

The cDNA fragment was ligated to pDRIVE Survivin (Invivogen) digested with BspHI and NheI. The ligation mixture was used to transform *E. coli* DH5α competent cells and clones were selected on zeocin-containing agar plates. Potential clones were confirmed by automated sequencing. Endotoxin-free DNA from pDRIVE Survivin and SAGA were prepared using the Qiagen EndoFree Maxiprep kit for all further experiments. DNA quality and concentration were estimated by spectrophotometric analyses.

B. Cell Culture

MCF10-A, a non-transformed breast cell line (ATCC) was grown in MEGM, Mammary Epithelial Growth Medium, Serum-free, (Clonetics) supplemented with BPE, 2 ml; hEGF, 0.5 ml; Hydrocortisone, 0.5, 0.5 ml; GA-1000, 0.5 ml; Insulin, 0.5 ml and 100 ng/ml cholera toxin (Sigma Aldrich) at 37° C., 5% $CO_2$. HeLa (cervical adenocarcinoma), Daoy (medulloblastoma), MCF-7 and MDA-MB231 (breast adenocarcinoma), HepG2 (hepatocellular carcinoma), SW620 and Caco2 (colorectal carcinoma) cells (ATCC) were grown in DMEM supplemented with 10% FBS at 37° C., 5% $CO_2$; U2OS and Saos-2 osteosarcoma cells were grown in McCoy's 5A medium supplemented with 10% FBS at 37° C., 5% $CO_2$; Jurkat and 697Bcl2 (acute lymphoblastic leukemia), HL60 and KG1 (acute myeloblastic leukemia), SKOV-3, ES2 and OVCA429 (ovarian carcinoma), RH30 and RH28 (alveolar rhabdomyosarcoma), RD2 (embryonal rhabdomyosarcoma), LN18 (glioblastoma) and A549 (lung carcinoma) (ATCC) were grown in RPMI1640 supplemented with 10% FBS at 37° C., 5% $CO_2$.

C. Transfections

Transient transfections were performed using Effectene transfection reagent (Qiagen) at a DNA:Effectene ratio of 1:10, as described (26, 27), except for leukemia cells where the DNA:Effectene ratio was 1:25. Transfections were allowed to proceed for 24, 48 or 72 hours. Vincristine sulfate was used at a concentration of 2 μM, and paclitaxel was used at a concentration of 10 μM.

D. Cell Viability Determinations

To determine cell viability, trypan blue exclusion assays were performed. Briefly, cells were washed with phosphate-buffered saline (PBS), and diluted 1:1 (v/v) in a solution of 0.4% trypan blue (Sigma). Viable cells were counted in a hemocytometer, and total viable cell number was used for cell growth analyses. Experiments were performed in quintuple.

E. Annexin V Assays

To analyze early apoptotic events, cells from the different experimental conditions were subjected to staining with an Annexin V-FLUOS kit (Roche) as previously described (26, 27 and above). Experiments were performed in quintuple and analysis was performed by FACS.

F. Caspase-3 Assays

Two thousand cells from each experimental condition were assayed for caspase-3 activity using the Caspase-Glo 3/7 Assay (Promega), according to manufacturer's instructions. Caspase-3 activity was measured in a Victor-3 plate reader (Applied Biosystems) and expressed as relative luciferase units after background subtraction, as previously described (27). Experiments were performed in sextuple.

G. β-Galactosidase Assays

Tissues were removed from injected animals (liver, lung, thymus, spleen, kidney, and muscle) and protein was isolated with Cell Lysis Buffer (Promega). β-Galactosidase activity was assayed using the β-Galactosidase Assay system (Promega), according to manufacturer's instructions.

H. Animal Studies

Six- to eight-week-old female NOD/SCID mice were injected with $2.5 \times 10^6$ proliferating SKOV-3 cells (prepared in PBS at a density of $1.25 \times 10^7$ cells/ml) by intraperitoneal injection. Palpable intraperitoneal tumors developed within 3 weeks (21 days) in all mice injected (n=50), representing a 100% take rate. In one experiment, mice were randomly assigned to 2 treatment groups (n=10) consisting of control-treated (pDRIVE-Survivin, containing the lacZ gene under control of the Survivin promoter) or SAGA-treated mice. Treatment was administered intraperitoneally twice weekly and consisted of 0.5 mg/kg of DNA complexed to in vivo JetPEI (Qbiogene) at an N/P ratio of 10, for a total of 18 days. The injection area was massaged after removal of the needle to aid dispersal of the solution in the abdominal region. In another experiment, mice were randomly assigned to 3 treatment groups (n=5) consisting of paclitaxel control, SAGA or combination of SAGA and paclitaxel. SAGA treatment was administered as described above for a period of 26 days after tumor establishment. Paclitaxel was administered intraperitoneally (15 mg/kg in a total volume of 200 μl/injection) twice during the course of the treatment period (days 3 and 24). Survival time reflects the time required for the animals to reach any of the experimental endpoints, including tumor ulceration, weight loss exceeding 15% of body weight, weight gain exceeding 5 g, anorexia, diarrhea and difficulties ambulating and/or feeding. The studies were performed under approval of the Columbus Children's Research Institute Animal Care Committee.

H. Biometric Analysis

Mice were weighed weekly after injection of tumor cells using a digital scale. Upon completion of the treatment period, mice were euthanized by carbon dioxide inhalation. A necropsy was performed in which the primary tumor, omentum, bladder, endometrium, ovaries, pancreas, spleen and kidneys were dissected, measured and weighed. The abdominal region was scored for metastatic foci by gross examination.

I. Histologic Examination

Tissues isolated after dissection were fixed in 10% neutral-buffered formalin for 16 hours at 4° C. and processed for paraffin embedding. Sections were taken at 5 μm thickness in a Leica microtome. Tumors were characterized by staining with hematoxylin and eosin, and immunohistochemistry for vimentin, pan-keratin, LCA (Leukocyte common antigen), and EMA (epithelial membrane antigen) using a Ventana automated stainer. PAS staining (periodic acid-Schiff's) for cytoplasmic glycogen content was performed according to standard protocols to confirm clear cell adenocarcinoma diagnoses. Tissue sections pre-treated with 1% diastase for one hour served as a negative control (PAS-D). To characterize response to therapy histologically, immunohistochemical staining with antibodies for Ki-67, human Granzyme B and Survivin (28) were performed. In situ terminal deoxynucleotidyl transferase labeling (a TUNEL assay) was performed with the TdT-FragEL DNA Fragmentation detection kit (Calbiochem), according to manufacturer's instructions. Collagen-Masson's trichrome staining was performed according to a standard protocol. Quantification of staining was performed on multiple high-powered fields (10 to 20) representative of the tissue and confirmed by a certified pathologist.

J. Microscopy

Living cells in 12-well plates were photographed using phase-contrast with a Leica inverted microscope at a 100× magnification. Tissue sections were photographed using phase-contrast with a Leica upright microscope at magnifications from 50-400×. Quantification of staining was performed on 10-20 high-powered fields.

K. Biostatistical Analysis

The growth of cells in vitro was modeled with a polynomial curve (cubic) and the rates of growth were compared with a Wilcoxon rank sums test. Differences in tumor weight, size and number of tumor nodules were analyzed with a two-sample t-test with equal variance, and two-sided significance. Differences in the incidence of metastasis and palpable tumors after treatment were analyzed by a two-way Fisher's exact and Chi square tests. Kaplan-Meier curves were obtained using the start of treatment as day 1. A log-rank test for equality of survivor functions was used. To analyze differences between mitotic cells, proliferation, and cell death, a simple linear regression model was fitted using animal identification as a cluster variable. To evaluate the differences in the levels of Survivin expression a non-parametric, two-sample Wilcoxon rank sum (Mann-Whitney) test was used. An ANOVA with repeated measurements was used to analyze body weight changes. In all cases, a $p \leq 0.05$ was considered significant. All statistical tests were two sided, performed and analyzed with STATA statistical software.

Example 7

The materials and methods described herein, and particularly those described in Example 6, were used to determine the specificity of exemplary recombinant nucleic acid molecules according to the invention for inducing apoptotic death in a wide range of cancer cells, without inducing significant apoptotic death in healthy or normal cells.

Figure 5:
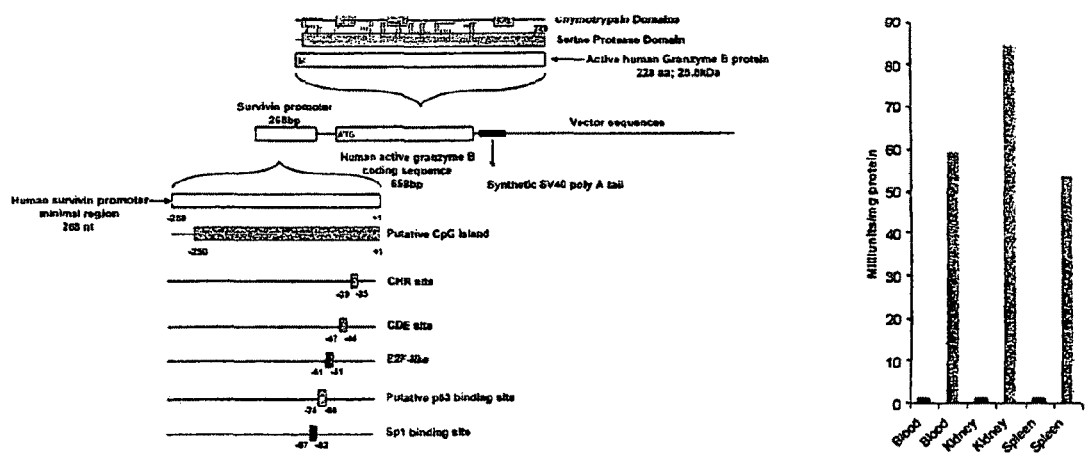
FIG. 5 shows that SAGA specifically inhibits tumor growth of multiple tumor cell lines. A) Schematic representation of the SAGA hybrid vector. SAGA is composed of a 268 bp region of the Survinin promoter (containing a putative CpG island, CDE/CHR sites, E2F-like, p53 and Sp1 binding sites) fused to the region coding for the active form of Granzyme B. The 3' end of the coding sequence is followed by a synthetic SV40 poly-A tail. B) Malignant transformed cell lines (RH28, 697Bcl2, MCF7, HeLa, Jurkat, LN18 and Daoy) and a non-transformed breast epithelial cell line (MCF10A) were transfected with 0.5 μg control (-●-) or SAGA (--○--) or combination SAGA and chemotherapy (---□---) using Effectene transfection reagent and cell growth was followed for 48 hours. C) FVB mice were injected with pDRIVE Survivin (black bars) or CMV-β galactosidase (grey bars) via the lateral tail vein. The mice were euthanized after 48 hours and protein lysates prepared from collected tissues. β galactosidase activity was quantified using the β galactosidase assay kit, and expressed as milliunits of β galactosidase per mg of protein.
Figure 5:
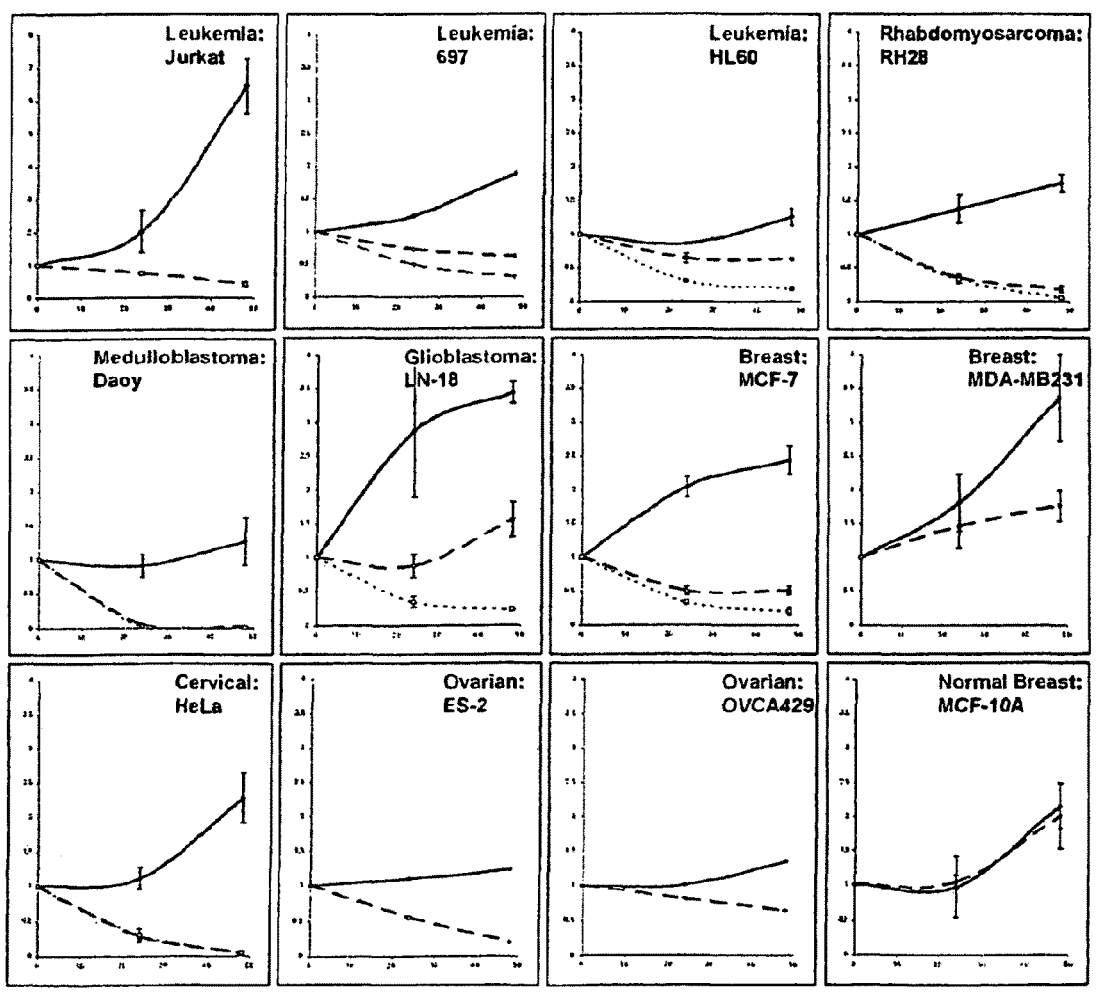

Taking advantage of the tumor-specificity of the Survivin promoter (23, 24), that promoter was used as an exemplar of the expression control-element(s) used to drive the expression of an apoptosis-inducing coding region, such as the coding region for mature Granzyme B, in a genetic approach to cancer therapy. The exemplary Psurvivin-Granzyme B hybrid construct consisted of a fusion of 268 bp of the human Survivin promoter, with the coding sequence of the active form of human Granzyme B (FIG. 5A). The modified Granzyme B coding region used in the construct eliminated the need for activation of the gene product by proteolytic cleavage, as an artificial start codon was fused to the active form of the enzyme that lacks the first 20 amino acids of the zymogen. Thus, the construct encoded an active form of Granzyme B, containing the serine protease and chymotrypsin domains essential for its protease activity. Included within the 268 bp of the Survivin promoter were critical sequences responsible for Survivin's natural transcriptional regulation, such as the CDE/CHR sites and E2F-like, TP53 and Sp1 binding sites (29-32). DNA was transfected into target cells as described in Example 6, and Granzyme B was expressed through activation of the Survivin promoter. This design resulted in the expression of active Granzyme B that was perforin-independent. The complete construct was designated SAGA, for Survivin and Granzyme B Apoptosis.

To evaluate the cell growth inhibitory effects of SAGA in vitro, multiple transformed cell lines were assessed. These lines included leukemias (T-ALL, B-ALL, and AML), CNS tumors (medulloblastoma, glioblastoma), soft tissue sarcomas, osteosarcomas (containing wild-type or mutated TP53), hepatocellular carcinoma, colorectal tumors, lung, breast, cervical and ovarian carcinomas. SAGA efficiently inhibited cell growth in all tumor cell lines tested (FIG. 5B), as demonstrated by the reduced growth of treated cells over a 48-hour period compared to control-transfected cells of the same type. A decrease in the total number of cells compared to baseline in the majority of cell lines tested was indicative of an increase in tumor cell death (FIG. 5B). When used in combination with the chemotherapeutic agents vincristine or taxol in leukemia, medulloblastoma, glioblastoma, rhabdomyosarcoma, breast and cervical carcinoma cells, a synergistic effect on cell death and growth inhibition was observed. This synergy was particularly evident in leukemia, glioblastoma and breast carcinoma (FIG. 1B, dashed line with open squares) cells. Although variable responses to treatment with SAGA were observed to correlate with the efficiency of DNA delivery observed for the different cell lines (Table 3 and FIG. 5B), a beneficial response was obtained with all cancer cells tested. Glioblastoma and the breast carcinoma cell line MDA-MB231 had the lowest transfection efficiency (10-15%) and their growth was less affected, whereas HeLa and Daoy cells had the highest transfection efficiencies (80-90%) and consequently a greater impairment of cell growth was observed. In some instances, the percentage of cell death observed was greater than the percentage of transfected cells. Without wishing to be bound by theory, this result may be attributable to a bystander effect that occurring due to the high rates of cell death accompanied by the loss of a large number of neighboring cells, as well as the release of apoptosis stimulating factors.

TABLE 3

| Cell Line | Transfection Efficiency |
| --- | --- |
| Jurkat | 35-40% |
| 697 | 30-40% |
| HL60 | 30-35% |
| RH28 | 65-75% |
| Daoy | 80-90% |
| LN18 | 15-20% |
| MCF7 | 45-50% |
| MDA-MB231 | 10-15% |
| HeLa | 80-90% |
| ES2 | 60-75% |
| OVCA429 | 50-60% |
| SKOV-3 | 75-85% |

To demonstrate the tumor specificity of recombinant molecules according to the invention, e.g., SAGA, a non-transformed human breast epithelial cell line, MCF10-A (33, 34), was transfected with the SAGA plasmid. Both control- and SAGA-transfected cells grew with an approximate doubling time of 48 hours (FIG. 5B), indicating that SAGA did not inhibit cell growth or induce programmed cell death in this non-malignant cell line. As it had been previously demonstrated that human and murine Survivin promoters contained conserved elements such that the human Survivin promoter can be activated in mouse tumor cells (35), non-tumor bearing mice were injected with DNA plasmids encoding the β-galactosidase gene under the control of a CMV promoter or the human Survivin promoter. β-galactosidase activities in tissue lysates collected from the injected mice were analyzed using the β-galactosidase enzyme assay system. The Survivin promoter was relatively silent in all murine tissues analyzed (FIG. 5C), indicating that even if Survivin was expressed at low levels in normal mouse tissues, these levels were not sufficient to be significantly cytotoxic in the presence of SAGA. These two types of experiments support the tumor-specificity of the recombinant nucleic acids of the invention, such as the SAGA construct. Further, the SAGA construct did not detectably affect the non-malignant MCF10A cell line in a deleterious manner, indicating that the materials and methods of the invention, e.g., SAGA constructs and methods for their use, will not result in a significant adverse effect on surrounding healthy mammary tissue in a breast tumor undergoing treatment according to the invention. It is expected that the materials of the invention will be relative safe in the presence of healthy tissue, regardless of the particular type of tissue.

Example 8

Figure 6:
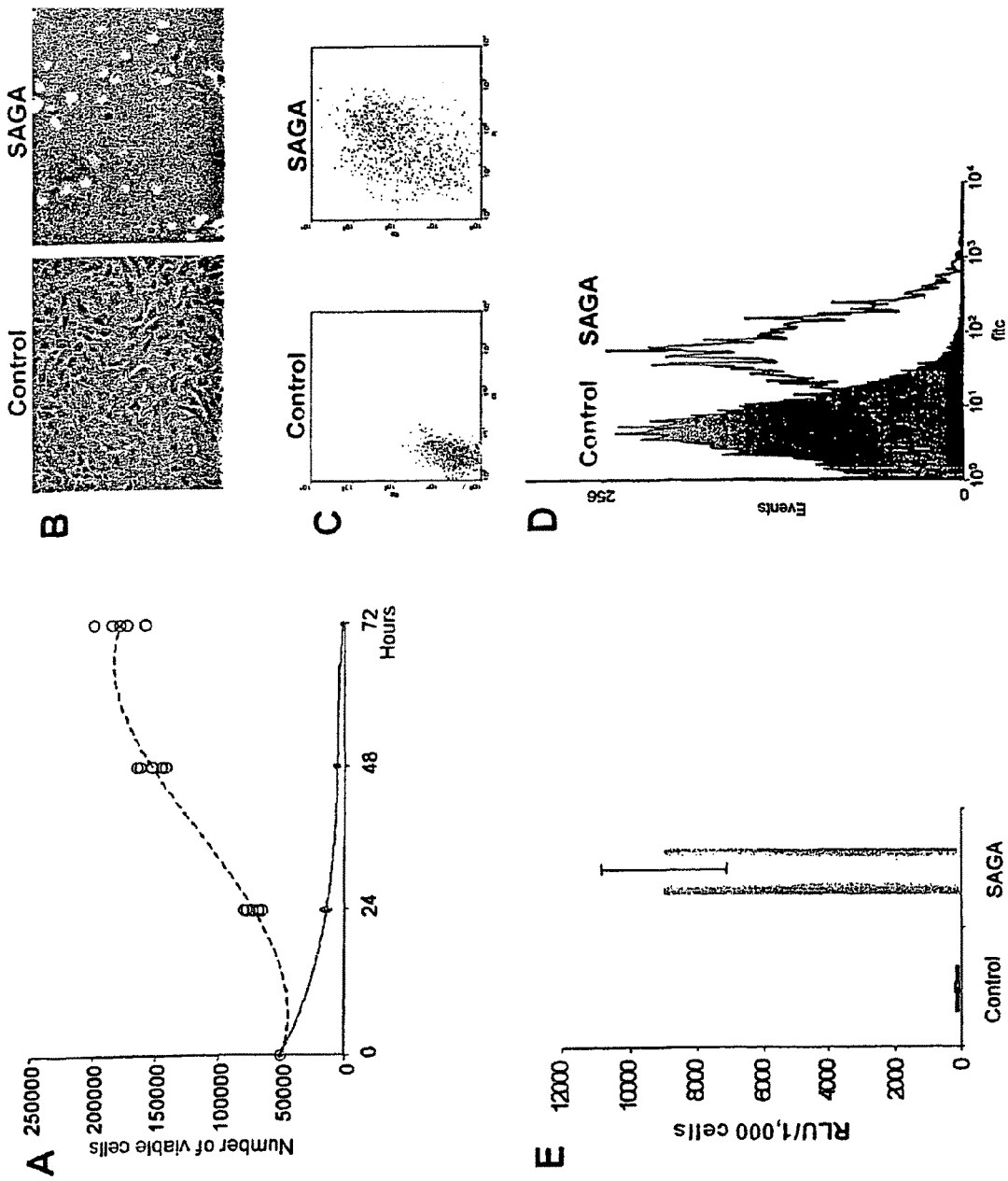
FIG. 6 provides data showing that SAGA inhibits tumor growth and induces apoptosis in ovarian carcinoma cells. SKOV-3 cells were transfected with SAGA or pDRIVE-Survivin DNA as described in the Examples. A) Growth of control (--○--) and SAGA (-●-) treated cells was followed for 72 hours. B) Phase contrast microscopy revealed the pro-apoptotic effects of SAGA in treated cells (100× magnification). C) and D) Control- and SAGA-treated cells were stained with Annexin-V-FITC and analyzed by flow cytometry. Double parameter (FITC/PI) analysis demonstrated an increased incidence of apoptosis in SAGA-treated cells (C), and single parameter analysis (FITC) demonstrated a higher number of cells staining positive for Annexin V in the SAGA-treated group (open area) relative to the control treated group (shaded area) (D). E) One thousand cells from each experimental condition were subjected to Caspase 3/7-GLO assay to determine the levels of activation of Caspase-3. SAGA-treated cells show elevations in Caspase-3 activity, in contrast with near background activation of control-treated cells.

The effect of a recombinant nucleic acid according to the invention, the SAGA construct, on ovarian cancer cells was assessed both in vitro and in vivo. The SKOV-3 cell line was used to characterize the in vitro and in vivo effects of SAGA on an ovarian cancer xenograft model. SKOV-3 is an epithelial ovarian adenocarcinoma cell line, originally isolated from the ascitic fluid of a patient with metastatic ovarian cancer. SKOV-3 cells are known to be highly resistant to cell death induced by any of several cytotoxic drugs (36). SKOV-3 cells also express Her2/neu at high levels, a finding clinically synonymous with poor prognosis (4, 37). SKOV-3 cells were transfected with SAGA or pDRIVE-Survivin as described in Example 6 and the growth of the cells was assessed over a period of 72 hours. The growth was modeled with a polynomial curve (cubic) and the rates of growth in control- and SAGA-treated cells were compared at 24, 48 and 72 hours with a Wilcoxon rank sums test (FIG. 6A). All points were significantly different between groups (p=0.0008), demonstrating that SAGA had a strong growth inhibitory effect on SKOV-3 cell in vitro. Growth impairment as well as a high rate of cell death were also clearly visible microscopically (FIG. 6B).

The molecular effects of SAGA on apoptosis were assessed using two different assays, Annexin V staining and Caspase-3 activation. Annexin V is a calcium-dependent phospholipid-binding protein with high affinity for phosphatidylserine (PS) (38). This protein is a sensitive probe for PS exposure to the outer leaflet of the cell membrane and, therefore, effectively detects early apoptotic events (38). A mean Annexin V staining in 36.7% of SAGA treated cells compared to less than 1% staining in control cells at 48 hours post-transfection (FIG. 6C, 6D). Caspase-3, a direct cleavage target of Granzyme B, was also used to assess SAGA's role in apoptosis. Caspase-3 activation was observed in SAGA-treated cells at levels 77 times higher than in control cells at 48 hours post-transfection (FIG. 6E). The rates of cell death were statistically different between groups for both Annexin V staining and Caspase-3 activation.

Figure 7:
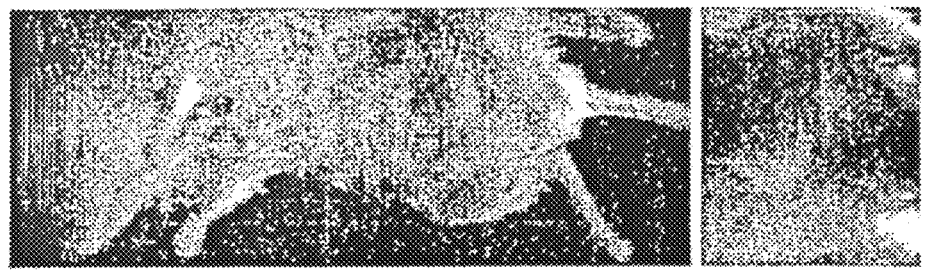
FIG. 7 shows SKOV-3 cells, which provide an intraperitoneal mouse xenograft model, that were injected into the intraperitoneal cavity of female NOD/SCID (non-obese diabetic/severe combined immunodeficiency) mice as described herein. A) All mice developed tumors by 3 weeks post injection, visualized as protrusions through the abdominal wall. B) Tumors isolated from the mice were characterized histologically by hematoxylin and eosin staining, vimentin, EMA and keratin immunohistochemistry, and by analysis of cytoplasmic glycogen content (PAS and PAS-D control).
Figure 7:
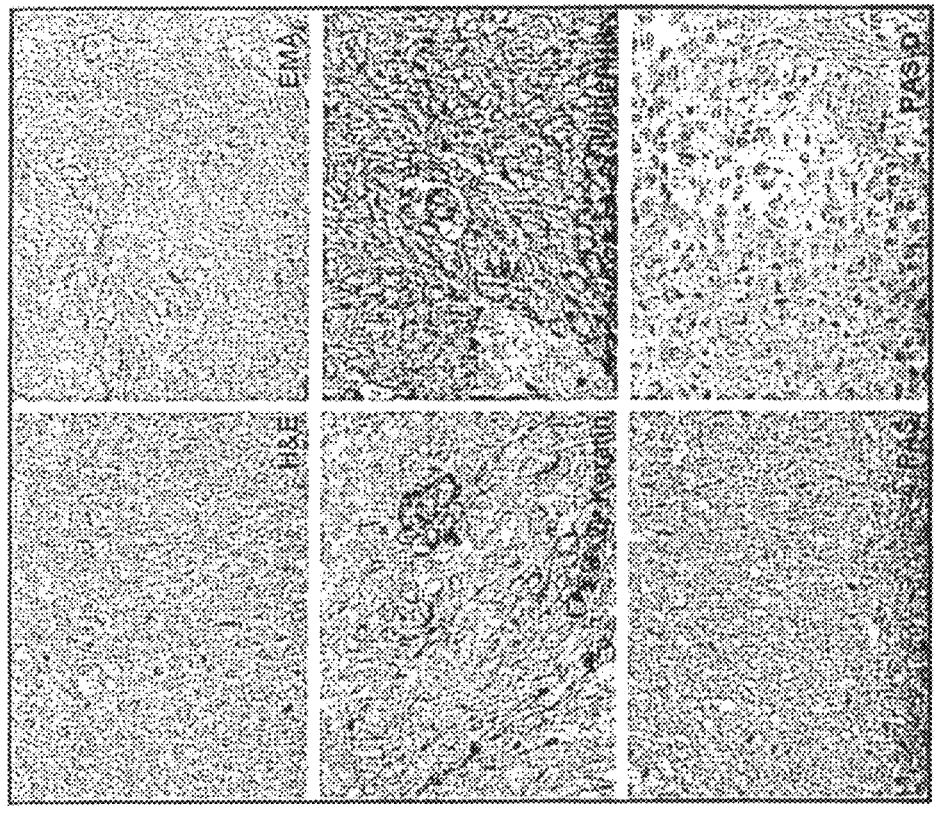

To characterize the clinical and histologic features of a human ovarian carcinoma xenograft model in vivo, $2.5 \times 10^6$ SKOV-3 cells were injected into NOD/SCID mice intraperitoneally. All mice developed palpable tumors within 3 weeks. Tumors became visible as a protrusion through the abdominal wall as early as 4 weeks after injection (FIG. 7A). At necropsy, multiple tumor nodules were frequently observed surrounding the primary tumor. Metastatic foci were also observed in other abdominal regions (9/10 animals). The larger primary tumors were adherent to the fat in the pelvic region and/or in the peritoneum. Metastatic nodules were found in these regions, in the omentum, mesentery and throughout the abdomen. Histologically, the tumors expressed the mesenchymal cytoskeletal protein vimentin and the epithelial markers EMA (epithelial membrane antigen) and keratin (FIG. 7B). High cytoplasmic glycogen content was also detected by PAS staining in the majority of tumor cells (FIG. 8B), a characteristic finding in human clear cell adenocarcinomas.

In addition, the SAGA construct described herein was hydrodynamically injected into the tail vein of immunocompetent mice (FVB). The presence of the plasmid was confirmed in a range of different tissues by PCR. SAGA-treated mice were healthy with no weight loss, no signs of anemia or alopecia, and no increased apoptosis observed in select tissues including thymus, spleen and bone marrow. Additionally, SAGA-treated mice had no behavioral changes and fed ad libitum, in a manner indistinguishable from the behavior exhibited prior to injection, with no detectable diarrhea. No adverse symptoms were detected during the study period of 60 days.

Figure 8:
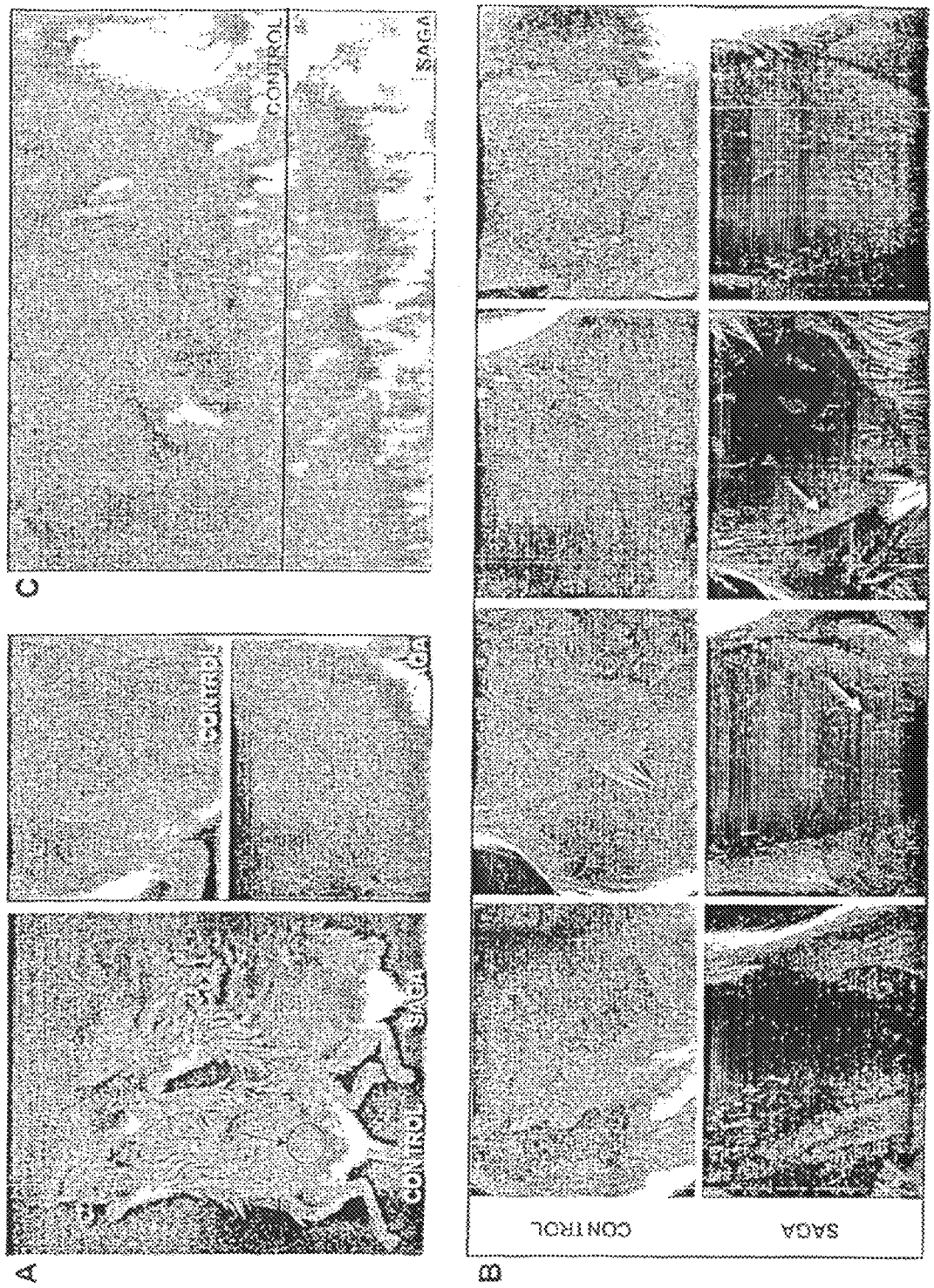
FIG. 8 provides data showing the effects of SAGA therapy on tumor size ini vivo. Female NOD/SCID mice bearing intraperitoneal ovarian tumors were randomized into 2 treatment groups (n=10), and treated for 18 days as described in the Examples. A) At the end of the therapeutic period tumors were clearly visible in control-treated animals but not in SAGA-treated animals. B) Upon necropsy, small tumor nodes could be detected at the site of injection of some SAGA-treated animals. C) Tumors isolated from control- and SAGA-treated animals were compared, revealing differences in tumor size due to the treatment (representative range of tumors shown).

To evaluate the efficacy of SAGA in the treatment of ovarian carcinoma, six- to eight-week-old female NOD/SCID mice were injected intraperitoneally with $2.5 \times 10^6$ SKOV-3 cells (n=20). Mice were weighed weekly and palpated for tumor engraftment. By 3 weeks, all mice had palpable tumors and were randomly assigned to one of 2 treatment groups, control or SAGA-treated (n=10). SAGA-treated mice received intraperitoneal injections of 0.5 mg/kg of SAGA DNA coupled to linearized PEI twice weekly for a total of 18 days, whereas control mice received a similar injection of control DNA (pDRIVE-Survivin) coupled to linearized PEI, on the same schedule. The size of treated tumors was dramatically reduced in SAGA-treated animals as noted by physical examination of the animals as early as one week after administration of the first course of treatment. Only 2 of 10 animals had palpable tumors at the end of the experimental period, compared to 10 of 10 control animals (p=0.001). Tumors from control animals were also visible externally at the end of the treatment period (FIG. 8A). At necropsy, the primary tumors were easily detected in all control-treated animals (FIG. 8B). The mean number of primary tumor nodules isolated in each control-treated animal was 9, compared to only 1.2 in SAGA-treated animals (Table 4). The difference in the number of tumor nodules between the two groups was statistically significant (7.8, 95% CI: 4.6-11.0, p=0.0001). Only 8 of 10 animals treated with SAGA had visible tumors at necropsy, indicating that 2 animals had achieved a complete clinical remission. Of the remaining 8 animals with tumors, 2 animals had tumors less than 1 mm in diameter. The overall mean diameter of SAGA-treated tumors was 2.8 mm, compared with a mean diameter of 11.4 mm for control tumors (FIG. 8C). The difference in tumor size between groups was highly significant (8.5 mm, 95% CI: 6.3-10.7 mm, p<0.001). Consistent with the findings of a dramatic reduction of tumor size, the mean tumor weight for SAGA-treated animals was 22 mg compared with a mean tumor weight of 146 mg in control-treated tumors. This represents a 6.5-fold difference in tumor weight that was also highly significant (123 mg, 95% CI: 83-164 mg, p<0.001).

TABLE 4

| Treatment | Animals with Tumors at Completion of Therapy | Disease Dissemination | Ovarian Metastases | Survival at Endpoint | Tumor Weight (mg) | Tumor Size (mm) | Number of Nodules |
|---|---|---|---|---|---|---|---|
| Control | 10 of 10 | 9 of 10 | 3 of 10 | 3 of 10 | 146.0 ± 56.4 | 11.4 ± 2.2 | 9.0 ± 4.7 |
| SAGA | 8 of 10 | 0 of 10 | 0 of 10 | 9 of 10 | 22.0 ± 22.4 | 2.8 ± 2.4 | 1.2 ± 0.8 |

Figure 9:
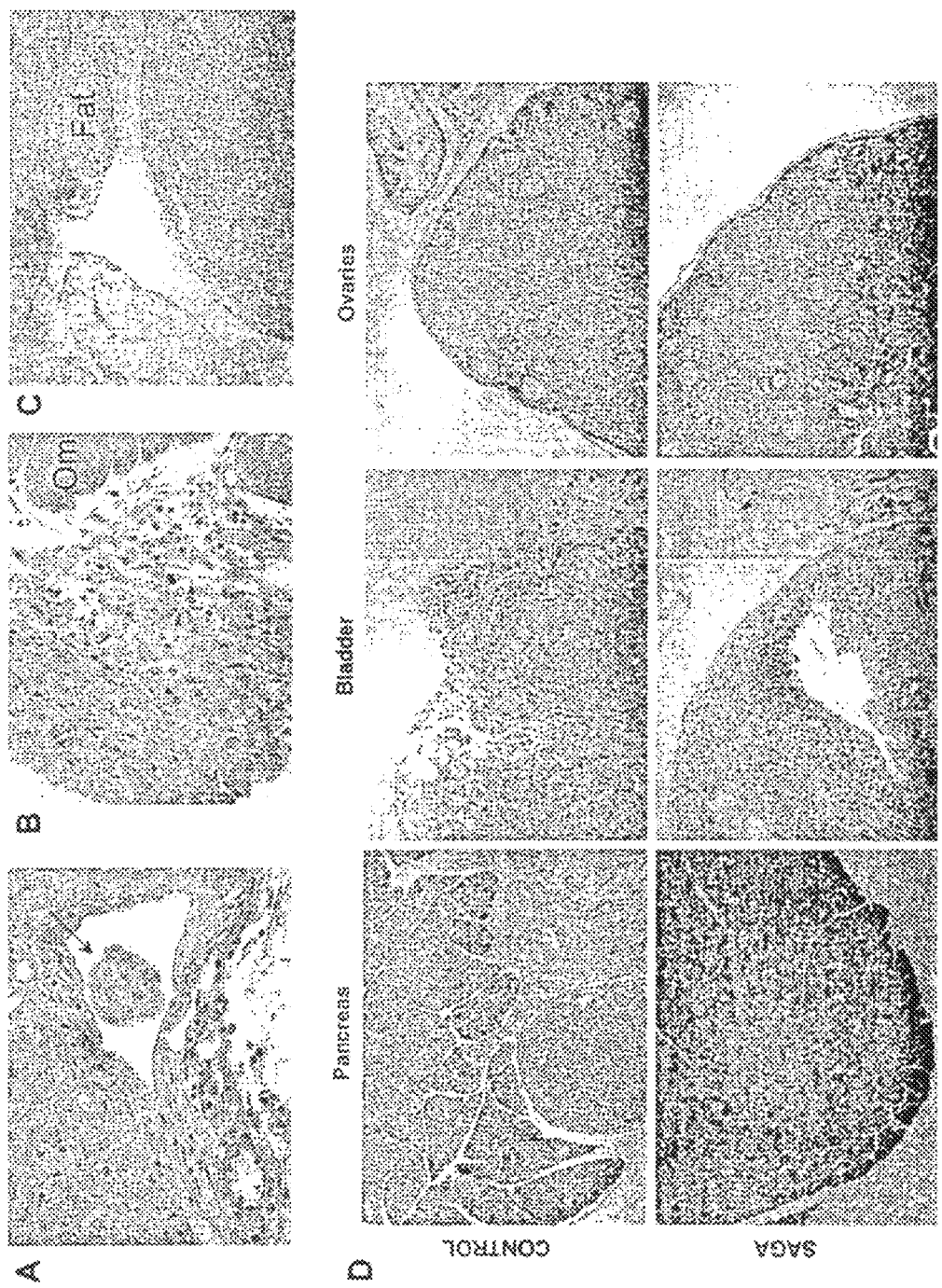
FIG. 9 shows the effects of SAGA on disease dissemination. Control and SAGA-treated animals were analyzed for evidence of metastatic dissemination following the completion of therapy, by necropsy. A) Tumor cell infiltration of lymphatic, B) engraftment of tumors cells onto the omentum and C) tumors nodules attached to the fat surrounding abdominal organs were exclusively found in control-treated animals. D) Additional regions of dissemination in control-treated animals included the pancreas, bladder and ovaries, which were not observed in any of the SAGA-treated animals.

The exemplary recombinant nucleic acid according to the invention, SAGA, also had a beneficial effect on the metastasis of ovarian carcinoma cells in vivo. Metastatic nodules, presenting as tumor masses distant from the site of injection, were observed in 9 of 10 control-treated animals. In contrast, 0 of 10 SAGA-treated animals developed metastases ($p<0.001$). Metastatic nodules in control-treated tumors were found within the abdominal cavity distinct from, but within the vicinity of, the primary tumor, as well as in other regions, including the mesentery, lesser omentum, attached to the fat (FIG. 9A), surrounding the pancreas, spleen and endometrium, or within the bladder and the ovaries (FIG. 9B). Metastatic foci within the ovaries themselves were detected in 3 of 10 control-treated animals. These foci presented unilaterally as 1 or 2 small nodules within the stromal region of the ovary. Invasion of the lymphatic system, a known mechanism of metastatic spread in human ovarian tumors, was clearly visible in control treated tumors (FIG. 9A, arrow).

Figure 10:
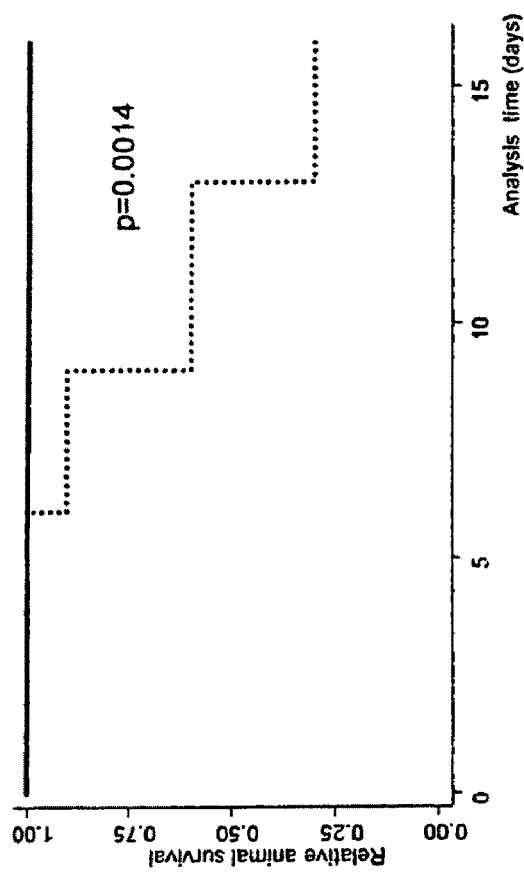
FIG. 10 provides a Kaplan-Meier analysis of SAGA-treated tumors. Kaplan-Meier survival analysis shows a significant increase in survival of SAGA-treated animals (solid line) compared to that of control-treated animals, (dashed line).

Survival within the two treatment groups, as defined by the time required for the animals to reach any of the pre-established experimental endpoints throughout the treatment period, was calculated by Kaplan-Meier analysis. The median survival time for control-treated animals was 13 days from the start of treatment ($25^{th}$ percentile=9 days), whereas 100% of SAGA-treated animals survived the entire length of the follow-up period (18 days). At the end of the experimental period there were 10 survivors in the SAGA-treated group (100%), compared to only 3 in the control-treated group (30%). The survival difference between control and SAGA-treated animals was significantly different by log rank test, $p=0.0014$ (FIG. 10).

Figure 12:
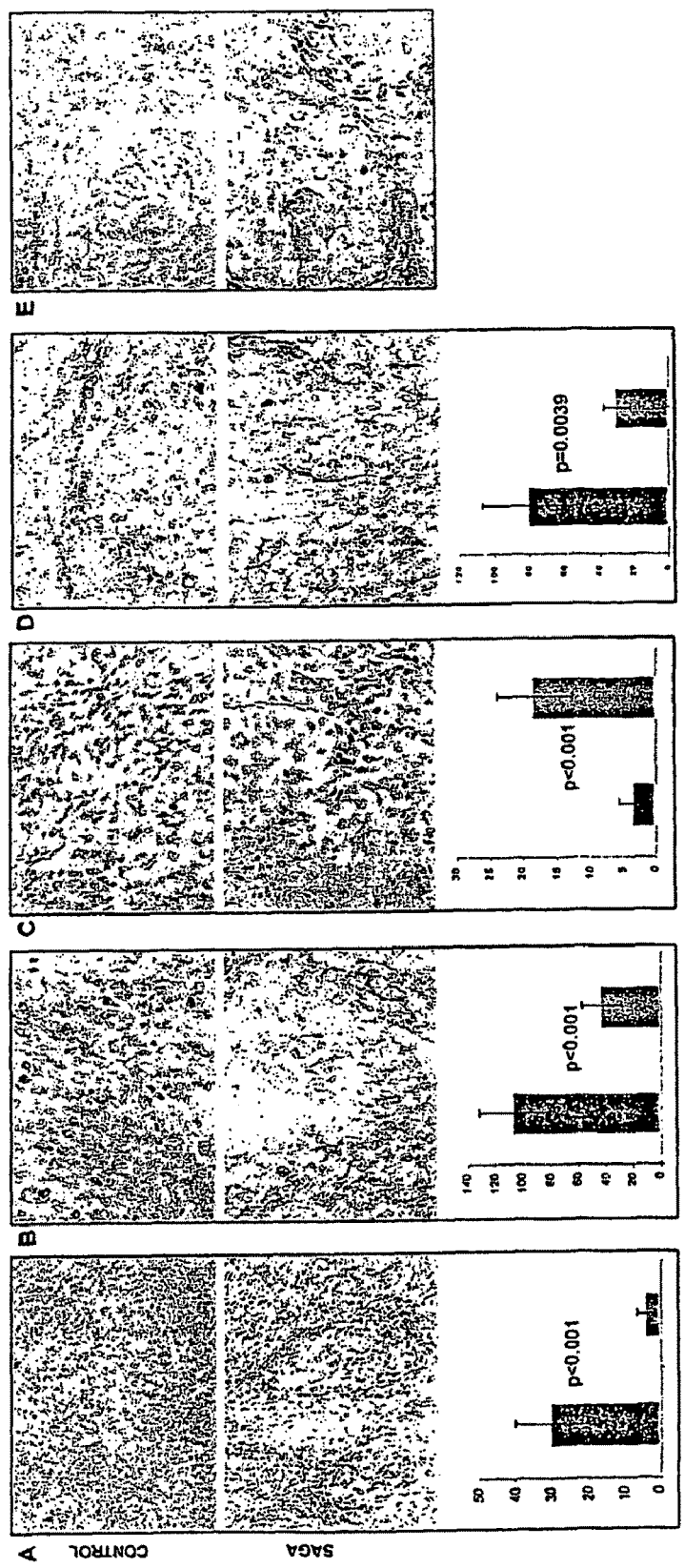
FIG. 12 shows the molecular effects of SAGA treatment in vivo. Tumors isolated from control- and SAGA-treated animals were fixed, processed and paraffin-embedded. Sections were collected at 5 µm thickness and A) stained with hematoxylin and eosin to assess the number of mitotic cells and degree of anaplasia; B) immunostained with Ki-67 to determine the proliferative index; C) labeled with TdT in situ to determine the levels of apoptosis; D) stained with a polyclonal anti-Survivin antibody to demonstrate the specific targeting of Survivin-expressing cells; E) stained with a polycional antibody to human Granzyme B to demonstrate the expression of Granzyme B in SAGA-treated tumors. The graphs represent the quantification of staining in an area measuring 0.1 mm$^2$ (red=control, green=SAGA).

Evaluation of the expression of the proliferation marker Ki-67 and the cell death marker TUNEL were performed to determine the effects of SAGA treatment on inhibiting cell growth and inducing programmed cell death in the ovarian tumors in vivo. SAGA-treated tumors had a lower number of mitotic figures than control-treated tumors ($p<0.001$, $R^2=0.78$) (FIG. 12A). Although viable tumor cells were observed in SAGA-treated animals at the completion of therapy, a 60% decrease in the number of proliferating cells was observed by Ki-67 staining ($p<0.001$, $R^2=0.72$) (FIG. 12B). This reduction in proliferating cells was accompanied by an increased incidence of programmed cell death, as assessed by TUNEL assay (5.6-fold increase compared to control-treated tumors, $p<0.001$, $R^2=0.77$) (FIG. 12C).

Figure 13:
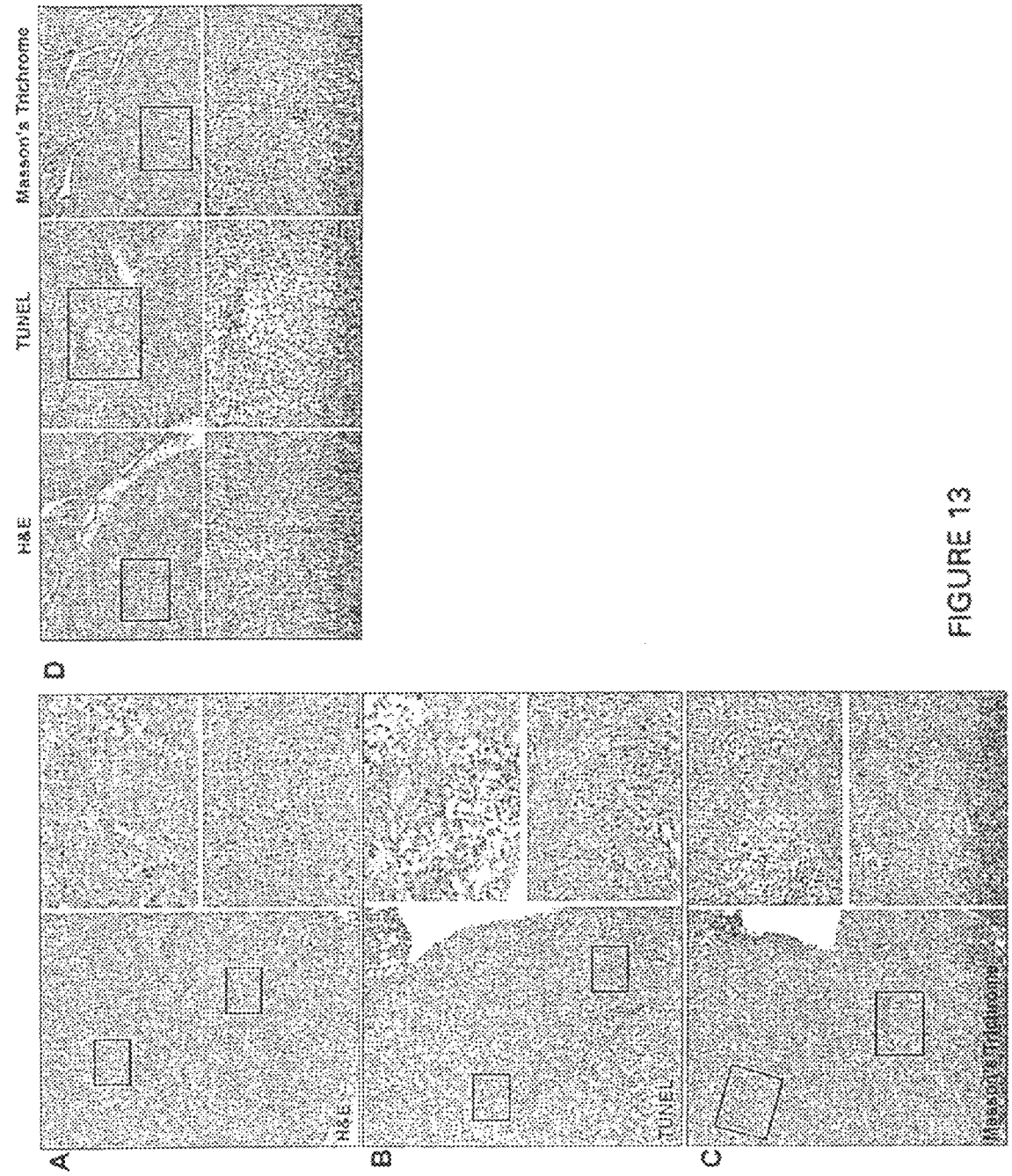
FIG. 13 shows the effect of SAGA-therapy on programmed cell death within tumors. A) SAGA-treated tumors often contained large areas of karyopyknosis and karyorrhexis observable by hematoxylin and eosin staining. B) and C) These areas stained strongly positive by TUNEL and were associated with reactive fibrosis, evidenced by Masson's trichrome staining. D) Similar regions in the control-treated tumors were negative for TUNEL and trichrome.

To molecularly link the mechanism of SAGA-induced cell death to Survivin and Granzyme B, the levels of Survivin and of Granzyme B in the treated tumors was determined. The incidence of Survivin-expressing cells was decreased by 60% in SAGA-treated tumors ($p=0.0039$), demonstrating the specific targeting and elimination of Survivin-expressing tumor cells by SAGA (FIG. 12E). Granzyme B was also observed in the predicted cytoplasmic pattern in tumors treated with SAGA, but not in any control-treated tumors (FIG. 12D). SAGA-treated tumors displayed areas of karyopyknosis, and karyorrhexis by histology, corresponding to apoptotic cells as identified by in situ TdT labeling (TUNEL). These large patches of TUNEL-positive cells were associated with reactive fibrosis, which enveloped the involved regions of the tumor in a thick layer of fibroblastic tissue, as visualized by Masson's trichrome staining (FIG. 13). By contrast, large control-treated tumors lacked the organized regions of fibrosis observed in SAGA-treated tumors.

Example 9

The potential for the therapeutic recombinant nucleic acids to be used in combination therapies to treat disease was assessed. A suitable disease, cancer, was investigated using combination therapies in which the recombinant nucleic acids, e.g., SAGA, were combined with any of a number of known anti-cancer agents. The known anti-cancer agents investigated were chemotherapeutic agents, although it is expected that the recombinant nucleic acids will function in combination therapies for cancer using any known anti-cancer agent, such as radiation therapy. Moreover, it is expected that the recombinant nucleic acids will function in combination therapies with known therapeutic agents for treating any disease, disorder or condition for which the recombinant nucleic acid alone has a therapeutic effect.

Figure 11:
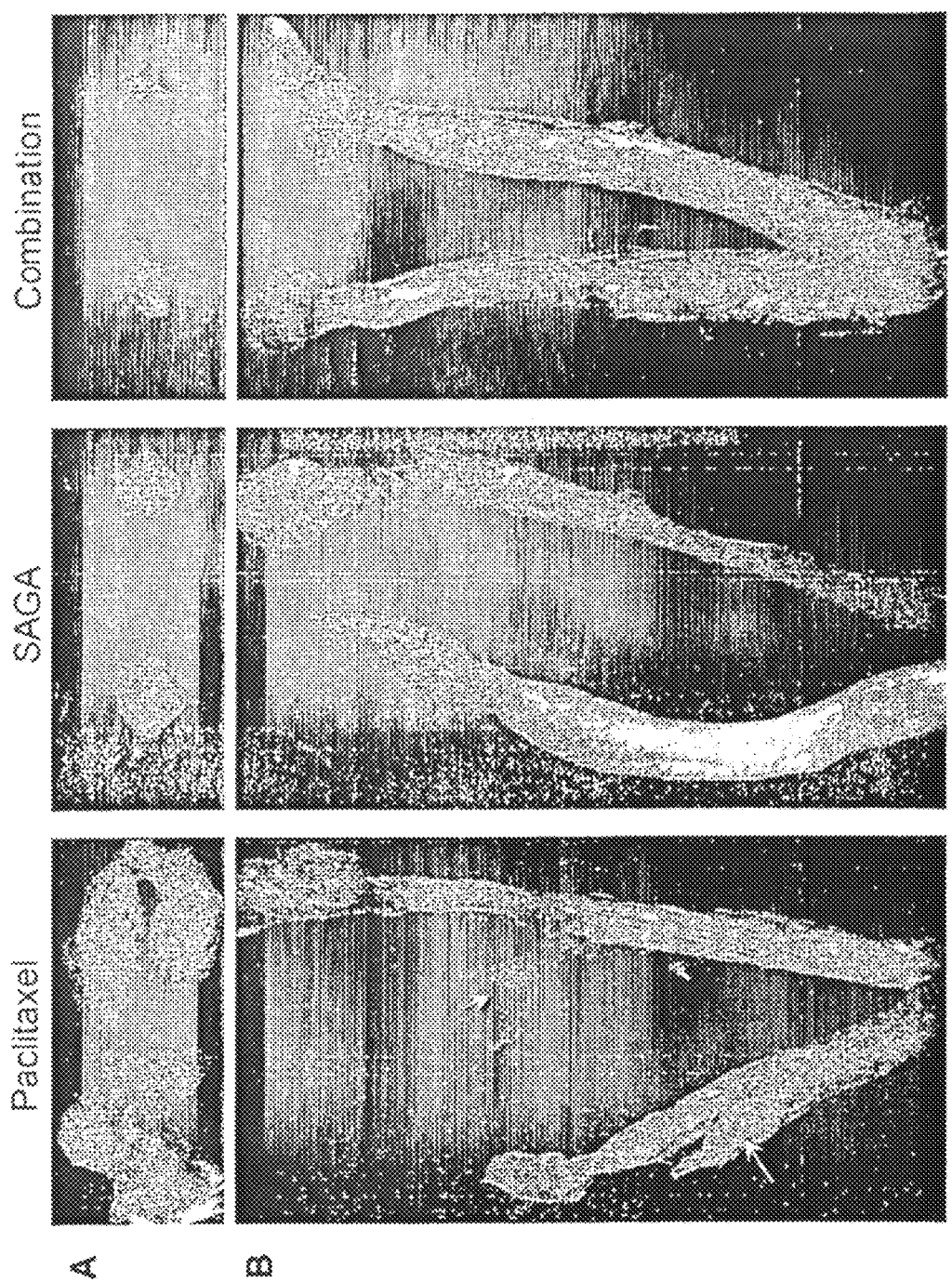
FIG. 11 shows the effects of paclitaxel and SAGA combination therapy on in vivo tumor growth. Female NOD/SCID mice bearing intraperitoneal ovarian tumors were randomized into 3 treatment groups (n=5), and treated for 26 days as described herein. A) Tumors isolated from paclitaxel, SAGA and combinations of SAGA and paclitaxel in treatments administered to animals were compared, revealing clear differences in tumor size due to the treatment (two representative tumors per treatment group are shown). B) The reproductive system was isolated from animals in all treatment groups, and a representative example is shown per group. Metastatic tumor nodules are visible in the paclitaxel treatment group (arrows), but absent in SAGA and combination of SAGA and paclitaxel groups.

To assess potential additive or synergistic effects on the inhibition of tumor growth in vivo, the effect of administering a combination of SAGA and paclitaxel was investigated. Tumors were established in NOD/SCID mice as described herein (n=15). By 3 weeks, all mice had palpable tumors and were randomly assigned to one of 3 treatment groups, paclitaxel, SAGA, or SAGA plus paclitaxel (n=5). Animals were treated for a period of 26 days with paclitaxel (15 mg/kg, 2 injections at 3-week intervals), SAGA (0.5 mg/kg of SAGA DNA coupled to linearized PEI twice weekly) or the combination of SAGA and paclitaxel (0.5 mg/kg of SAGA DNA coupled to linearized PEI twice weekly and 1.5 mg/kg, 2 injections at 3-week intervals, administered 48 hours after SAGA injection). All compositions were administered intraperitoneally. A decrease in tumor size by physical examination was evident in the SAGA and in the combination therapy groups as early as one week after the first treatment course. The decrease in tumor sizes was more significant in animals undergoing combination therapy (Table 5 and FIG. 11). At the end of the 26-day treatment period, 5 of 5 (100%) of the paclitaxel-treated animals still had tumors, compared to 4 of 5 (80%) and 3 of 5 (60%) animals in the SAGA and combination therapy groups, respectively. This result represents an increased response rate in the combination arm compared to that observed with SAGA treatment alone.

TABLE 5

| Treatment | Animals with Tumors at Completion of Therapy | Disease Dissemination | Tumor Weight (mg) | Tumor Size (mm) | Number of Nodules |
|---|---|---|---|---|---|
| Paclitaxel | 5 of 5 | 4 of 5 | 236.0 ± 79.8 | 10.4 ± 1.3 | 6.2 ± 3.9 |
| SAGA | 4 of 5 | 1 of 5 | 46.8 ± 46.6 | 3.5 ± 2.6 | 2.2 ± 0.8 |
| Paclitaxel + SAGA | 3 of 5 | 0 of 5 | 11.2 ± 13.5 | 1.4 ± 1.5 | 0.6 ± 0.5 |

At the completion of the experimental time course, the primary tumor nodules were resected, weighed and measured. Tumors isolated from paclitaxel-treated animals had a mean tumor weight of 236.0 mg compared to 46.8 mg in the SAGA-treated group and 11.2 mg in animals treated with combination therapy. The differences in tumor weight were significant between paclitaxel and SAGA (p=0.004), paclitaxel and combination (p=0.0001) and also between SAGA and combination (p=0.008). Similarly, mean tumor size in paclitaxel-treated animals was 10.4 mm compared to 3.5 mm in SAGA-treated and 1.4 mm in combination-treated animals. These differences were also significant between paclitaxel and SAGA (p=0.0003), paclitaxel and combination (p<0.0001), and SAGA and combination (p=0.038). These findings indicate that although the use of paclitaxel does not have a significant therapeutic effect on ovarian tumors when used as a single agent in this tumor model, its use in combination with SAGA significantly enhances SAGA's efficacy to inhibit tumor growth.

REFERENCES

1. Jemal A, Thomas A, Murray T, Thun M. Cancer statistics, 2002. CA Cancer J Clin 2002; 52(1):23-47.
2. Leung E H, Leung P C, Auersperg N. Differentiation and growth potential of human ovarian surface epithelial cells expressing temperature-sensitive SV40 T antigen. In Vitro Cell Dev Biol Anim 2001; 37(8):515-21.
3. Erkinheimo T L, Lassus H, Finne P, van Rees B P, Leminen A, Ylikorkala O, et al. Elevated cyclooxygenase-2 expression is associated with altered expression of p53 and SMAD4, amplification of HER-2/neu, and poor outcome in serous ovarian carcinoma. Clin Cancer Res 2004; 10(2): 538-45.
4. Berchuck A, Kamel A, Whitaker R, Kems B, Olt G, Kinney R, et al. Overexpression of HER-2/neu is associated with poor survival in advanced epithelial ovarian cancer. Cancer Res 1990; 50(13):4087-91.
5. Marks J R, Davidoff A M, Kerns B J, Humphrey P A, Pence J C, Dodge R K, et al. Overexpression and mutation of p53 in epithelial ovarian cancer. Cancer Res 1991; 51(11):2979-84.
6. Hartmann L C, Podratz K C, Keeney G L, Kamel N A, Edmonson J H, Grill J P, et al. Prognostic significance of p53 immunostaining in epithelial ovarian cancer. J Clin Oncol 1994; 12(1):64-9.
7. Sui L, Dong Y, Ohno M, Watanabe Y, Sugimoto K, Tokuda M. Survivin expression and its correlation with cell proliferation and prognosis in epithelial ovarian tumors. Int J Oncol 2002; 21(2):315-20.
8. Ferrandina G, Legge F, Martinelli E, Ranelletti F O, Zannoni G F, Lauriola L, et al. Survivin expression in ovarian cancer and its correlation with clinico-pathological, surgical and apoptosis-related parameters. Br J Cancer 2005.
9. Ozols R F. Update of the NCCN ovarian cancer practice guidelines. Oncology (Huntingt) 1997; 11(11A):95-105.
10. Ozols R F. Paclitaxel (Taxol)/carboplatin combination chemotherapy in the treatment of advanced ovarian cancer. Semin Oncol 2000; 27(3 Suppl 7):3-7.
11. Lord S J, Rajotte R V, Korbutt G S, Bleackley R C. Granzyme B: a natural born killer. Immunol Rev 2003; 193:31-8.
12. Trapani J A, Sutton V R. Granzyme B: pro-apoptotic, antiviral and antitumor functions. Curr Opin Immunol 2003; 15(5):533-43.
13. Adrain C, Murphy B M, Martin S J. Molecular Ordering of the Caspase Activation Cascade Initiated by the Cytotoxic T Lymphocyte/Natural Killer (CTL/NK) Protease Granzyme B. J Biol Chem 2005; 280(6):4663-73.
14. Metkar S S, Wang B, Ebbs M L, Kim J H, Lee Y J, Raja S M, et al. Granzyme B activates procaspase-3 which signals a mitochondrial amplification loop for maximal apoptosis. J Cell Biol 2003; 160(6):875-85.
15. Talanian R V, Yang X, Turbov J, Seth P, Ghayur T, Casiano C A, et al. Granule-mediated killing: pathways for granzyme B-initiated apoptosis. J Exp Med 1997; 186(8): 1323-31.
16. Sebbagh M, Hamelin J, Bertoglio J, Solary E, Breard J. Direct cleavage of ROCK II by granzyme B induces target cell membrane blebbing in a caspase-independent manner. J Exp Med 2005; 201(3):465-71.
17. Khong H T, Restifo N P. Natural selection of tumor variants in the generation of "tumor escape" phenotypes. Nat Immunol 2002; 3(11):999-1005.
18. Gabrilovich D, Pisarev V. Tumor escape from immune response: mechanisms and targets of activity. Curr Drug Targets 2003; 4(7):525-36.
19. Bots M, Kolfschoten I G, Bres S A, Rademaker M T, de Roo G M, Kruse M, et al. SPI-CI and SPI-6 cooperate in the protection from effector cell-mediated cytotoxicity. Blood 2005; 105(3):1153-61.
20. Classen C F, Ushmorov A, Bird P, Debatin K M. The granzyme B inhibitor PI-9 is differentially expressed in all main subtypes of pediatric acute lymphoblastic leukemias. Haematologica 2004; 89(11):1314-21.
21. Caldas H, Altura R A. Survivin-Mediated Suicide Gene Therapy for Malignant Tumors. In: International Society for Biological Therapy in Cancer 19th Annual Meeting; 2004; San Franscisco, Calif.: Journal of Immunotherapy; 2004. p. S58.
22. Caldas H, Altura R A. Survivin-Driven Therapy for Leukemia. In: American Society of Hematology 46th Annual Meeting; 2004; San Diego, Calif.: Blood; 2004. p. 104 issue 11.
23. Bao R, Connolly D C, Murphy M, Green J, Weinstein J K, Pisarcik D A, et al. Activation of cancer-specific gene expression by the survivin promoter. J Natl Cancer Inst 2002; 94(7):522-8.
24. Chen J S, Liu J C, Shen L, Rau K M, Kuo H P, Li Y M, et al. Cancer-specific activation of the survivin promoter and its potential use in gene therapy. Cancer Gene Ther 2004; 11(11):740-7.

25. Altieri D C. Validating survivin as a cancer therapeutic target. Nat Rev Cancer 2003; 3(1):46-54.
26. Caldas H, Jiang Y, Holloway M P, Fangusaro J, Mahotka C, Conway E M, et al. Survivin splice variants regulate the balance between proliferation and cell death. Oncogene 2005; 24(12): 1994-2007.
27. Caldas H, Honsey L E, Altura R A. Survivin 2alpha: a novel Survivin splice variant expressed in human malignancies. Mol Cancer 2005; 4(1):11.
28. Fangusaro J R, Jiang Y, Holloway M P, Caldas H. Singh V, Boue D R, et al. Survivin, Survivin-2B, and Survivin-deltaEx3 expression in medulloblastoma: biologic markers of tumour morphology and clinical outcome. Br J Cancer 2005; 92(2):359-65.
29. Jiang Y, Saavedra H I, Holloway M P, Leone G, Altura R A. Aberrant regulation of survivin by the RB/E2F family of proteins. J Biol Chem 2004; 279(39):40511-20.
30. Li F, Altieri D C. Transcriptional analysis of human survivin gene expression. Biochem J 1999; 344 Pt 2:305-11.
31. Hoffman W H, Biade S, Zilfou J T, Chen J, Murphy M. Transcriptional repression of the anti-apoptotic survivin gene by wild type p53. J Biol Chem 2002; 277(5):3247-57.
32. Mirza A, McGuirk M, Hockenbery T N, Wu Q, Ashar H, Black S, et al. Human survivin is negatively regulated by wild-type p53 and participates in p53-dependent apoptotic pathway. Oncogene 2002; 21(17):2613-22.
33. Soule H D, Maloney T M, Wolman S R, Peterson W D, Jr., Brenz R, McGrath C M, et al. Isolation and characterization of a spontaneously immortalized human breast epithelial cell line, MCF-10. Cancer Res 1990; 50(18):6075-86.
34. Tait L, Soule H D, Russo J. Ultrastructural and immunocytochemical characterization of an immortalized human breast epithelial cell line, MCF-10. Cancer Res 1990; 50(18):6087-94.
35. Zhu Z B, Makhija S K, Lu B, Wang M, Kaliberova L, Liu B, et al. Transcriptional targeting of tumors with a novel tumor-specific survivin promoter. Cancer Gene Ther 2004; 11(4):256-62.
36. Morimoto H, Safrit J T, Bonavida B. Synergistic effect of tumor necrosis factor-alpha- and diphtheria toxin-mediated cytotoxicity in sensitive and resistant human ovarian tumor cell lines. J Immunol 1991; 147(8):2609-16.
37. Auersperg N, Wong A S, Choi K C, Kang S K, Leung P C. Ovarian surface epithelium: biology, endocrinology, and pathology. Endocr Rev 2001; 22(2):255-88.
38. Fadok V A, Voelker D R, Campbell P A, Cohen J J, Bratton D L, Henson P M. Exposure of phosphatidylserine on the surface of apoptotic lymphocytes triggers specific recognition and removal by macrophages. J Immunol 1992; 148(7):2207-16.
39. Young R C. Three cycles versus six cycles of adjuvant paclitaxel (Taxol)/carboplatin in early stage ovarian cancer. Semin Oncol 2000; 27(3 Suppl 7):8-10.
40. Ikeda H, Chamoto K, Tsuji T, Suzuki Y, Wakita D, Takeshima T, et al. The critical role of type-1 innate and acquired immunity in tumor immunotherapy. Cancer Sci 2004; 95(9):697-703.
41. Ottaiano A, Mollo E, Di Lorenzo G, Pisano C, Di Maio M, Barletta B, et al. Prospective clinical trials of biotherapies in solid tumors: a 5-year survey. Cancer Immunol Immunother 2005; 54(1):44-50.
42. Kahlon K S, Brown C, Cooper U, Raubitschek A, Forman S J, Jensen M C. Specific recognition and killing of glioblastoma multiforme by interleukin 13-zetakine redirected cytolytic T cells. Cancer Res 2004; 64(24):9160-6.
43. Smith C L, Dunbar P R, Mirza F, Palmowski M J, Shepherd D, Gilbert S C, et al. Recombinant modified vaccinia Ankara primes functionally activated CTL specific for a melanoma tumor antigen epitope in melanoma patients with a high risk of disease recurrence. Int J Cancer 2005; 113(2):259-66.
44. Vassaux G, Martin-Duque P. Use of suicide genes for cancer gene therapy: study of the different approaches. Expert Opin Biol Ther 2004; 4(4):519-30.
45. Kirn D, Niculescu-Duvaz I, Hallden G, Springer C J. The emerging fields of suicide gene therapy and virotherapy. Trends Mol Med 2002; 8(4 Suppl):S68-73.
46. Barry M, Heibein J A, Pinkoski M J, Lee S F, Moyer R W, Green D R, et al. Granzyme B short-circuits the need for caspase 8 activity during granule-mediated cytotoxic T-lymphocyte killing by directly cleaving Bid. Mol Cell Biol 2000; 20(11):3781-94.
47. Luo X, Budihardjo I, Zou H, Slaughter C, Wang X. Bid, a Bcl2 interacting protein, mediates cytochrome c release from mitochondria in response to activation of cell surface death receptors. Cell 1998; 94(4):481-90.
48. Slee E A, Harte M T, Kluck R M, Wolf B B, Casiano C A, Newmeyer D D, et al. Ordering the cytochrome c-initiated caspase cascade: hierarchical activation of caspases-2, -3, -6, -7, -8, and -10 in a caspase-9-dependent manner. J Cell Biol 1999; 144(2):281-92.
49. Sutton V R, Wowk M E, Cancilla M, Trapani J A. Caspase activation by granzyme B is indirect, and caspase autoprocessing requires the release of proapoptotic mitochondrial factors. Inmunity 2003; 18(3):319-29.
50. Schiff P B, Fant J, Horwitz S B. Promotion of microtubule assembly in vitro by taxol. Nature 1979; 277(5698):665-7.
51. De Brabander M, Geuens G, Nuydens R, Willebrords R, De Mey J. Taxol induces the assembly of free microtubules in living cells and blocks the organizing capacity of the centrosomes and kinetochores. Proc Natl Acad Sci USA 1981; 78(9):5608-612.
52. Ling X, Bemacki R J, Brattain M G, Li F. Induction of survivin expression by taxol (paclitaxel) is an early event, which is independent of taxol-mediated G2/M arrest. J Biol Chem 2004; 279(15):15196-203.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features set forth herein.

What is claimed is:

1. A recombinant nucleic acid molecule comprising at least one expression control region for an inhibitor of apoptosis gene operatively linked to a polynucleotide comprising a coding region of an active apoptosis-inducing protein (AIP), wherein the expression control region is the human survivin promoter comprising a sequence selected from the group consisting of SEQ ID NO:1 and nucleotides 68-268 of SEQ ID NO:1, and wherein the coding region comprises a sequence encoding a protein selected from the group consisting of Granzyme B (SEQ ID NO: 4), Granzyme B (SEQ ID NO: 6), Granzyme H (SEQ ID NO: 38), Granzyme C (SEQ ID NO: 26), Granzyme F (SEQ ID NO: 31), and variants of the coding region that are at least 90% identical to the coding region and encode a protein retaining an apoptosis-inducing function.

2. A pharmaceutical composition comprising the recombinant nucleic acid molecule according to claim 1 and a pharmaceutically acceptable carrier.

3. A kit comprising the pharmaceutical composition according to claim 1 and a set of instruction for the administration thereof.

* * * * *